(12) United States Patent
Iida et al.

(10) Patent No.: US 8,741,650 B2
(45) Date of Patent: Jun. 3, 2014

(54) METHODS FOR PRODUCING MINUS-STRAND RNA VIRAL VECTORS USING HYBRID PROMOTER COMPRISING CYTOMEGALOVIRUS ENHANCER AND CHICKEN β-ACTIN PROMOTER

(75) Inventors: Akihiro Iida, Ibaraki (JP); Hiroshi Ban, Ibaraki (JP); Makoto Inoue, Ibaraki (JP); Takahiro Hirata, Ibaraki (JP); Mamoru Hasegawa, Ibaraki (JP)

(73) Assignee: DNAVEC Research Inc., Tsukuba-shi, Ibaraki (JP)

( * ) Notice: Subject to any disclaimer, the term of this patent is extended or adjusted under 35 U.S.C. 154(b) by 1439 days.

(21) Appl. No.: 10/586,142

(22) PCT Filed: Jan. 20, 2005

(86) PCT No.: PCT/JP2005/000705
§ 371 (c)(1),
(2), (4) Date: Dec. 13, 2006

(87) PCT Pub. No.: WO2005/071092
PCT Pub. Date: Aug. 4, 2005

(65) Prior Publication Data
US 2007/0161110 A1 Jul. 12, 2007

(30) Foreign Application Priority Data

Jan. 22, 2004 (JP) ................................. 2004-014653

(51) Int. Cl.
*C12N 15/86* (2006.01)

(52) U.S. Cl.
USPC ........................................................ 435/456

(58) Field of Classification Search
None
See application file for complete search history.

(56) References Cited

U.S. PATENT DOCUMENTS

| | | | |
|---|---|---|---|
| 5,770,400 | A | 6/1998 | Miyazaki et al. |
| 6,645,760 | B2 | 11/2003 | Nagai et al. |
| 6,723,532 | B2 | 4/2004 | Nagai et al. |
| 7,402,427 | B2 | 7/2008 | Kinoh et al. |
| 2002/0169306 | A1 | 11/2002 | Kitazato et al. |
| 2003/0022376 | A1 | 1/2003 | Kitazato et al. |
| 2003/0166252 | A1 | 9/2003 | Kitazato et al. |
| 2003/0170266 | A1 | 9/2003 | Kitazato et al. |
| 2005/0266566 | A1 | 12/2005 | Nagai |
| 2007/0009949 | A1 | 1/2007 | Kitazato et al. |
| 2008/0014183 | A1 | 1/2008 | Okano et al. |
| 2008/0031855 | A1 | 2/2008 | Okano et al. |
| 2008/0299642 | A1 | 12/2008 | Kinoh et al. |
| 2009/0170798 | A1 | 7/2009 | Hara et al. |
| 2009/0246170 | A1 | 10/2009 | Inoue et al. |

FOREIGN PATENT DOCUMENTS

| | | |
|---|---|---|
| EP | 0864645 | 9/1998 |
| WO | WO97/16539 | 5/1997 |
| WO | WO-0009700 A1 | 2/2000 |
| WO | WO00/70055 | 11/2000 |
| WO | WO00/70070 | 11/2000 |
| WO | WO03/025570 | 3/2003 |
| WO | WO03/093476 | 11/2003 |

OTHER PUBLICATIONS

Ito, N. et al., "Rescue of Rabie Virus from cloned DNA and Identification of the Pathogenicity-Related Gene: Glycoprotein Gene Is Associated with Virulence for Adult Mice", 2001, J. Virol. vol. 75: pp. 9121-9128.*

Li et al., "A Cytoplasmic RNA vector Derived from Nontransmissable Sendai Virus with Efficient Gene Transfer and Expresion", 2000, J. Virol., vol. 74: pp. 6564-6569.*

Neumann, G. et al., "Ebola Virus VP40 Late Domains Are Not Essential for Vital Replications in Cell Culture", 2005, J. Virol., vol. 79: pp. 10300-10307.*

Buchholz et al., "Generation of Bovine Respiratory Syncytial Virus (BRSV) from cDNA: BRSV NS2 Is Not Essential for Virus Replication in Tissue Culture, and the Human RSV Leader Region Acts as a Functional BRSV Genome Promoter," *Journal of Virology.* 73(1):251-259 (1999).

Engel-Herbert et al., "Characterization of a recombinant Newcastle disease virus expressing the green fluorescent protein," *Journal of Virological Methods.* 108(1):19-28 (2003).

Finke and Conzelmann, "Virus Promoters Determine Interference by Defective RNAs: Selective Amplification of Mini-RNA Vectors and Rescue from cDNA by a 3' Copy-Back Ambisense Rabies Virus," *Journal of Virology.* 73(5):3818-3825 (1999).

Fuerst et al., "Eukaryotic transient-expression system based on recombinant vaccinia virus that synthesizes bacteriophage T7 RNA polymerase," *Proc Natl Acad Sci USA.* 83(21):8122-8126 (1986).

Garcin et al., "A highly recombinogenic system for the recovery of Infectious Sendai paramyxovirus from cDNA: generation of a novel copy-back nondefective interfering virus," *The EMBO Journal.* 14(24):6087-6094 (1995).

Harty et al., "Vaccinia Virus-Free Recovery of Vesicular Stomatitis Virus," *J Mol Microbiol Biotechnol.* 3(4):513-517 (2001).

(Continued)

*Primary Examiner* — Michael Burkhart
(74) *Attorney, Agent, or Firm* — Clark & Elbing LLP

(57) ABSTRACT

The present invention provides methods for producing a minus-strand RNA viral vector, which comprise using a promoter comprising a cytomegalovirus enhancer and a chicken β-actin promoter, to induce the transcription of the genome RNA of a minus-strand RNA viral vector and the expression of minus-strand RNA viral proteins that form a ribonucleoprotein with the genome RNA. The methods of the present invention enable high efficiency production of highly safe minus-strand RNA viral vectors. The methods of the present invention are particularly useful for producing minus-strand RNA viral vectors that are deficient in envelope-constituting protein genes.

5 Claims, 22 Drawing Sheets

(56) References Cited

OTHER PUBLICATIONS

Hoffmann et al., "A DNA transfection system for generation of influenza A virus from eight plasmids," *PNAS.* 97(11):6108-6113 (2000).

Hoffmann et al., "Rescue of influenza B virus from eight plasmids," *PNAS.* 99(17):11411-11416 (2002).

Inoue et al., "An improved method for recovering rabies virus from cloned cDNA," *Journal of Virological Methods.* 107(2):229-236 (2003).

Inoue et al., "Nontransmissible Virus-Like Particle Formation by F-Deficient Sendai Virus Is Temperature Sensitive and Reduced by Mutations in M and HN Proteins," *Journal of Virology.* 77(5):3238-3246 (2003).

Inoue et al., "A New Sendai Virus Vector Deficient in the Matrix Gene Does Not Form Virus Particles and Shows Extensive Cell-to-Cell Spreading," *Journal of Virology.* 77(11):6419-6429 (2003).

Iseni, "Sendai virus trailer RNA binds TIAR, a cellular protein involved in virus-induced apoptosis," *The EMBO Journal.* 21(19):5141-5150 (2002).

Ito et al., "Improved Recovery of Rabies Virus from Cloned cDNA Using a Viccinla Virus-Free Reverse Genetics System," *Microbiol Immunol.* 47(8):613-617 (2003).

Kato et al., "Initiation of Sendai virus multiplication from transfected cDNA or RNA with negative or positive sense," *Genes to Cells.* 1(6):569-579 (1996).

Lerch et al., "Rescue of Human Respiratory Syncytial Virus Subgroup B Viruses From cDNA Using a Plasmid Based Expression System," *International Conference on Negative Strand Viruses.* Jun. 14-19:154, Abstract 206 (2003).

Neumann et al., "Generation of Influenza A viruses entirely from cloned cDNAs," *Proc Natl Acad Sci USA.* 96(16):9345-9350 (1999).

Neumann et al., "A decade after the generation of a negative-sense RNA virus from cloned cDNA—what have we learned?" *Journal of General Virology.* 83(11):2635-2662 (2002).

Niwa et al., "Efficient selection for high-expression transfectants with a novel eukaryotic vector," *Gene.* 108(2):193-199 (1991).

Radecke et al., "Rescue of measles viruses from cloned DNA," *The EMBO Journal.* 14(23):5773-5784 (1995).

Romer-Oberdorfer et al., "Generation of recombinant lentogenic Newcastle disease virus from cDNA," *Journal of General Virology.* 80(11):2987-2995 (1999).

Sutter et al., "Non-replicating vaccinia vector efficiently expresses bacteriophage T7 RNA polymerase," *FEBS Letter.* 371(1):9-12 (1995).

Takeda et al., "Protective Efficacy of an AIDS Vaccine, a Single DNA Priming Followed by a Single Booster with a Recombinant Replication-Defective Sendai Virus Vector, in a Macaque AIDS Model," *Journal of Virology.* 77(17):9710-9715 (2003).

Waning et al., "Roles for the Cytoplasmic Tails of the Fusion and Hemagglutinin-Neuraminidase Proteins in Budding of the Paramyxovirus Simian Virus 5," *Journal of Virology.* 76(18):9284-9297 (2002).

Witko et al., "An efficient helper-virus-free method for rescue of recombinant paramyxoviruses and rhadoviruses from a cell line suitable for vaccine development," *Journal of Virological Methods.* 135(1):91-101 (2006).

Bitzer et al., "Sendai virus vectors as an emerging negative-strand RNA viral vector system," *J. Gene Med.* 5: 543-553 (2003).

Chen et al., "Protection against influenza B virus infection by immunization with DNA vaccines," *Vaccine* 19: 1446-1455 (2001).

European Search Report for European Patent Application No. 05 70 3933, completed Dec. 18, 2008.

He et al., "Recovery of infectious SV5 from cloned DNA and expression of a foreign gene," *Virology* 237: 249-260 (1997).

Shoji et al., "Generation and characterization of P gene-deficient rabies virus," *Virology* 318: 295-305 (2004).

U.S. Appl. No. 12/712,905 Title of Invention: Vectors With Modified Protease-Dependent Tropism, filed Feb. 25, 2010, Hiroaki Kinoh et al.

U.S. Appl. No. 11/922,278 Title of Invention: Methods for Producing Antibodies, filed Dec. 13, 2007, Yasuji Ueda et al.

Curran et al., "The Sendai Virus P Gene Expresses Both an Essential Protein and an Inhibitor of RNA Synthesis by Shuffling Modules via mRNA Editing," *EMBO J.* 10(10):3079-3085, 1991.

Li et al., "A Cytoplasmic RNA Vector Derived from Nontransmissible Sendai Virus with Efficient Gene Transfer and Expression," *J. Virol.* 74(14):6564-6569, 2000.

Aoki et al., "A human liver cell line exhibits efficient translation of HCV RNAs produced by a recombinant adenovirus expressing T7 RNA polymerase," *Virology* 250(1): 140-150 (1998).

Dutch et al., "Deletetion of the cytoplasmic tail of the fusion protein of the paramyxovirus simian virus 5 affects fusion pore enlargement," *J. Virol.* 75(11): 5363-5369 (2001).

Engelhorn et al., "Molecular cloning and characterization of a Sendai virus internal deletion defective RNA," *J. Gen. Virol.* 74(Pt 1): 137-141 (1993).

International Search Report for PCT/JP2005/000705, completed Feb. 8, 2005, mailed Mar. 8, 2005 (2 pages).

Neumann et al., "Reverse genetics demonstrates that proteolytic processing of the Ebola virus glycoprotein is not essential for replication in cell culture," *J. Virol.* 76(1): 406-410 (2002).

Okuma et al., "Host range of human T-cell leukemia virus type I analyzed by a cell fusion-dependent reporter gene activation assay," *Virology* 254(2): 235-244 (1999).

Yoshizaki et al., "Naked Sendai virus vector lacking all of the envelope-related genes: reduced cytopathogenicity and immunogenicity," *J. Gene Med.* 8(9): 1151-1159 (2006).

Arai et al., "A New System for Stringent, High-Titer Vesicular Stomatitis Virus G Protein-Pseudotyped Retrovirus Vector Induction by Introduction of Cre Recombinase into Stable Prepackaging Cell Lines," *J. Virol.* 72:1115-1121 (1998).

\* cited by examiner 5.4 x 10⁸ CIU/ml

METHODS FOR PRODUCING MINUS-STRAND RNA VIRAL VECTORS USING HYBRID PROMOTER COMPRISING CYTOMEGALOVIRUS ENHANCER AND CHICKEN β-ACTIN PROMOTER

CROSS-REFERENCE TO RELATED APPLICATIONS

This application is the U.S. National Stage of International Application No. PCT/JP2005/000705, filed Jan. 20, 2005, which, in turn, claims the benefit of Japanese Patent Application No. 2004-014653, filed Jan. 22, 2004.

TECHNICAL FIELD

The present invention relates to methods for producing minus-strand RNA viral vectors.

BACKGROUND ART

Conventionally, minus-strand RNA viruses are harvested mainly by using a recombinant vaccinia virus expressing T7 RNA polymerase (vTF7-3: Fuerst, T. R. et al., Proc. Natl. Acad. Sci. USA 83, 8122-8126(1986), MVA-T7: Sutter, G. et al., FEBS lett. 371: 9-12 (1995)) and plasmids expressing NP, P, and L genes and minus-strand RNA viral genome under the control of a T7 promoter (Kolakofsky, et al., EMBO J. 14: 6087-6094 (1995); Kato, A. et al., Genes Cells 1: 569-579 (1996)). NP, P, and L, and antigenome RNA are supplied by the action of the T7 RNA polymerase expressed by the recombinant vaccinia virus. The cap structure is formed at 5' ends of the NP, P, and L mRNAs through the action of a capping enzyme from the vaccinia virus. Then, the mRNAs are translated into proteins. The proteins interact with the antigenome RNA and constitute functional RNP. Then, genome RNP is replicated from the antigenome RNP. The viral proteins are also translated, and the infection cycle is initiated. The virus is then harvested.

The minus-strand RNA viral vector can be harvested by using a recombinant vaccinia virus. However, the vaccinia virus must be removed for the final vector preparation. This is costly and time-consuming. From the viewpoint of safety, it is desirable not to use a vaccinia virus for harvesting a vector if it is intended to be used as a vector for gene therapy.

Non-patent Document 1: Fuerst, T. R. et al., Proc. Natl. Acad. Sci. USA 83, 8122-8126 (1986)

Non-patent Document 2: Sutter G, et al, FEBS lett. 371: 9-12 (1995)

Non-patent Document 3: Kolakofsky et al., EMBO J. 14: 6087-6094 (1995)

Non-patent Document 4: Kato, A. et al., Genes Cells 1: 569-579 (1996)

DISCLOSURE OF THE INVENTION

The present invention provides methods for producing minus-strand RNA viral vectors using a hybrid promoter comprising a cytomegalovirus enhancer and a chicken β-actin promoter without using vaccinia virus.

Until now, some mononegaviruses have been used to develop methods for harvesting viruses without the use of recombinant vaccinia viruses. One of such methods uses a mammalian cell line that constitutively expresses T7 RNA polymerase. Unlike when using the vaccinia virus, in this method the capping enzyme is not available. Therefore, to express NP, P, and L proteins, this method uses an expression plasmid carrying an IRES sequence, which allows cap-independent translation. It has been reported that this method was used to harvest bovine respiratory syncytial virus (BRSV) (Ursula, et al., J. Virol. 73:251-259 (1999)), Rabies virus (Stefan, et al., J. Virol. 73:3818-3825 (1999)), Newcastle disease virus (NDV)(Romer-Oberdorfer, et al., J. General Virology 80:2987-2995 (1999)), and Sendai virus (F. Iseni, et al., EMBO J. Vol. 21:5141-5150 (2002)). For SV5, a method (David L. Waning et al., J. Virol. 76:9284-9297 (2002)) is reported to use the BSR-T7/5 cell (i.e., the same cell as described above) to express an antigenome by T7 RNA polymerase, and the expression of NP, P, and L proteins is driven by pCAGGS which carries a CAG promoter transcribed by cell-derived RNA polymerase II.

The second method reported is a method for harvesting Rabies virus, in which the cytomegalovirus promoter drives the expression of all NP, P, L and the genome (K. Inoue, et al., J. Virological Method. 107:229-236 (2003)). In this method, the virus can be harvested without using a T7 RNA polymerase-expressing cell line because a hammerhead ribozyme has been attached to the 5' end of the antigenome to accurately cleave off the end of the genome.

However, all these methods are for reconstituting transmissible viruses. Reconstitution of nontransmissible viruses has not been achieved in the past without using vaccinia virus. To reconstitute nontransmissible viruses, it is necessary to delete envelope protein-encoding genes from the viral genome and to form transmissible viral particles by supplying the envelope proteins in trans at the time of virus reconstitution. Therefore, highly efficient reconstitution of such deficient viruses requires a more efficient virus production system as compared with the reconstitution of transmissible viruses.

The present inventors modified a method for driving the transcription of viral genome in virus-producing cells to develop a more efficient method for producing and harvesting minus-strand RNA viruses. As a result, the inventors discovered that efficient production of viruses could be achieved, by using a hybrid promoter comprising a cytomegalovirus enhancer and a chicken β-actin promoter (referred to as CA promoter) to directly or indirectly drive the transcription of the genome RNA of a minus-strand RNA virus, as well as the expression of all the minus-strand RNA virus proteins that form a ribonucleoprotein(s) with the genome RNA. In the present invention, the transcription of the genome RNA is achieved as follows: DNA encoding the genome RNA of a minus-strand RNA virus is operably linked to a CA promoter, and transcription of the genome RNA is then directly induced using the CA promoter. Alternatively, a signal sequence for a bacteriophage-derived RNA polymerase is linked upstream of the genome RNA-encoding DNA, and the RNA polymerase is expressed by a CA promoter, thereby inducing the transcription of the genome RNA. These methods enabled to produce high-titer viruses without using vaccinia virus.

The present inventors then used these methods and succeeded for the first time in harvesting nontransmissible minus-strand RNA viruses that lack one or both F protein and M protein, which are envelope proteins, or genes encoding them, without using vaccinia virus. The method of the present invention is useful for producing high safety viruses for gene therapy or such because the method can prepare high-titer minus-strand RNA viruses using no vaccinia virus at all.

Specifically, the present invention relates to methods for producing minus-strand RNA viruses, which comprise using a CA promoter to induce transcription of the genome RNA of a minus-strand RNA virus and the expression of minus-strand RNA virus proteins that form ribonucleoproteins with the genome RNA. More specifically, the present invention relates to the invention according to each claim. The present invention also relates to inventions comprising a desired combination of one or more (or all) inventions set forth in the claims, in particular, to inventions comprising a desired combination of one or more (or all) inventions set forth in claims (dependent claims) that cite the same independent claim(s) (claim(s) relating to inventions not encompassed by inventions recited in other claims). An invention set forth in an independent claim is also intended to include any combinations of the inventions set forth in its dependent claims. Specifically, the present invention includes:

[1] a method for producing a minus-strand RNA viral vector, which comprises using a promoter comprising a cytomegalovirus enhancer and a chicken β-actin promoter to induce, in a virus-producing cell, (i) the transcription of a minus-strand RNA virus genome RNA or the complementary strand thereof, and (ii) the expression of minus-strand RNA viral proteins that form a ribonucleoprotein with the genome RNA:

[2] the method of [1], which comprises the step of transcribing in the virus-producing cell, a DNA that encodes a ribozyme and the minus-strand RNA virus genome RNA or the complementary strand thereof and that is operably linked with the promoter comprising the cytomegalovirus enhancer and chicken β-actin promoter, wherein the ribozyme has an activity of cleaving the transcript between the ribozyme and the genome RNA or the complementary strand thereof;

[3] the method of [1], which comprises the steps of:
expressing a bacteriophage RNA polymerase-encoding DNA under the control of the cytomegalovirus enhancer and chicken β-actin promoter-comprising promoter in the virus-producing cell; and
transcribing with the RNA polymerase, a DNA that encodes the minus-strand RNA virus genome RNA or the complementary strand thereof, and that is operably linked with a recognition sequence of the RNA polymerase in the virus-producing cell;

[4] the method of [2], wherein the ribozyme is a hammerhead ribozyme;

[5] the method of [3], wherein the RNA polymerase-encoding DNA is expressed episomally in the virus-producing cell;

[6] the method of [3], wherein the RNA polymerase-encoding DNA is expressed from a chromosome in the virus-producing cell;

[7] the method of [3], [5], or [6], wherein the bacteriophage is selected from the group consisting of SP6 phage, T3 phage, and T7 phage;

[8] the method of any one of [1] to [7], wherein the minus-strand RNA virus is Sendai virus;

[9] the method of any one of [1] to [8], wherein the genome RNA or the complementary strand thereof lacks one or more genes encoding an envelope-constituting protein, and wherein the method further comprises the step of expressing a DNA encoding an envelope-constituting protein in the cell;

[10] a DNA that encodes a ribozyme and a minus-strand RNA virus genome RNA or the complementary strand thereof and that is operably linked with a promoter comprising a cytomegalovirus enhancer and a chicken β-actin promoter, wherein the ribozyme has an activity of cleaving a transcript between the ribozyme and the minus-strand RNA virus genome RNA or the complementary strand thereof;

[11] the DNA of [10], wherein the genome RNA or the complementary strand thereof lacks one or more genes encoding an envelope-constituting protein;

[12] the DNA of [10] or [11], wherein the minus-strand RNA virus is Sendai virus;

[13] the DNA of any one of [10] to [12], wherein the ribozyme is a hammerhead ribozyme;

[14] the DNA of any one of [10] to [13], wherein the DNA expression is inducible by a recombinase;

[15] the DNA of [14], wherein the recombinase is Cre or Flp;

[16] a bacteriophage RNA polymerase-encoding DNA that is operably linked with a promoter comprising a cytomegalovirus enhancer and a chicken β-actin promoter;

[17] the DNA of [16], wherein the bacteriophage is selected from the group consisting of SP6 phage, T3 phage, and T7 phage;

[18] the DNA of [16] or [17], wherein the expression of the DNA is inducible by a recombinase;

[19] the DNA of [18], wherein the recombinase is Cre or Flp;

[20] a mammalian cell maintaining the DNA of any one of [10] to [15];

[21] the mammalian cell of [20], which is a cell for minus-strand RNA virus production;

[22] the mammalian cell of [20] or [21], wherein the genome RNA or the complementary strand thereof lacks one or more genes encoding an envelope-constituting protein;

[23] the mammalian cell of any one of [20] to [22], wherein the minus-strand RNA virus is Sendai virus;

[24] a mammalian cell maintaining the DNA of any one of [16] to [19];

[25] the mammalian cell of [24], which is a cell for minus-strand RNA virus production;

[26] the mammalian cell of [24] or [25], which further maintains a DNA that encodes a minus-strand RNA virus genome RNA or the complementary strand thereof and that is operably linked with a recognition sequence of the RNA polymerase;

[27] the mammalian cell of [26], wherein the genome RNA or the complementary strand thereof lacks one or more genes encoding an envelope-constituting protein; and

[28] the mammalian cell of any one of [25] to [27], wherein the minus-strand RNA virus is Sendai virus.

BEST MODE FOR CARRYING OUT THE INVENTION

Figure 1:
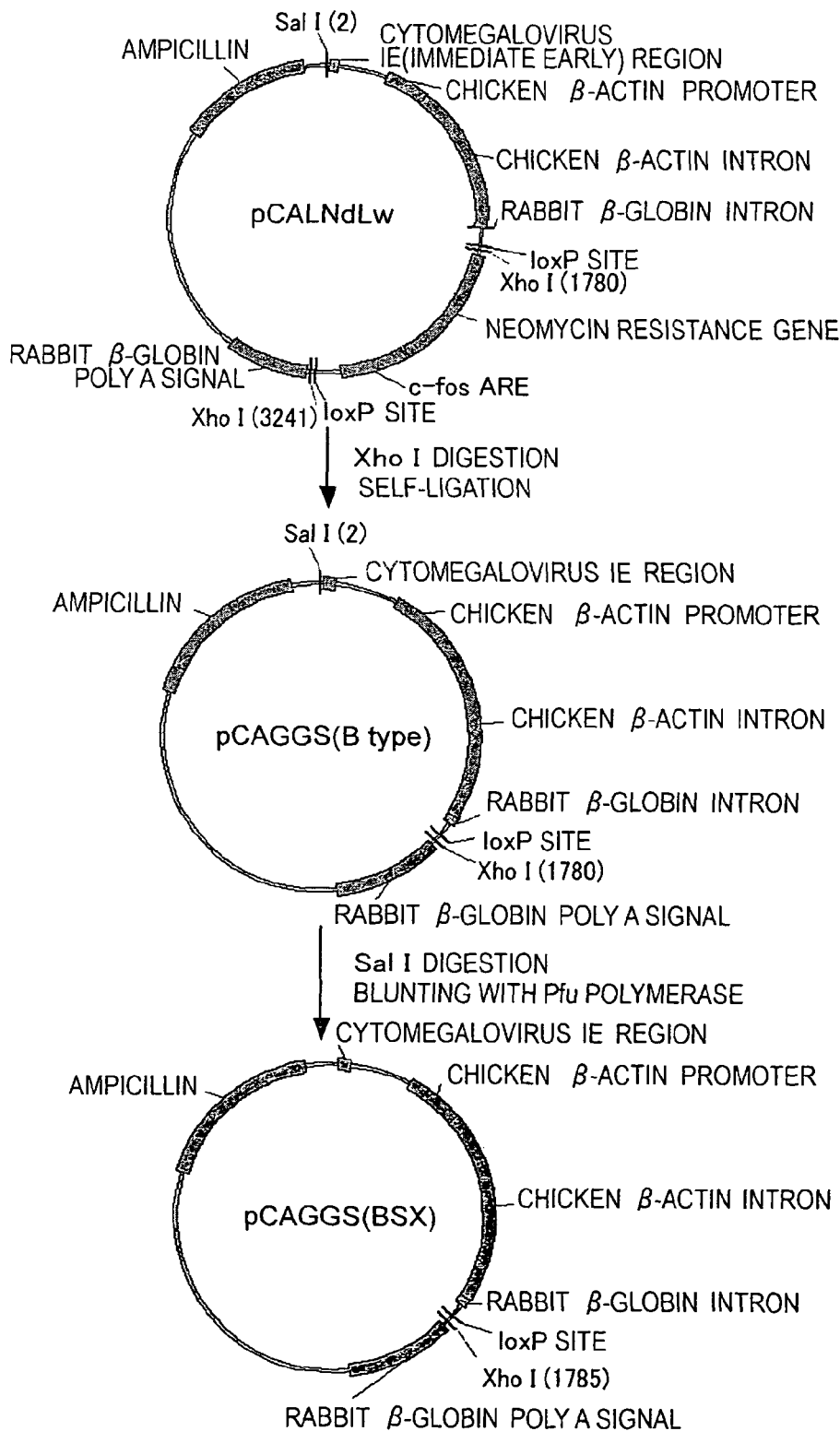
FIG. 1 shows the procedure for constructing pCAGGS (B type) and pCAGGS(BSX).

The present invention relates to methods for producing minus-strand RNA viral vectors, which comprise using a hybrid promoter comprising a cytomegalovirus enhancer and a chicken β-actin promoter (herein referred to as a CA promoter) to induce the transcription of the genome RNA of a minus-strand RNA virus and the expression of all the minus-strand RNA virus proteins that form a ribonucleoprotein (RNP) with the genome RNA in virus-producing cells. In the methods of the present invention, the transcription of the genome RNA of a minus-strand RNA virus is induced directly or indirectly by a CA promoter. To directly induce the transcription of the genome RNA of a minus-strand RNA virus by a CA promoter, DNA encoding the genome RNA of the minus-strand RNA virus (minus strand) or the complementary strand thereof (plus strand) is operably linked to the CA promoter. The phrase "operably linked" means that a DNA encoding the gene of interest is linked downstream of the promoter so that the gene is transcribed according to the promoter activity. To indirectly induce the transcription of the genome RNA of a minus-strand RNA virus by a CA promoter, for example, an RNA polymerase-encoding DNA that is operably linked to a CA promoter, and a DNA that encodes a minus-strand RNA virus genome RNA or the complementary strand thereof (i.e., it may be a plus or minus strand) and that is operably linked to a recognition sequence of the RNA polymerase, are constructed and introduced into cells. The phrase "a recognition sequence of the RNA polymerase" means a DNA sequence that serves as a signal for the polymerase to initiate transcription. The genome RNA (or antigenome RNA) of a minus-strand RNA virus can be transcribed by the polymerase by linking the recognition sequence with a DNA that encodes the genome RNA or the complementary strand thereof. The CA promoter induces the expression of the RNA polymerase, and the RNA polymerase induces the transcription of the minus-strand RNA virus genome. As described in the Examples, indirectly inducing the transcription of the genome RNA of a minus-strand RNA virus through the induction of RNA polymerase can produce viruses with higher titer than those produced by directly inducing the transcription of the genome RNA of a minus-strand RNA virus by CA promoter.

"Minus-strand RNA virus proteins that constitute RNP with genome RNA" refers to a group of viral proteins that form a complex with the genome RNA of a minus-strand RNA virus and which are required for the replication of the genome RNA as well as the expression of the genes encoded by the genome. An expression vector in which the protein coding sequences are simply linked downstream of a CA promoter may be used to express the proteins described above. Thus, the expression of the group of proteins is directly induced by the CA promoter. These proteins form a core without the viral envelope, and are typically N (Nucleocapsid), P (phospho-), and L (Large) proteins. Although these notations vary in some viral species, proteins corresponding to the above are obvious to those skilled in the art (Anjeanette Robert et al., Virology 247:1-6 (1998)). For example, "N" is sometimes referred to as "NP".

Specifically, the present invention's methods for producing minus-strand RNA viral vectors comprise the steps of:
(a) using a CA promoter to induce the transcription of the genome RNA of a minus-strand RNA virus or the complementary strand thereof, and the expression of the viral proteins constituting a ribonucleoprotein (RNP) of the minus-strand RNA virus in manunalian cells; and
(b) recovering the minus-strand RNA virus produced in these cells, or a propagation product thereof.

The genome RNA of a minus-strand RNA virus or the complementary strand thereof (antigenome RNA) forms RNP with viral proteins that constitute the minus-strand RNA virus RNP. The viral proteins encoded by the genome are expressed, thereby amplifying the genome RNA and antigenome RNA in cells. Envelope proteins are incorporated to generate viral particles. The virus can be obtained by harvesting the particles.

The generated virus can be suitably amplified. Transmissible viruses that carry envelope genes propagate via the ordinary viral propagation cycle when infecting mammalian cells. In the case of nontransmissible viruses that lack envelope protein-encoding genes, infectious viruses can be amplified by introducing the viruses into cells (helper cells) expressing the envelope proteins.

Herein, the promoter comprising a cytomegalovirus enhancer and a chicken β-actin promoter (CA promoter) refers to a promoter comprising (i) an enhancer sequence of a cytomegalovirus (CMV) immediate early (IE) gene and (ii) a promoter sequence of a chicken β-actin gene. For the CMV IE enhancer, the enhancer of an immediately early gene from a desired CMV strain can be used, for example, DNA comprising the nucleotide sequence of SEQ ID NO: 1.

The chicken β-actin promoter includes a DNA fragment with promoter activity that comprises a transcription initiation site for the genomic DNA of the chicken β-actin gene. The nucleotide sequence of the chicken β-actin gene promoter has been reported by, for example, T. A. Kost et al. (Nucl. Acids Res. 11, 8287-8301, 1983). The chicken β-actin gene promoter is a gene fragment which has relatively a high G (guanine) and C (cytosine) content and contains sequences characteristic of promoters such as the TATA box (Ann. Rev. Biochem. 50, 349-383, 1981) and CCAAT box (Nucl. Acids Res. 8, 127-142, 1980). In the chicken β-actin promoter, the region from G (guanine) at position -909 to G (guanine) at position -7 upstream of the translation initiation codon (ATG) of the original β-actin structural gene is considered as an intron. Since this intron has transcription-promoting activity, it is preferable to use a genomic DNA fragment comprising at least a portion of this intron. Specifically, examples of this kind of chicken β-actin promoter include, for example, DNA comprising the nucleotide sequence of SEQ ID NO: 2. For the intron acceptor sequence, an intron acceptor sequence from a different gene is preferably used. For example, a splicing acceptor sequence of rabbit β-globin may be used. Specifically, the acceptor site of the second intron, which is located immediately before the initiation codon of rabbit β-globin, can be used. More specifically, such acceptor sequences include, for example, DNA comprising the nucleotide sequence of SEQ ID NO: 3. A CA promoter of the present invention is preferably a DNA in which a chicken β-actin promoter comprising a portion of the intron is linked downstream of a CMV IE enhancer sequence and a desired intron acceptor sequence is added downstream thereof. An example is shown in SEQ ID NO: 4. To express a protein, the last ATG in this sequence is used as the start codon and the coding sequence for the protein of interest may be linked thereto. To transcribe a minus-strand RNA viral genome, DNA encoding the minus-strand RNA viral genome or the complementary strand thereof (either a plus or minus strand) is linked downstream of the intron acceptor sequence described above. However, as described below, it is preferable to insert a DNA encoding a self-cleaving ribozyme between the intron acceptor sequence and the DNA encoding a minus-strand RNA viral genome.

The CMV enhancer sequence and chicken β-actin gene promoter, which are used as the hybrid promoter, vary in their sequences depending on the strains or individuals from which the sequences are isolated. These sequences may be slightly modified so that restriction enzyme recognition sites can be added or deleted, or linker sequences can be inserted. Specifically, the sequences may not be completely identical to the exemplary sequence shown in SEQ ID NO: 4. Such sequences can be suitably used as long as they have an equivalent or higher (for example, 70% or higher, preferably 80% or higher, 90% or higher, or 100% or higher) promoter activity. Methods for introducing mutations into nucleotide sequences are well known to those skilled in the art (Molecular cloning: a laboratory manual, 3rd ed., Joseph Sambrook, David W. Russell, Cold Spring Harbor Laboratory Press, 2001). Variants of the CMV enhancer sequence and chicken β-actin gene promoter sequence include, for example, those that have Genbank accession numbers AF334827, AY237157, AJ575208, and X00182, and these sequences can be used in the present invention. To identify from the above sequences those that are required for constructing a CA promoter, the sequences may be aligned with SEQ ID NOs: 1 and 2 and matched regions may be selected from the alignments. DNA excised from pCAGGS (Niwa, H. et al. (1991) Gene. 108: 193-199, Japanese Patent Application Kokai Publication No. (JP-A) H3-168087 (unexamined, published Japanese patent application) or pCALNdLw (Arai, T. et al. J. Virology 72, 1998, p 1115-1121) can be used to construct a CA promoter.

Variants of the CMV IE enhancer sequence and chicken β-actin promoter as described above include sequences that have equivalent promoter activity, and which comprise a nucleotide sequence having a substitution, deletion, and/or insertion of 30% or less, preferably 20% or less, more preferably 15% or less, more preferably 10% or less, more preferably 5% or less, more preferably 3% or less of the nucleotides in the CMV IE enhancer sequence of SEQ ID NO: 1 and the chicken β-actin promoter of SEQ ID NO: 2. These sequences exhibits high homology to the nucleotide sequence of either SEQ ID NO: 1 or 2. High homology nucleotide sequences include those with an identity of, for example, 70% or higher, more preferably 75% or higher, even more preferably 80% or higher, still more preferably 85% or higher, yet more preferably 90% or higher, even still more preferably 93% or higher, yet still more preferably 95% or higher, yet still even more preferably 96% or higher. The nucleotide sequence identity can be determined, for example, using the BLAST program (Altschul, S. F. et al., 1990, J. Mol. Biol. 215: 403-410). For example, search is carried out on the BLAST web page of NCBI (National Center for Biotechnology Information) using default parameters, with all the filters including Low complexity turned off (Altschul, S. F. et al. (1993) Nature Genet. 3:266-272; Madden, T. L. et al. (1996) Meth. Enzymol. 266:131-141; Altschul, S. F. et al. (1997) Nucleic Acids Res. 25:3389-3402; Zhang, J. & Madden, T. L. (1997) Genome Res. 7:649-656). Sequence identity can be determined, for example, by comparing two sequences using the blast2 sequences program to prepare an alignment of the two sequences (Tatiana A et al. (1999) FEMS Microbiol Lett. 174:247-250). Gaps are treated in the same way as mismatches. For example, an identity score is calculated in view of the entire nucleotide sequences of SEQ ID NOs: 1 and 2. Specifically, the ratio of the number of identical nucleotides in the alignment to the total number of nucleotides of SEQ ID NO: 1 or 2 is calculated. Gaps outside of SEQ ID NO: 1 or 2 in the alignment is excluded from the calculation.

The CMV enhancer sequence and chicken β-actin promoter sequence can also be isolated by hybridization from the nucleic acid of a CMV genome and chicken genomic DNA, respectively. The CMV enhancer and chicken β-actin promoter used in the present invention may be DNAs that have an equivalent promoter activity and hybridize under stringent conditions to the nucleotide sequences of SEQ ID NOs: 1 and 2, respectively, or to the complementary sequences thereof. When hybridization is used, such a promoter can be identified, for example, by preparing a probe either from the nucleotide sequence of SEQ ID NO: 1 or 2 or the complementary sequence thereof, or from a DNA to be hybridized, and then detecting whether the probe hybridizes to the other DNA. Stringent hybridization conditions are, for example, hybridization at 60° C., preferably at 65° C., more preferably at 68° C. in a solution containing 5×SSC, 7% (W/V) SDS, 100 µg/ml denatured salmon sperm DNA, and 5×Denhardt's solution (1×Denhardt's solution contains 0.2% polyvinylpyrrolidone, 0.2% bovine serum albumin, and 0.2% Ficoll); and washing twice at the same temperature as the hybridization while shaking in 2×SSC, preferably 1×SSC, more preferably 0.5×SSC, still more preferably 0.1×SSC.

In one embodiment of the present invention, the method for producing minus-strand RNA viruses is a method for transcribing in virus-producing cells, a DNA that encodes a ribozyme and minus-strand RNA virus genome RNA or the complementary strand thereof, and which is operably linked to CA promoter. An early transcript from this DNA comprises the ribozyme and the minus-strand RNA virus genome RNA (a plus or minus strand). The ribozyme is designed to have an activity of cleaving between the ribozyme and the minus-strand RNA virus genome RNA. Acting either in cis or trans, the ribozyme in the RNA transcript cleaves the RNA between the ribozyme and the minus-strand RNA virus genome RNA, and thereby generates minus-strand RNA virus genome RNA with precise genome ends (Inoue, K. et al. J. Virol. Methods 107, 2003, 229-236). In the ribozyme-based method, the minus-strand RNA virus genome RNA with precise ends is self-generated simply by transcribing DNA into RNA. Thus, the method is superior since it simplifies virus production methods and requires no special cells.

Ribozymes that cleave particular sequences can be designed using known techniques. For example, hammerhead ribozymes have been isolated from viroid and such in nature (J. M. Buzayan et al., Nature, 1986, 323: 349-353; GA. Prody et al., Science, 1986, 231:1577-1580), and they originally have a hammer structure with three loops and three helices and act in cis. They can also act in trans when the target RNA is separated from the RNA region that has the catalytic activity. For example, such ribozymes have a loop and a helix and form a quasi-loop with the target sequence (Turner, P. C., The Biochemistry of the Hammerhead Ribozyme. In: Scanlon, K J., and Kashani-Sabet, M. ed. Ribozymes in the Gene Therapy of Cancer (Medical Intelligence UNIT4), R. G. Landes Company, 1998; 3-14). The hammerhead ribozyme is a structurally well-known ribozyme. The ribozyme of tobacco ringspot virus specifically cleaves at the 3' side of the nucleotide sequence NUH (N=A, G, C, or U; H=A, C, or U) (M. Koizumi et al., FEBS Lett. 228:225, 1988). Thus, it is possible to create a ribozyme that specifically cleaves a desired target RNA at a site comprising the sequence UC, UU, or UA (M. Koizumi et al., FEBS Lett. 239:285, 1988; M. Koizumi and E. Otsuka, Tampakushitsu Kakusan Kouso (Protein, Nucleic acid and Enzyme), 35: 2191, 1990; M. Koizumi et al., Nucleic Acids Res. 17:7059, 1989).

Hairpin ribozymes are also useful for the purpose of the present invention. For example, hairpin ribozymes are found in the minus strand of satellite RNA in tobacco ringspot viruses (J. M. Buzayan, Nature 323:349, 1986). It has been demonstrated that this ribozyme can also be designed to cleave RNA in a target specific manner (Y. Kikuchi and N. Sasaki, Nucleic Acids Res. 19:6751, 1992; Y Kikuchi, Kagaku To Seibutsu (Chemistry and Biology) 30:112, 1992).

The ribozymes described above can be appropriately modified. A method that prepares modified ribozymes with higher activity by using an in vitro evolution system to modify natural ribozymes is known (Joyce. 1992. Selective Amplification Techniques for Optimization of Ribozyme Function, in Antisense RNA and DNA, pp. 353-372. Wiley-Liss Inc.). Ribozymes that function as a dimer can also be used.

In general, a ribozyme with RNA cleavage activity contains a sequence essential for the catalytic activity and a target recognition sequence required for target RNA recognition. Sequences required for hammerhead ribozyme catalysis include, but are not limited to, for example, 5'-$^{1}C^{2}U^{3}G^{4}A^{5}N^{6}G^{7}A^{8}N^{9}N^{10}N^{11}N^{12}N^{13}N^{14}N^{15}N^{16}N^{17}N^{18}N^{19}N^{20}G^{21}A^{22}A^{23}A^{24}N$-3' (SEQ ID NO: 5). In the above sequence, N represents G; A, U, or C; and 5'-$^{8}N^{9}N^{10}N^{11}N$-3' and 5'-$^{16}N^{17}N^{18}N^{19}N$-3' are designed to be complementary to each other to allow base pair formation. For example, 5'-$^{8}N^{9}N^{10}N^{11}N$-3' includes, but is not limited to, 5'-GUCC-3'; and 5'-$^{16}N^{17}N^{18}N^{19}N$-3' includes, but is not limited to, 5'-GGAC-3'. The four nucleotides $^{12}N^{13}N^{14}N^{15}N$ preferably form a loop. They may be about 2 to 7 nucleotides (i.e., $N_{2-7}$), for example, about 3 to 5 nucleotides (i.e., $N_{3-5}$) rather than four nucleotides. $^{23}A^{24}N$ overlaps with the target recognition sequence. $^{24}N$ is a nucleotide complementary to N in the target site "NUH" described above. An example is 5'-GUGA-3'. More specific sequences are shown in the Examples. The target recognition sequence is added to both ends. The target recognition sequence is designed to be complementary to the sequence between the ribozyme and the minus-strand RNA viral genome.

Another embodiment of the method of the present invention is a method which comprises expressing, in virus-producing cells, a bacteriophage RNA polymerase-encoding DNA operably linked to a CA promoter. The virus-producing cells are made to contain a DNA that encodes minus-strand RNA virus genome RNA or the complementary strand thereof, which is linked downstream of an RNA polymerase recognition sequence. The expressed RNA polymerase transcribes the minus-strand RNA virus genome RNA-encoding DNA, which is linked downstream of the RNA polymerase recognition sequence, to generate viral genome RNA. The RNA polymerases used include desired bacteriophage-derived RNA polymerases that recognize specific sequences (i.e., target sequences for the RNA polymerases; generally also referred to as "promoter sequences") and initiate the transcription, and specifically include those of *E. coli* T3 phage and T7 phage, and *Salmonella* SP6 phage (Krieg, P. A. and Melton, D. A. 1987. In vitro RNA synthesis with SP6 RNA polymerase. Methods Enzymol. 155: 397-15; Milligan, J. F., Groebe, D. R., Witherell, G. W., and Uhlenbeck, O. C. 1987. Oligoribonucleotide synthesis using T7 RNA polymerase and synthetic DNA templates. Nucleic Acids Res. 15: 8783-798; Pokrovskaya, I. D. and Gurevich, V. V. 1994. In vitro transcription: Preparative RNA yields in analytical scale reactions. Anal. Biochem. 220: 420-23).

Typical recognition sequences (promoter sequences) for T3, T7, and SP6 are shown below. "+1" indicates the first nucleotide to be transcribed.

```
                         +1
T7:    TAATACGACTCACTATAGGGAGA     (SEQ ID NO: 6)

T3:    AATTAACCCTCACTAAAGGGAGA     (SEQ ID NO: 7)

SP6:   ATTTAGGTGACACTATAGAAGNG     (SEQ ID NO: 8)
(N = A, G, C, or T)
```

The region from −17 to −1 is essential for the transcription and must be double-stranded. To achieve efficient transcription, it is important that the first two of nucleotides +1 to +6 shown above (+1 and +2) is GP (P=purine (A or G)). The other nucleotides may be substituted with different nucleotides. The underlined sequences shown above are preferably used. The cDNA of a minus-strand RNA virus genome (a plus or minus strand) is linked immediately downstream of the above-described recognition sequences for the RNA polymerases. Production of high efficiency viruses may be achieved by transcribing the plus strand.

The transcription vector for the minus-strand RNA virus genome and the expression vectors for the phage RNA polymerases described above may be desired DNA vectors or vectors that are converted into DNA after being introduced into cells, such as retroviruses. Typically, plasmid vectors are used. The vector may be an expression vector which exists as an episome in cells after introduction or as a chromosome-integrated vector which is expressed after being integrated into chromosomes in cells. For example, when a plasmid is used, it may be transiently expressed by transfection, or stable transformants in which the plasmid is integrated into their chromosomes may be selected. In particular, cell lines stably expressing a phage RNA polymerase are useful, because they simplify the procedure of virus production and allow stable production of high-titer virus (see Example 2). The vector may be a constitutive expression vector or an inducible expression vector whose expression can be induced when needed. For example, the vector can be inducibly expressed using a sequence-specific recombinase (recombination enzyme) (Example 2). The type of recombinase that can be used for this purpose includes Cre recombinase and FLP recombinase. The expression can be induced in response to a recombinase by inserting a DNA flanked by target sequences for the recombinase between a CA promoter and the coding sequence of a ribozyme or an RNA polymerase.

Cre is an approximately 38 kDa cyclization recombinase carried by bacteriophage P1 and performs site-specific DNA recombination between loxP sites (Sauer B, Henderson N. 1988. Site-specific DNA recombination in mammalian cells by the Cre recombinase of bacteriophage P1. Proc Natl Acad Sci USA 85:5166-70; Sternberg N, Hamilton D. 1981. Bacteriophage P1 site-specific recombination. I. Recombination between loxP sites. J Mol Biol 150:467-86; Brian Sauer, Methods of Enzymology; 1993, Vol. 225, 890-900; Nagy A. 2000. Cre recombinase: the universal reagent for genome tailoring. Genesis 26:99-109). loxP is a 13-bp asymmetric inverted repeat sequence which comprises an 8-bp spacer ( ATAACTTCGTATAATGTATGCTATACGAAGTTAT; the underlines indicate the inverted repeats; SEQ ID NO: 9).

FLP recombinase is a flippase recombinase of about 49 kDa derived from the 2 micron plasmid of yeast *Saccharomyces cerevisiae* and targets the FLP recombinase target (FRT) sequence for recombination (Utomo A R, Nikitin A Y, Lee W H. 1999. Temporal, spatial, and cell type-specific control of Cre-mediated DNA recombination in transgenic mice. Nat Biotechnol 17:1091-6; Broach, J. R., Guarascio, V. R. & Jayaram, M. (1982) Cell 29, 227-34; Cox, M. M. (1983) Proc. Natl. Acad. Sci. USA 80, 4223-227; Vetter, D., Andrews, B. J., Roberts-Beatty, L. & Sadowski, P. D. (1983) Proc. Natl. Acad. Sci. USA 80, 7284-288; Abremski, K. & Hoess, R. (1984) J. Biol. Chem. 259, 1509-514; Stark, W. M., Boocock, M. R. & Sherratt, D. J. (1992) Trends Genet. 8, 432-39; Kilby, N. J., Snaith, M. R. & Murray, J. A. H. (1993) Trends Genet. 9, 413-21). Like loxP, FRT sequences also consist of a 13-bp repeat sequence comprising an 8-bp spacer (GAAGTTCCTATTCTCTAGAAAGTATAGGAACTTC; SEQ ID NO: 10) (Andrews, B. J. et al. (1985). The FLP Recombinase of the 2 Micron Circle DNA of Yeast: Interaction with its Target Sequences. Cell 40, 795-803). In addition, target-specific recombination can be achieved using mutant sequences of the loxP site and FRT site described above (Baszczynski, Christopher L. et al, US Patent Application 20040003435).

To construct DNA whose expression can be induced by a recombinase, DNA flanked by a pair of recombinase target sequences is inserted between a CA promoter and the coding sequence of a ribozyme or a phage RNA polymerase. In this state, due to interference by the inserted DNA fragment, the minus-strand RNA virus genome (to which the ribozyme is attached) or the phage RNA polymerase is not expressed from the CA promoter. However, when the recombinase acts on the DNA, the target sequence-flanked DNA is excised, which enables the minus-strand RNA virus genome or the phage RNA polymerase to be expressed from the CA promoter. As described above, expression from the CA promoter can be induced by a recombinase. The DNA flanked by the recombinase target sequences is preferably designed to contain a transcription termination signal and/or stop codon so that the expression of the downstream minus-strand RNA virus genome or phage RNA polymerase gene is certainly blocked in the absence of the recombinase action. An appropriate marker gene can also be inserted into the DNA flanked by the recombinase target sequences.

The DNAs and cells for producing viruses, which are described herein, can be appropriately combined into a kit for producing viruses. For example, the present invention relates to the following kits:

(1-1) a kit for producing a minus-strand RNA virus, which comprises: a bacteriophage RNA polymerase-encoding DNA operably linked to a CA promoter; and a DNA encoding the minus-strand RNA virus genome RNA or the complementary strand thereof and which is operably linked to the RNA polymerase recognition sequence;

(1-2) the kit of (1-1), which further comprises a DNA encoding minus-strand RNA viral proteins that form RNP with the genome RNA, wherein the DNA is operably linked to a CA promoter;

(1-3) the kit of (1-1) or (1-2), in which the genome RNA or the complementary strand thereof lacks one or more genes that encode an envelope-constituting protein;

(1-4) the kit of any one of (1-1) to (1-3), which further comprises a DNA encoding an envelope-constituting protein;

(1-5) the kit of any one of (1-1) to (1-4), in which the DNA that encodes an envelope-constituting protein is operably linked to a CA promoter;

(1-6) the kit of any one of (1-1) to (1-5), in which the minus-strand RNA virus is Sendai virus;

(1-7) the kit of any one of (1-1) to (1-6), in which the bacteriophage is selected from the group consisting of SP6 phage, T3 phage, and T7 phage;

(1-8) the kit of any one of (1-1) to (1-7), in which the expression of the RNA polymerase can be induced by a recombinase;

(1-9) the kit of (1-8), in which the recombinase is Cre or Flp;

(2-1) a kit for producing a minus-strand RNA virus, which comprises: a mammalian cell carrying a bacteriophage RNA polymerase-encoding DNA operably linked to a CA promoter; and a DNA encoding the minus-strand RNA virus genome RNA or the complementary strand thereof, and which is operably linked to the RNA polymerase recognition sequence;

(2-2) the kit of (2-1) which further comprises a DNA encoding minus-strand RNA viral proteins that form RNP with the genome RNA and, which is operably linked to a CA promoter;

(2-3) the kit of (2-1) or (2-2), in which the genome RNA or the complementary strand thereof lacks one or more genes that encode an envelope-constituting protein;

(2-4) the kit of any one of (2-1) to (2-3), which further comprises a DNA encoding an envelope-constituting protein;

(2-5) the kit of any one of (2-1) to (2-4), in which the DNA that encodes an envelope-constituting protein is operably linked to a CA promoter;

(2-6) the kit of any one of (2-1) to (2-5), in which the minus-strand RNA virus is Sendai virus;

(2-7) the kit of any one of (2-1) to (2-6), in which the bacteriophage is selected from the group consisting of SP6 phage, T3 phage, and T7 phage;

(2-8) the kit of any one of (2-1) to (2-7), in which the expression of the RNA polymerase can be induced by a recombinase;

(2-9) the kit of (2-8), in which the recombinase is Cre or Flp;
(3-1) a kit for producing a minus-strand RNA virus, which comprises:
(i) a DNA encoding a ribozyme and the minus-strand RNA virus genome RNA or the complementary strand thereof and which is operably linked to a CA promoter, wherein the ribozyme has the activity of cleaving a transcript between the ribozyme and the minus-strand RNA virus genome RNA or the complementary strand thereof; and
(ii) a DNA encoding minus-strand RNA viral proteins that form RNP with the genome RNA and which is operably linked to a CA promoter.
(3-2) the kit of (3-1), in which the genome RNA or the complementary strand thereof lacks one or more genes that encode an envelope-constituting protein;
(3-3) the kit of (3-1) or (3-2) which further comprises a DNA encoding an envelope-constituting protein;
(3-4) the kit of any one of (3-1) to (3-3), in which the DNA that encodes an envelope-constituting protein is operatively linked to a CA promoter;
(3-5) the kit of any one of (3-1) to (3-4), in which the minus-strand RNA virus is Sendai virus;
(3-6) the kit of any one of (3-1) to (3-5), in which the bacteriophage is selected from the group consisting of SP6 phage, T3 phage, and T7 phage;
(3-7) the kit of any one of (3-1) to (3-6), in which the expression of the DNA of (i) and/or (ii) can be induced by a recombinase; and
(3-8) the kit of (3-7), in which the recombinase is Cre or Flp.

The phrase "the expression can be induced by a recombinase" means that a DNA flanked by recombinase recognition sequences is inserted between a CA promoter and the downstream DNA, so that the expression of the DNA downstream of the CA promoter is induced upon removal of the DNA flanked by recombinase recognition sequences.

Herein, a minus-strand RNA virus refers to viruses that contain a minus strand (an antisense strand complementary to a sense strand encoding viral proteins) RNA as the genome. The minus-strand RNA is also referred to as negative strand RNA. The minus-strand RNA virus used in the present invention particularly includes single-stranded minus-strand RNA viruses (also referred to as non-segmented minus-strand RNA viruses). The "single-strand negative strand RNA virus" refers to viruses having a single-stranded negative strand [i.e., a minus strand] RNA as the genome. Such viruses include viruses belonging to Paramyxoviridae (including the genera Paramyxovirus, Morbillivirus, Rubulavirus, and Pneumovirus), Rhabdoviridae (including the genera Vesiculovirus, Lyssavirus, and Ephemerovirus), Filoviridae, and the like.

In addition, the minus-strand RNA viral vector refers to a minus-strand RNA virus-based transmissible virus which serves as a vehicle for introducing genes into cells. Herein, "infectivity" refers to the capability of a minus-strand RNA viral vector to maintain cell-adhesion ability and introduce a gene carried by the vector to the inside of the cell to which the vector has adhered. The "gene" refers to any genetic material carried by the minus-strand RNA viral vector of the present invention, and is not limited to a foreign gene. In other words, the minus-strand RNA viral vector may or may not have a foreign gene. The method of the present invention can be applied to production of both transsmissible viral vectors and defective nontransmissible vectors. In particular, the method is advantageous in that defective nontransmissible vectors can be efficiently produced. "Transmissible" means that when a viral vector infects a host cell, the virus is replicated in the cell to produce infectious virions.

"Recombinant virus" refers to a virus produced through a recombinant polynucleotide, or an amplification product thereof. "Recombinant polynucleotide" refers to a polynucleotide in which nucleotides are not linked at one or both ends as in the natural condition. Specifically, a recombinant polynucleotide is a polynucleotide in which the linkage of the polynucleotide chain has been artificially modified (cleaved and/or linked). Recombinant polynucleotides can be produced by using gene recombination methods known in the art in combination with polynucleotide synthesis, nuclease treatment, ligase treatment, etc. A recombinant virus can be produced by expressing a polynucleotide encoding a viral genome constructed through gene manipulation and reconstructing the virus. For example, methods for reconstructing a virus from cDNA that encodes the viral genome are known (Y. Nagai, A. Kato, Microbiol. Immunol., 43, 613-624 (1999)).

In the present invention, "gene" refers to a genetic substance, a nucleic acid encoding a transcriptional unit. Genes may be RNAs or DNAs. In this invention, a nucleic acid encoding a protein is referred to as a gene of that protein. Further, in general, a gene may not encode a protein. For example, a gene may encode a functional RNA, such as a ribozyme or antisense RNA. Generally, a gene may be a naturally-occurring or artificially designed sequence. Furthermore, in the present invention, "DNA" includes both single-stranded and double-stranded DNAs. Moreover, "encoding a protein" means that a polynucleotide includes an ORF that encodes an amino acid sequence of the protein in a sense or antisense direction, so that the protein can be expressed under appropriate conditions.

A minus-strand RNA virus particularly preferably used in the context of the present invention includes, for example, Sendai virus, Newcastle disease virus, mumps virus, measles virus, respiratory syncytial virus (RS virus), rinderpest virus, distemper virus, simian parainfluenza virus (SV5), and human parainfluenza viruses 1, 2, and 3 belonging to Paramyxoviridae; influenza virus belonging to Orthomyxoviridae; and vesicular stomatitis virus and rabies virus belonging to Rhabdoviridae.

Further examples of virus that may be used in the context of the present invention include those selected from the group consisting of: Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), Nipah virus (Nipah), human parainfluenza virus-2 (HPIV-2), simian parainfluenza virus 5 (SV5), human parainfluenza virus-4a (HPIV-4a), human parainfluenza virus-4b (HPIV-4b), mumps virus (Mumps), and Newcastle disease virus (NDV). A more preferred example is a virus selected from the group consisting of Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), and Nipah virus (Nipah).

More preferably, minus-strand RNA viruses produced in the present invention are preferably those belonging to Paramyxoviridae (including Respirovirus, Rubulavirus, and Morbillivirus) or derivatives thereof, and more preferably those belonging to the genus Respirovirus (also referred to as Paramyxovirus) or derivatives thereof. The derivatives include viruses that are genetically-modified or chemically-modified in a manner not to impair their gene-transferring ability. Examples of viruses of the genus Respirovirus applicable to this invention are human parainfluenza virus-1 (HPIV-1), human parainfluenza virus-3 (HPIV-3), bovine parainfluenza virus-3 (BPIV-3), Sendai virus (also referred to as murine parainfluenza virus-1), and simian parainfluenza virus-10 (SPIV-10). A more preferred paramyxovirus in this invention is the Sendai virus. These viruses may be derived from natural strains, wild strains, mutant strains, laboratory-passaged strains, artificially constructed strains, or the like.

Genes harbored on a minus-strand RNA viral vector are situated in the antisense direction in the viral genomic RNA. Viral genomic RNA refers to RNA that has the function to form a ribonucleoprotein (RNP) with the viral proteins of a minus-strand RNA virus. Genes contained in the genome are expressed by the RNP, genomic RNA is replicated, and daughter RNPs are formed. In general, in the minus-strand RNA viral genome, viral genes are arranged as antisense sequences between the 3'-leader region and the 5'-trailer region. Between the ORFs of respective genes are a transcription ending sequence (E sequence)—intervening sequence (I sequence)—transcription starting sequence (S sequence), such that RNA encoding the ORF of each gene is transcribed as an individual cistron. Genomic RNAs in a virus of this invention comprise the antisense RNA sequences encoding N (nucleocapsid)-, P (phospho)-, and L (large)-proteins, which are viral proteins essential for the expression of the group of genes encoded by an RNA, and for the autonomous replication of the RNA itself. The RNAs may encode M (matrix) proteins, which is essential for virion formation. Further, the RNAs may encode envelope proteins essential for virion infection. Minus-strand RNA viral envelope proteins include F (fusion) protein that causes cell membrane fusion, and HN (hemagglutinin-neuraminidase) protein which is essential for viral adhesion to cells. However, HN protein is not required for the infection of certain types of cells (Markwell, M. A. et al., Proc. Natl. Acad. Sci. USA 82(4): 978-982 (1985)), and infection is achieved with F protein only. The RNAs may encode envelope proteins other than F protein and/or HN protein.

Genes of Paramyxovirinae viruses are commonly listed as follows. In general, NP gene is also listed as "N gene." HN that does not have a neuraminidase activity is listed as "H".

| Respirovirus | NP | P/C/V | M | F | HN | — | L |
| Rubulavirus | NP | P/V | M | F | HN | (SH) | L |
| Morbillivirus | NP | P/C/V | M | F | H | — | L |

For example, the database accession numbers for the nucleotide sequences of each of the Sendai virus genes are: M29343, M30202, M30203, M30204, M51331, M55565, M69046, and X17218 for NP gene; M30202, M30203, M30204, M55565, M69046, X00583, X17007, and X17008 for P gene; D11446, K02742, M30202, M30203, M30204, M69046, U31956, X00584, and X53056 for M gene; D00152, D11446, D17334, D17335, M30202, M30203, M30204, M69046, X00152, and X02131 for F gene; D26475, M12397, M30202, M30203, M30204, M69046, X00586, X02808, and X56131 for HN gene; and D00053, M30202, M30203, M30204, M69040, X00587, and X58886 for L gene. Examples of viral genes encoded by other viruses are: CDV, AF014953; DMV, X75961; HPIV-1, D01070; HPIV-2, M55320; HPIV-3, D10025; Mapuera, X85128; Mumps, D86172; MV, K01711; NDV, AF064091; PDPR, X74443; PDV, X75717; RPV, X68311; SeV, X00087; SV5, M81442; and Tupaia, AF079780 for N gene; CDV, X51869; DMV, Z47758; HPIV-1, M74081; HPIV-3, X04721; HPIV-4a, M55975; HPIV-4b, M55976; Mumps, D86173; MV, M89920; NDV, M20302; PDV, X75960; RPV, X68311; SeV, M30202; SV5, AF052755; and Tupaia, AF079780 for P gene; CDV, AF014953; DMV, Z47758; HPIV-1, M74081; HPIV-3, D00047; MV, ABO16162; RPV, X68311; SeV, AB005796; and Tupaia, AF079780 for C gene; CDV, M12669; DMV, Z30087; HPIV-1, S38067; HPIV-2, M62734; HPIV-3, D00130; HPIV-4a, D10241; HPIV-4b, D10242; Mumps, D86171; MV, AB012948; NDV, AF089819; PDPR, Z47977; PDV, X75717; RPV, M34018; SeV, U31956; and SV5, M32248 for M gene; CDV, M21849; DMV, AJ224704; HPN-1, M22347; HPIV-2, M60182; HPIV-3, X05303; HPIV-4a, D49821; HPIV-4b, D49822; Mumps, D86169; MV, AB003178; NDV, AF048763; PDPR, Z37017; PDV, AJ224706; RPV, M21514; SeV, D17334; and SV5, AB021962 for F gene; and, CDV, AF112189; DMV, AJ224705; HPIV-1, U709498; HPIV-2, D000865; HPIV-3, AB012132; HPIV-4A, M34033; HPIV-4B, AB006954; Mumps, X99040; MV, K01711; NDV, AF204872; PDPR, Z81358; PDV, Z36979; RPV, AF132934; SeV, U06433; and SV-5, S76876 for HN (H or G) gene. However, multiple strains are known for each virus, and there exist genes that comprise sequences other than those cited above as a result of strain variation.

ORFs encoding these viral proteins and ORFs of foreign genes are arranged in the antisense direction in the genomic RNA via the above-described E-I-S sequence. The ORF closest to the 3'-end of the genomic RNA requires only an S sequence between the 3'-leader region and the ORF, and does not require an E or I sequence. Further, the ORF closest to the 5'-end of the genomic RNA requires only an E sequence between the 5'-trailer region and the ORF, and does not require an I or S sequence. Furthermore, two ORFs can be transcribed as a single cistron, for example, by using an internal ribosome entry site (IRES) sequence. In such a case, an E-I-S sequence is not required between these two ORFs. For example, in wild type paramyxoviruses, a typical RNA genome includes a 3'-leader region, six ORFs encoding the N, P, M, F, HN, and L proteins in the antisense direction in this order, and a 5'-trailer region on the other end. The orientation of the viral gene in the genomic RNAs of the present invention is not restricted, but similarly to the wild type viruses, it is preferable that ORFs encoding the N, P, M, F, HN, and L proteins are arranged after the 3'-leader region and before the 5'-trailer region. Certain types of viruses have different viral genes, but even in such cases, it is preferable that each gene be arranged as in the wild type, as described above. In general, vectors maintaining the N, P, and L genes can autonomously express genes from the RNA genome in cells and the genomic RNA is replicated. Furthermore, by the action of genes such as the F and HN genes which encode envelope spike proteins and the M gene, infectious virions are formed and released to the outside of the cells. Thus, such vectors become transmissible viral vectors. When the vectors carry a foreign gene, the gene may be inserted into a non-protein-coding region in this genome, as described below.

Alternatively, the minus-strand RNA viral vector may lack any of the wild type viral genes. For example, viruses that lack genes encoding viral envelope-constituting proteins are useful as high safety gene transfer vectors. According to the method of the present invention, high-titer viruses lacking genes encoding viral envelope-constituting proteins can be harvested without using a vaccinia virus vector. The "envelope-constituting proteins" refers to viral proteins that serve as viral envelope components, which include spike proteins that are exposed on an envelope surface and function in cell adhesion or infection, and lining proteins which function in envelope formation and such. Specifically, genes that encode envelope-constituting proteins include F, HN, and M; and also include genes of H, M1, and G in some viral species. Viruses that lack one or more genes that encode these envelope-constituting proteins are highly safe, because they cannot form infectious viral particles in infected cells. Such viruses can be reconstituted, for example, by exogenously supplying the gene products that are deficient in the viruses. Alternatively, the viral infectivity can be complemented by completely different envelope proteins. Such envelope proteins include, for example, VSV-G. Thus, envelope protein genes to be used for constructing viruses that are deficient in envelope-constituting protein genes are not limited to the deleted genes, as long as they ensure viral formation and infectivity. Similar to wild type viruses, the viruses thus prepared adhere to host cells and cause cell fusion, but they cannot form daughter virions that retain the same infectivity as the original vector, because the viral genome introduced into cells is deficient in viral genes. Therefore, such vectors are useful as safe viral vectors that can only introduce genes once (WO00/70055, WO00/70070, and WO03/025570; Li, H.-O. et al., J. Virol. 74(14) 6564-6569 (2000)). Examples of genes in which the genome may be deficient are the F gene, HN gene, M gene, or any combination thereof. For example, recombinant viruses can be reconstituted by transfecting host cells with a plasmid expressing a recombinant minus-strand RNA viral genome deficient in the F gene, along with an F protein expression vector and expression vectors for the NP, P, and L proteins (see Examples 4 and 5). Viruses can also be produced, for example, using host cells that have incorporated the F gene into their chromosomes. In this case, the recombinant enzyme target sequence described above is preferably used to allow the induction of recombinant enzyme-specific expression so that the F gene can be inducibly expressed. These proteins, which are expressed in virus-producing cells, do not need to have the same amino acid sequences as the viral sequences, and a mutant or homologous gene from another virus may be used as a substitute, so long as the activity in nucleic acid introduction is the same as, or greater than, that of the natural type.

Further, in the present invention, recombinant viruses that include an envelope protein other than that of the virus from which the viral genome was derived, may be produced as described above. For example, when reconstituting a virus, a recombinant virus including a desired envelope protein can be generated by expressing an envelope protein other than the envelope protein originally encoded by the basic viral genome. Such proteins are not particularly limited. A desired protein that confers an ability to infect cells may be used. Examples of such proteins include the envelope proteins of other viruses, for example, the G protein of vesicular stomatitis virus (VSV-G). The VSV-G protein may be derived from an arbitrary VSV strain. For example, VSV-G proteins derived from Indiana serotype strains (J. Virology 39: 519-528 (1981)) may be used, but the present invention is not limited thereto. Furthermore, the present vector may include any arbitrary combination of envelope proteins derived from other viruses. Preferred examples of such proteins are envelope proteins derived from viruses that infect human cells. Such proteins are not particularly limited, and include retroviral amphotropic envelope proteins and the like. For example, the envelope proteins derived from mouse leukemia virus (MuLV) 4070A strain can be used as the retroviral amphotropic envelope proteins. In addition, envelope proteins derived from MuMLV 10A1 strain may also be used (for example, pCL-10A1 (Imgenex) (Naviaux, R. K. et al., J. Virol. 70:5701-5705 (1996)). The proteins of Herpesviridae include, for example, gB, gD, gH, and gp85 proteins of herpes simplex viruses, and gp350 and gp220 proteins of EB virus. The proteins of Hepadnaviridae include the S protein of hepatitis B virus. These proteins may be used as fusion proteins in which the extracellular domain is linked to the intracellular domain of the F or HN protein. As described above, the viral vectors used in this invention include pseudotype viral vectors that include envelope proteins, such as VSV-G, derived from viruses other than the virus from which the genome was derived. If the viral vectors are designed such that these envelope proteins are not encoded in RNA genomes, the proteins will never be expressed after virion infection of the cells.

Alternatively, in the present invention, for example, it is possible to produce viruses that have on their envelope surface, a chimeric protein or such which comprises: a protein that can adhere to a particular cell, such as an adhesion factor, ligand, or receptor, antibody or a fragment thereof, or these proteins in the extracellular region; and a polypeptide derived from a minus-strand RNA virus envelope protein in the cytoplasmic region. Therefore, the infection specificity of a viral vector can be controlled. Such proteins may be encoded by the viral genome, or supplied through the expression of genes other than the viral genome (for example, genes in other expression vectors or host chromosomes) during viral reconstitution.

Further, in the viral vectors, any viral gene contained in the virus may be modified from the wild type gene in order to reduce the immunogenicity caused by viral proteins, or to enhance RNA transcriptional or replicational efficiency, for example. Specifically, for example, modifying at least one of the replication factors N, P, and L genes, is considered to enhance transcriptional or replicational function. Furthermore, although the HN protein, which is an envelope protein, has both hemagglutinin activity and neuraminidase activity, it is possible, for example, to improve viral stability in blood if the former activity is attenuated, and infectivity can be controlled if the latter activity is modified. Further, it is also possible to control membrane fusion ability by modifying the F protein. For example, the epitopes of the F protein and/or HN protein, which can be cell surface antigenic molecules, can be analyzed, and using this, recombinant viral vectors with reduced antigenicity to these proteins can be prepared.

Furthermore, the minus-strand RNA viral vector may be deficient in one or more accessory genes. For example, by knocking out the V gene, one of the SeV accessory genes, the pathogenicity of SeV toward hosts such as mice is remarkably reduced, without hindering gene expression and replication in cultured cells (Kato, A. et al., 1997, J. Virol. 71: 7266-7272; Kato, A. et al., 1997, EMBO J. 16: 578-587; Curran, J. et al., WO01/04272, EP1067179). Such attenuated vectors are particularly useful as nontoxic viral vectors for in vivo or ex vivo gene transfer.

Minus-strand RNA viruses are excellent gene transfer vectors. They do not have DNA phase and carry out transcription and replication only in the host cytoplasm, and consequently, chromosomal integration does not occur (Lamb, R. A. and Kolakofsky, D., Paramyxoviridae: The viruses and their replication. In: Fields B N, Knipe D M, Howley P M, (eds). Fields of Virology. Vol. 2. Lippincott—Raven Publishers: Philadelphia, 1996, pp. 1177-1204). Therefore, safety issues such as transformation and immortalization due to chromosomal abberation do not occur. This characteristic of minus-strand RNA viruses contributes greatly to safety when it is used as a vector. For example, results on foreign gene expression show that even after multiple continuous passages of SeV, almost no nucleotide mutation is observed. This suggests that the viral genome is highly stable and the inserted foreign genes are stably expressed over long periods of time (Yu, D. et al., Genes Cells 2, 457-466 (1997)). Further, there are qualitative advantages associated with SeV not having a capsid structural protein, such as packaging flexibility and insert gene size, suggesting that minus-strand RNA viral vectors may become a novel class of highly efficient vectors for human gene therapy. Transmissible SeV vectors are capable of introducing foreign genes of up to at least 5 kb in size, and can simultaneously express two or more kinds of genes by adding the transcriptional units.

In particular, SeV is known to be pathogenic in rodents causing pneumonia, but is not pathogenic for human. This is also supported by a previous report that nasal administration of wild type SeV does not have severely harmful effects on non-human primates (Hurwitz, J. L. et al., Vaccine 15: 533-540, 1997; Bitzer, M. et al., J. Gene Med. 5: 543-553, 2003; Slobod, K. S. et al., Vaccine 22: 3182-3186, 2004). These SeV characteristics suggest that SeV vectors can be applied therapeutically on humans.

Viral vectors of this invention can encode desired foreign genes in their genomic RNA. A recombinant viral vector harboring a foreign gene is obtained by inserting a foreign gene into an above-described viral vector genome. The foreign gene can be inserted at any desired position in a non-protein-coding region of the virus genome, for example. The above nucleic acid can be inserted, for example, between the 3'-leader region and the viral protein ORF closest to the 3'-end; between each of the viral protein ORFs; and/or between the viral protein ORF closest to the 5'-end and the 5'-trailer region in genomic DNA. Further, in genomes deficient in envelope proteins such as M, F, or HN gene, nucleic acids encoding foreign genes can be inserted into those deficient regions. When introducing a foreign gene into a paramyxovirus, it is desirable to insert the gene such that the chain length of the polynucleotide to be inserted into the genome will be a multiple of six (Journal of Virology, Vol. 67, No. 8, 4822-4830, 1993). An E-I-S sequence should be arranged between the inserted foreign gene and the viral ORF. Two or more foreign genes can be inserted in tandem via E-I-S sequences.

A cloning site for inserting a foreign gene can be designed in a genome RNA-encoding cDNA so that the foreign gene can be readily inserted into the cDNA. The site may be placed, for example, at a desired position within the noncoding region of the genome. Specifically, such a gene can be inserted between the 3'-leader region and the viral protein ORF proximal to 3', between respective viral protein ORFs, and/or between the viral protein ORF proximal to 5' and the 5'-trailer region. When the genome lacks genes encoding an envelope-constituting protein, the cloning site can be designed to be in the region where the genes have been deleted. The cloning site may be, for example, a restriction enzyme recognition sequence. The cloning site may be a so-called multi-cloning site, which has multiple restriction enzyme recognition sequences. Cloning sites may be placed at multiple positions in the genome so that multiple foreign genes can be inserted at different positions in the genome.

Expression levels of a foreign gene carried in a vector can be controlled using the type of transcriptional initiation sequence added upstream (to the 3'-side of the minus strand (negative strand)) of the gene (WO01/18223). The expression levels can also be controlled by the position at which the foreign gene is inserted in the genome: the nearer to the 3'-end of the minus strand the insertion position is, the higher the expression level; while the nearer to the 5'-end the insertion position is, the lower the expression level. Thus, to obtain a desired gene expression level, the insertion position of a foreign gene can be appropriately controlled such that the combination with genes encoding the viral proteins before and after the foreign gene is most suitable. In general, since a high foreign gene expression level is thought to be advantageous, it is preferable to link the foreign gene to a highly efficient transcriptional initiation sequence, and to insert it near the 3'-end of the minus strand genome. Specifically, a foreign gene is inserted between the 3'-leader region and the viral protein ORF closest to the 3'-end. Alternatively, a foreign gene may be inserted between the ORFs of the viral protein gene closest to the 3'-end and the second closest viral protein gene, or between the ORFs of the second and third closest viral protein genes. In wild type paramyxoviruses, the viral protein gene closest to the 3'-end of the genome is the N gene, the second closest gene is the P gene, and the third closest gene is M gene. Alternatively, when a high level of expression of the introduced gene is undesirable, the gene expression level from the viral vector can be suppressed to obtain an appropriate effect, for example, by inserting the foreign gene at a site as close as possible to the 5'-side of the minus strand genome, or by selecting an inefficient transcriptional initiation sequence.

For example, a desired S sequence of a minus-strand RNA virus may be used as the S sequence to be attached when inserting a foreign gene-encoding nucleic acid into the genome. The sequence 3'-UCCCWVUUWC-5' (W=A or C; V=A, C, or G)(SEQ ID NO: 11) can be preferably used for Sendai viruses. Particularly preferred sequences are 3'-UCCCAGUUUC-5' (SEQ ID NO: 12), 3'-UCCCACUUAC-5' (SEQ ID NO: 13), and 3'-UCCCACUUUC-5' (SEQ ID NO: 14). When shown as plus strand-encoding DNA sequences, these sequences are 5'-AGGGTCAAAG-3' (SEQ ID NO: 15), 5'-AGGGTGAATG-3' (SEQ ID NO: 16), and 5'-AGGGTGAAAG-3' (SEQ ID NO: 17). A preferred E sequence of a Sendai viral vector is, for example, 3'-AUUCUUUUU-5' (SEQ ID NO: 18) or 5'-TAAGAAAAA-3' (SEQ ID NO: 19) for the plus strand-encoding DNA. An I sequence may be, for example, any three nucleotides, specifically 3'-GAA-5' (5'-CTT-3' in the plus strand DNA).

To prepare a minus-strand RNA viral vector, the expression of viral proteins (i.e., N, P, and L proteins) essential for reconstitution of an RNP including the genomic RNA of the minus-strand RNA virus and the transcription of a CDNA encoding a genomic RNA of a minus-strand RNA virus are induced by CA promoter. Viral RNP can be reconstituted by producing either the minus-strand genome (that is, the same antisense strand as the viral genome) or the plus strand (antigenome, the complementary strand of the genomic RNA). For increasing the efficiency of vector reconstitution, it is more preferable to produce the plus strand. The RNA terminals preferably reflect the terminals of the 3'-leader sequence and 5'-trailer sequence as accurately as possible, as in the natural viral genome. As described above, this is achieved by adding a self-cleaving ribozyme at the 5'-end of the transcript, to allow the ribozyme to accurately cleave off the end of the minus-strand RNA viral genome. In an alternative embodiment, to accurately regulate the 5'-end of the transcript, the RNA polymerase is expressed within a cell using the recognition sequence of bacteriophage RNA polymerase as a transcription initiation site.

To regulate the 3'-end of the transcript, for example, a self-cleaving ribozyme can be encoded at the 3'-end of the transcript, allowing accurate cleavage of the 3'-end with this ribozyme (Hasan, M. K. et al., J. Gen. Virol. 78: 2813-2820, 1997; Kato, A. et al., 1997, EMBO J. 16: 578-587; and Yu, D.

et al., 1997, Genes Cells 2: 457-466). An auto-cleaving ribozyme derived from the antigenomic strand of delta hepatitis virus can be used.

For example, a recombinant Sendai virus can be constructed as follows, according to the disclosure herein and descriptions in: Hasan, M. K. et al., J. Gen. Virol. 78: 2813-2820, 1997; Kato, A. et al., 1997, EMBO J. 16: 578-587; Yu, D. et al., 1997, Genes Cells 2: 457-466; or the like.

To incorporate a foreign gene, a DNA sample comprising a cDNA sequence of a foreign gene of interest is first prepared. The DNA sample is preferably one that can be confirmed to be a single plasmid by electrophoresis at a concentration of 25 ng/µl or more. The following explains a case using a Not I site to insert a foreign gene into a DNA encoding a viral genomic RNA, with reference to examples. When a Not I recognition site is included in a target cDNA nucleotide sequence, the base sequence is altered using site-directed mutagenesis or the like, such that the encoded amino acid sequence does not change, and the Not I site is preferably excised in advance. The gene fragment of interest is amplified from this sample by PCR, and then recovered. By adding the Not I site to the 5' regions of a pair of primers, both ends of the amplified fragments become Not I sites. E-I-S sequences are designed to be included in primers such that, after a foreign gene is inserted into the viral genome, one E-I-S sequence is placed between the foreign gene ORF and each side of the viral gene ORF. The length of the synthesized DNA is designed such that the chain length of the last fragment to be inserted, which contains the added E-I-S sequences, will become a multiple of six nucleotides (the so-called "rule of six"); Kolakofski, D., et al., J. Virol. 72:891-899, 1998; Calain, P. and Roux, L., J. Virol. 67:4822-4830, 1993; Calain, P. and Roux, L., J. Virol. 67: 4822-4830, 1993). For an E-I-S sequence, the Sendai virus S, I, and E sequences, for example, 5'-CTTTCACCCT-3' (SEQ ID NO: 20), 5'-AAG-3', and 5'-TTTTTCTTACTACGG-3' (SEQ ID NO: 21), respectively, can be used in, for example, the 3'-side of the oligo DNA insertion fragment.

PCR can be performed according to conventional methods, using Taq polymerase or other DNA polymerases. The amplified fragments of interest may be digested with Not I, and then inserted into the Not I site of plasmid vectors such as pBluescript. The nucleotide sequences of PCR products thus obtained are confirmed with a sequencer, and plasmids that include the correct sequence are selected. The inserted fragment is excised from these plasmids using Not I, and cloned into the Not I site of a plasmid composed of genomic cDNA. A recombinant Sendai virus cDNA can also be obtained by inserting the fragment directly into the Not I site of a genomic cDNA, without using a plasmid vector.

For example, a recombinant Sendai virus genomic cDNA can be constructed according to methods described in the literature (Yu, D. et al., Genes Cells 2: 457-466, 1997; Hasan, M. K. et al., J. Gen. Virol. 78: 2813-2820, 1997). For example, a double-stranded DNA is synthesized to have an E-I-S sequence attached to the 3' end of the sense strand of the foreign gene. The DNA is inserted immediately 3' of a desired S sequence in a cDNA encoding the plus strand of the genome. For example, on a cDNA that encodes the plus strand genome, a restriction site (e.g., Not I site) is first placed between a sequence encoding the desired viral protein gene and an S sequence that transcribes the gene. A DNA encoding a foreign gene-E-I-S sequence can then be inserted into the restriction site (Tokusumi, T. et al. Virus Res 86(1-2), 33-8 (2002)).

A viral vector can be efficiently reconstituted by transcribing a DNA encoding a genomic RNA of a recombinant virus thus prepared, in cells by CA promoter in the presence of the above-described viral proteins (L, P, and N). The method of the present invention can be applied to methods for reconstituting various recombinant viruses (WO97/16539; WO97/16538; WO03/025570; Durbin, A. P. et al., 1997, Virology 235: 323-332; Whelan, S. P. et al., 1995, Proc. Natl. Acad. Sci. USA 92: 8388-8392; Schnell. M. J. et al., 1994, EMBO J. 13: 4195-4203; Radecke, F. et al., 1995, EMBO J. 14: 5773-5784; Lawson, N. D. et al., Proc. Natl. Acad. Sci. USA 92: 4477-4481; Garcin, D. et al., 1995, EMBO J. 14: 6087-6094; Kato, A. et al., 1996, Genes Cells 1: 569-579; Baron, M. D. and Barrett, T., 1997, J. Virol. 71: 1265-1271; Bridgen, A. and Elliott, R. M., 1996, Proc. Natl. Acad. Sci. USA 93: 15400-15404). When the method of the present invention is applied to these methods, minus strand RNA viruses including parainfluenza virus, vesicular stomatitis virus, rabies virus, measles virus, rinderpest virus, and Sendai virus can be reconstituted from DNA with high efficiency. When a viral genome-encoding DNA is made envelope-constituting protein genes such as F gene, HN gene, and/or M gene deficient, such DNAs do not form infectious virions as is. However, infectious virions can be formed by separately introducing host cells with these deficient genes, and/or genes encoding the envelope proteins of other viruses, and then expressing these genes therein (Hirata, T. et al., 2002, J. Virol. Methods, 104: 125-133; Inoue, M. et al., 2003, J. Virol. 77: 6419-6429). When envelope-constituting proteins are expressed in virus-producing cells, it is preferable to use a CA promoter to express the envelope-constituting proteins. For this purpose, a DNA encoding an envelope-constituting protein is linked downstream of a CA promoter. This allows the envelope-constituting protein to be directly expressed by a CA promoter.

Specific methods include, for example, a method for transiently producing viruses. One of such methods is a method of transfecting mammalian cells with a vector for transcribing a DNA encoding a ribozyme and a minus-strand RNA virus genome RNA or the complementary strand thereof under the control of a CA promoter, and a vector for expressing viral proteins constituting an RNP comprising the minus-strand RNA virus genome RNA under the control of a CA promoter. Functional RNP is formed through the transcription of the genome RNA or antigenome RNA of the minus-strand RNA virus by a CA promoter in the presence of RNP-constituting viral proteins. As a result viruses are reconstituted. The minus-strand RNA virus vector can be obtained by recovering the minus-strand RNA virus produced in the cells or propagation products thereof.

In another method, a vector comprising a bacteriophage RNA polymerase-encoding DNA operably linked to a CA promoter, and a vector comprising a DNA that encodes a minus-strand RNA virus genome RNA or the complementary strand thereof and is linked downstream of the RNA polymerase recognition sequence, are transfected into mammalian cells along with a vector that expresses RNP-constituting viral proteins (N, L, and P) under the control of a CA promoter, wherein the RNP contains a minus-strand RNA virus genome RNA. In the presence of RNP-constituting viral proteins, the RNA polymerase is expressed by the CA promoter, and functional RNP is formed through the transcription of the genome RNA or antigenome RNA of the minus-strand RNA virus by the RNA polymerase expressed. As a result, viruses are reconstituted. The minus-strand RNA virus can be obtained by recovering the minus-strand RNA virus produced in the cells or propagation products thereof.

The vector used for transfection is preferably a plasmid. Each plasmid may be constructed to express a single protein. Alternatively, multiple proteins may be expressed on a single plasmid. For this purpose, a single plasmid may have multiple promoters. Alternatively, multiple proteins may be produced by a single promoter using IRES or such. For example, when two or more types of proteins are expressed by a single promoter using a non-promoter mechanism such as IRES, the proteins are considered to be expressed by a CA promoter when the promoter is CA promoter. However, it is preferred that each of the viral proteins (L, P, and N) that constitute an RNP comprising a minus-strand RNA virus genome RNA is at least expressed by a separate CA promoter. The transfection-based transient viral production described above is superior because it can rapidly produce viruses without using special cells.

Methods for transfecting cells with nucleic acids include the calcium phosphate method (Graham, F. L. and Van Der Eb, J., 1973, Virology 52: 456; Wigler, M. and Silverstein, S., 1977, Cell 11: 223), methods using various transfection reagents, electroporation, or such. The calcium phosphate method can be performed, for example, under the conditions of 2 to 4% $CO_2$, 35° C., 15 to 24 hours, and the DNA concentration in the precipitate mixture of 20 to 30 µg/ml, according to Chen and Okayama (Chen, C. and Okayama, H., 1987, Mol. Cell. Biol. 7: 2745). As a transfection reagent, DEAE-dextran (Sigma #D-9885 M.W. $5 \times 10^5$), DOTMA (Roche), Superfect (QIAGEN #301305), DOTAP, DOPE, DOSPER (Roche #1811169), TransIT-LT1 (Mirus, Product No. MIR 2300), or the like can be used. To prevent transfection reagent/DNA complexes from decomposing in endosomes, chloroquine may also be added (Calos, M. P., 1983, Proc. Natl. Acad. Sci. USA 80: 3015). Electroporation has a wide versatility because it is not cell-selective. It is applied by optimizing the duration of pulse electric current, shape of the pulse, potency of electric field (gap between electrodes, voltage), conductivity of buffer, DNA concentration, and cell density. The methods using transfection reagents are suitable for the transduction into cells of DNA for vector reconstitution, since they are simple to operate and facilitate examination of many samples using a large amount of cells. Preferably, the Superfect Transfection Reagent (QIAGEN, Cat No. 301305), the DOSPER Liposomal Transfection Reagent (Roche, Cat No. 1811169), TransIT-LT1 (Mirus, Product No. MIR 2300) or such is used; however, the transfection reagents are not limited to these.

In another embodiment of the method of the present invention, proteins and/or RNAs required for viral production are expressed from the chromosomes of virus-producing cells. Specific examples of this method include, for example, a method using mammalian cell lines whose chromosomes contain integrated DNA which becomes transcribed by a CA promoter into viral genome RNA or the complementary strand thereof, or integrated DNA which is expressed as a bacteriophage-derived RNA polymerase by a CA promoter. Cells having the ability to produce higher titer viruses can be prepared by cloning transformants and selecting cells with high expression levels. Thus, such cells are useful for stably producing high titer viruses. In such cells, it is also preferred that the expression of viral genome RNA and RNA polymerase is designed to be responsive to and inducible upon stimulation, while in the absence of stimulation, neither is expressed by a CA promoter. Genes can be expressed inducibly by a CA promoter by using the loxP or FRT described above. The Cre recombinase or FLP recombinase is expressed at the time of viral production to induce the expression from a CA promoter.

In such cells, the minus-strand RNA virus can be reconstituted through transcription of viral genome RNA or the complementary strand thereof in the presence of viral proteins (N, L, and P) that constitute an RNP that contains the minus-strand RNA virus genome RNA. RNP-constituting proteins may be supplied by transfecting plasmid vectors encoding the proteins.

In a method of excising the minus-strand RNA virus genome with a ribozyme (for example, the HamRbz method), the amount of each plasmid used in the transfection is for example: 0.1 to 2 µg (more preferably, 0.3 µg) of an NP-expressing plasmid; 0.1 to 2 µg (more preferably, 0.5 µg) of a P-expressing plasmid; 0.5 to 4.5 µg (more preferably, 2.0 µg) of an L-expressing plasmid; 0.1 to 5 µg (more preferably, 0.5 µg) of an F-expressing plasmid; and 0.5 to 5 µg (more preferably, 5 µg) of a viral genome RNA-encoding plasmid (plus or minus strand). For producing SeV, for example, the plasmids described in the Examples may be used in the following amounts:

| | |
|---|---|
| pCAGGS-NP | 0.1 to 2 µg (more preferably, 0.3 µg) |
| pCAGGS-P | 0.1 to 2 µg (more preferably, 0.5 µg) |
| pCAGGS-L(TDK) | 0.5 to 4.5 µg (more preferably, 2.0 µg) |
| pCAGGS-F5R | 0.1 to 5 µg (more preferably, 0.5 µg) |
| pCAGGS-SeV (pCAGGS-SeV/ΔF-GFP) | 0.5 to 5 µg (more preferably, 5 µg) |

In a method of transcribing the minus-strand RNA virus genome by a bacteriophage RNA polymerase, it is possible to use 0.1 to 2 µg (more preferably 0.5 µg) of an NP-expressing plasmid, 0.1 to 2 µg (more preferably 0.5 µg) of a P-expressing plasmid, 0.5 to 4.5 µg (more preferably 2.0 µg) of an L-expressing plasmid, 0.1 to 5 µg (more preferably 0.5 µg) of an F-expressing plasmid, a T7 RNA polymerase-expressing plasmid (for example, 0.5 µg), and 0.5 to 5 µg (more preferably 5 µg) of a viral genome RNA-encoding plasmid (plus or minus strand). For producing SeV, for example, the plasmids described in the Examples can be used in the following amounts:

| | |
|---|---|
| pCAGGS-NP | 0.1 to 2 µg (more preferably, 0.5 µg) |
| pCAGGS-P | 0.1 to 2 µg (more preferably, 0.5 µg) |
| pCAGGS-L(TDK) | 0.5 to 4.5 µg (more preferably, 2.0 µg) |
| pCAGGS-F5R | 0.1 to 5 µg (more preferably, 0.5 µg) |
| pCAGGS-T7 | for example, 0.5 µg |
| pSeV(TDK)18+GFP (pSeV/ΔF-GFP) | 0.5 to 5 µg (more preferably, 5 µg) |

After culturing for about 48 to 72 hours after transfection, cells are harvested, and then disintegrated by repeating freeze-thawing about three times. Cells are re-infected with the disintegrated materials including RNP, and cultured. Alternatively, the culture supernatant is recovered, added to a culture solution of cells to infect them, and the cells are then cultured. Transfection can be conducted by, for example, forming a complex with lipofectamine, polycationic liposome, or the like, and transducing the complex into cells. Specifically, various transfection reagents can be used. For example, DOTMA (Roche), Superfect (QIAGEN #301305), DOTAP, DOPE, DOSPER (Roche #1811169), and TransIT-LT1 (Mirus, Product No. MIR 2300) may be cited. In order to prevent decomposition in the endosome, chloroquine may also be added (Calos, M. P., 1983, Proc. Natl. Acad. Sci. USA 80: 3015). In cells transduced with RNP, viral gene expression from RNP and RNP replication progress, and the virus is amplified. By appropriately diluting the viral solution (culture supernatant) thus obtained, and then repeating the amplification, possible contaminants can be removed. However, the method of the present invention does not use the vaccinia virus expressing T7 RNA polymerase. Thus, the method is superior since re-amplification is not required for removing the vaccinia virus. Vectors thus obtained can be stored at −80° C. In order to reconstitute a nontransmissible virus lacking a gene encoding an envelope-constituting protein, cells expressing the envelope-constituting protein (helper cells) may be used for transfection, or a plasmid expressing the envelope-constituting protein may be cotransfected. Alternatively, an envelope-gene defective type virus can be amplified by culturing the transfected cells overlaid with cells expressing the envelope-constituting protein (see WO00/70055 and WO00/70070).

Helper cells that are used to construct a minus-strand RNA viral vector lacking envelope-constituting protein genes can be prepared, for example, by transfecting genes encoding the deleted envelope-constituting proteins or other envelope proteins (for example, VSV-G and amphotropic env) (see WO 00/70055 and WO 00/70070; Hasan, M. K. et al., 1997, J. General Virology 78: 2813-2820). To enable inducible expression, for example, the envelope protein genes are inserted into a vector having a recombinase target sequence, such as Cre/loxP inducible expression plasmid pCALNdlw (Arai, T. et al., J. Virology 72, 1998, p 115-1121). Such cells may be, for example, a monkey kidney-derived cell line LLC-MK2 (ATCC CCL-7), which is frequently used for SeV proliferation. LLC-MK2 cells are cultured at 37° C. under 5% $CO_2$ in MEM supplemented with 10% heat-inactivated fetal bovine serum (FBS), 50 units/ml penicillin G sodium, and 50 μg/ml streptomycin. Since SeV-F gene product is cytotoxic, LLC-MK2 cells are introduced with the above-described plasmid pCALNdLw/F, which is designed to inducibly express products of envelope protein genes by Cre DNA recombinase, using the calcium phosphate method (Mammalian Transfection kit (Stratagene)) according to well known protocols. The cells are cloned by limiting dilution and then culture-expanded, followed by selection of cell lines with high expressions of the introduced genes. For this purpose, for example, cells are infected with adenovirus AxCANCre, for example, at an moi of 3 to 5 by the method of Saito et al. (Saito et al., Nucl. Acids Res. 23: 3816-3821 (1995); Arai, T. et al., J. Virol 72, 1115-1121 (1998)), and are then selected by Western blotting or virus production.

Deletion of the spike protein F or HN gene is effective in rendering SeV vectors nontransmissible, whereas deletion of the envelope-ling protein M gene is effective in disabling particle formation in infected cells. Alternatively, vectors lacking any combination of at least two of F, HN, and M genes assure greater safety. For example, SeV that lacks both M and F genes (SeV/ΔMΔF) is nontransmissible and defective in particle formation. SeV/ΔMΔF retains high infectivity and gene expression ability in vitro and in vivo, and their degrees are comparative to those of the wild type SeV vector. These SeV/ΔMΔF characteristics will further contribute to the improvement of SeV safety.

Titers of viruses thus recovered can be determined, for example, by measuring CIU (Cell Infecting Unit) or hemagglutination activity (HA) (WO00/70070; Kato, A. et al., 1996, Genes Cells 1: 569-579; Yonemitsu, Y & Kaneda, Y, Hemagulutinating virus of Japan-liposome-mediated gene delivery to vascular cells. Ed. by Baker A H. Molecular Biology of Vascular Diseases. Method in Molecular Medicine: Humana Press: pp. 295-306, 1999). Titers of vectors carrying GFP (green fluorescent protein) marker genes and the like can be quantified by directly counting infected cells, using the marker as an indicator (for example, as GFP-CIU). Titers thus measured can be treated in the same way as CIU (WO00/70070).

So long as a virus can be reconstituted, the host cells used in the reconstitution are not particularly limited. For example, in the reconstitution of Sendai virus vectors and the like, cultured cells such as LLC-MK2 cells and CV-1 cells (for example, ATCC CCL-70) derived from monkey kidney, BHK cells (for example, ATCC CCL-10) derived from hamster kidney, and cells derived from humans can be used. Further, to obtain a large quantity of a Sendai virus vector, a viral vector obtained from an above-described host can be used to infect embrionated hen eggs to amplify the vector. Methods for manufacturing viral vectors using hen eggs have already been developed (Nakanishi, et al., ed. (1993), "State-of-the-Art Technology Protocol in Neuroscience Research III, Molecular Neuron Physiology", Koseisha, Osaka, pp. 153-172). Specifically, for example, a fertilized egg is placed in an incubator, and cultured for nine to twelve days at 37 to 38° C. to grow an embryo. After the viral vector is inoculated into the allantoic cavity, the egg is cultured for several days (for example, three days) to proliferate the viral vector. Conditions such as the period of culture may vary depending upon the recombinant Sendai virus being used. Then, allantoic fluids including the vector are recovered. Separation and purification of a Sendai virus vector from allantoic fluids can be performed according to a usual method (Tashiro, M., "Virus Experiment Protocol," Nagai, Ishihama, ed., Medical View Co., Ltd., pp. 68-73, (1995)).

According to the method for producing viruses as described herein, the viral vector of the present invention can be released into extracellular fluid of virus producing cells at a titer of, for example, $1 \times 10^5$ CIU/ml or higher, preferably $1 \times 10^6$ CIU/ml or higher, more preferably $5 \times 10^6$ CIU/ml or higher, more preferably $1 \times 10^7$ CIU/ml or higher, more preferably $5 \times 10^7$ CIU/ml or higher, more preferably $1 \times 10^8$ CIU/ml or higher, and more preferably $5 \times 10^8$ CIU/ml or higher. The titer of virus can be determined according to methods described herein or elsewhere (Kiyotani, K. et al., Virology 177(1), 65-74 (1990); and WO00/70070).

The recovered viral vectors can be purified to be substantial pure. The purification can be achieved using known purification/separation methods, including filtration, centrifugation, adsorption, and column purification, or any combinations thereof. The phrase "substantially pure" means that the virus component constitutes a major proportion of a solution of the viral vector. For example, a viral vector composition can be confirmed to be substantially pure by the fact that the proportion of protein contained as the viral vector component to the total protein (excluding proteins added as carriers and stabilizers) in the solution is 10% (w/w) or greater, preferably 20% or greater, more preferably 50% or greater, preferably 70% or greater, more preferably 80% or greater, and even more preferably 90% or greater. Specific purification methods for, for example, the paramyxovirus vector includes methods using cellulose sulfate ester or cross-linked polysaccharide sulfate ester (Japanese Patent Application Kokoku Publication No. (JP-B) S62-30752 (examined, approved Japanese patent application published for opposition), JP-B S62-33879, and JP-B S62-30753) and methods including adsorbing to fucose sulfate-containing polysaccharide and/or degradation products thereof (WO97/32010), but are not limited thereto.

In the production of compositions containing the viral vector of the present invention, the vector may be combined with desired pharmaceutically acceptable carriers or media according to needs. The "pharmaceutically acceptable carriers or media" refers to materials that can be administered together with the vector and that do not significantly inhibit the gene transfer via the vector. Such carriers and media include, for example, sterile water, sodium chloride solution, dextrose solution, lactated Ringer's solution, culture medium, serum, and phosphate buffered saline (PBS). They may be appropriately combined with the vector to formulate a composition. The composition of the present invention may also include membrane stabilizers for liposome (for example, sterols such as cholesterol). The composition may also include antioxidants (for example, tocopherol or vitamin E). In addition, the composition may also include vegetable oils, suspending agents, detergents, stabilizers, biocidal agents, and the like. Furthermore, preservatives and other additives may also be added. The formula of the present composition may be aqueous solution, capsule, suspension, syrup, or the like. The composition of the present invention may also be in a form of solution, freeze-dried product, or aerosol. When it is a freeze-dried product, it may include sorbitol, sucrose, amino acids, various proteins, and the like as a stabilizer.

When a minus-strand RNA viral vector is used to induce immunity, immunostimulants such as cytokine, cholera toxin, and *Salmonella* toxin can be added to improve immunogenicity. Furthermore, such vaccine compositions may be combined with adjuvants, such as alum, incomplete Freund's adjuvant, MF59 (oil emulsion), MTP-PE (muramyl tripeptide derived from cell wall of mycobacteria), and QS-21 (derived from soapbark tree *Quilaja saponaria*). When administering the composition or cell, it is effective to combine them with cytokines that improve the adjuvant effect. Such genes include, for example, (i) single-chain IL-12 (Proc. Natl. Acad. Sci. USA 96 (15): 8591-8596, 1999);
(ii) interferon-γ (U.S. Pat. No. 5,798,100);
(iii) granulocyte colony stimulating factor (GM-CSF); and
(iv) a combination of GM-CSF and IL-4 (J. Neurosurgery 90 (6), 1115-1124 (1999)).

The dose of a minus-strand RNA viral vector may vary depending upon the disorder, body weight, age, gender, and symptoms of patients, as well as the form of the composition to be administered, administration method, gene to be transduced, and so on; however, those skilled in the art can appropriately determine the dosage. Doses of the vector are preferably administered in a pharmaceutically acceptable carrier in a range of preferably about $10^5$ CIU/ml to about $10^{11}$ CIU/ml, more preferably about $10^7$ CIU/ml to about $10^9$ CIU/ml, most preferably about $1\times10^8$ CIU/ml to about $5\times10^8$ CIU/ml. In humans, a single dose is preferably in the range of $2\times10^5$ CIU to $2\times10^{11}$ CIU, and can be administered once or more, so long as the side effects are within a clinically acceptable range. The same applies to the number of administrations per day. With non-human animals, for example, the above-described doses can be converted based on the body weight ratio or volume ratio of a target site for administration (e.g. average values) between the animal of interest and human, and the converted doses can be administered to the animal. After administering a transmissible minus-strand RNA viral vector to an individual or cell, when the proliferation of the viral vector must be restrained upon treatment completion and such, it is also possible to specifically restrain only the proliferation of the viral vector, with no damage to the host, by administering an RNA-dependent RNA polymerase inhibitor. For ex vivo administration, a vector is contacted with target cells outside the body (for example, in a test tube or dish). The vector is preferably administered at an MOI of 1 to 500, more preferably 2 to 300, still more preferably 3 to 200, yet preferably 5 to 100, even more preferably 7 to 70. There is no limitation on the type of organism to which the minus-strand RNA viral vector of the present invention is administered. Such organisms include desired mammals including human and nonhuman mammals, specifically, human, mouse, rat, dog, pig, cat, bovine, rabbit, sheep, goat, and monkey.

EXAMPLES

Hereinafter, the present invention will be explained in more detail with reference to the Examples, but is not to be construed as being limited thereto. All the references cited herein are incorporated as parts of the present specification.

Example 1

Plasmid Construction (FIG. 1)

Construction of pCAGGS (B type)

pCALNdLw (Arai, T. et al. J. Virology 72, 1998, p. 1115-1121) was digested with XhoI, purified using the Qiaquick PCR Purification kit, and ligated. The plasmid from which the XhoI fragment was deleted was selected and named pCAGGS (B type). pCAGGS (B type) was digested with SalI, and blunted using the Pfu DNA polymerase. The DNA was purified with the Qiaquick PCR Purification kit, and ligated. The plasmid in which the SalI site was deleted was selected and named pCAGGS(BSX)

Figure 2:
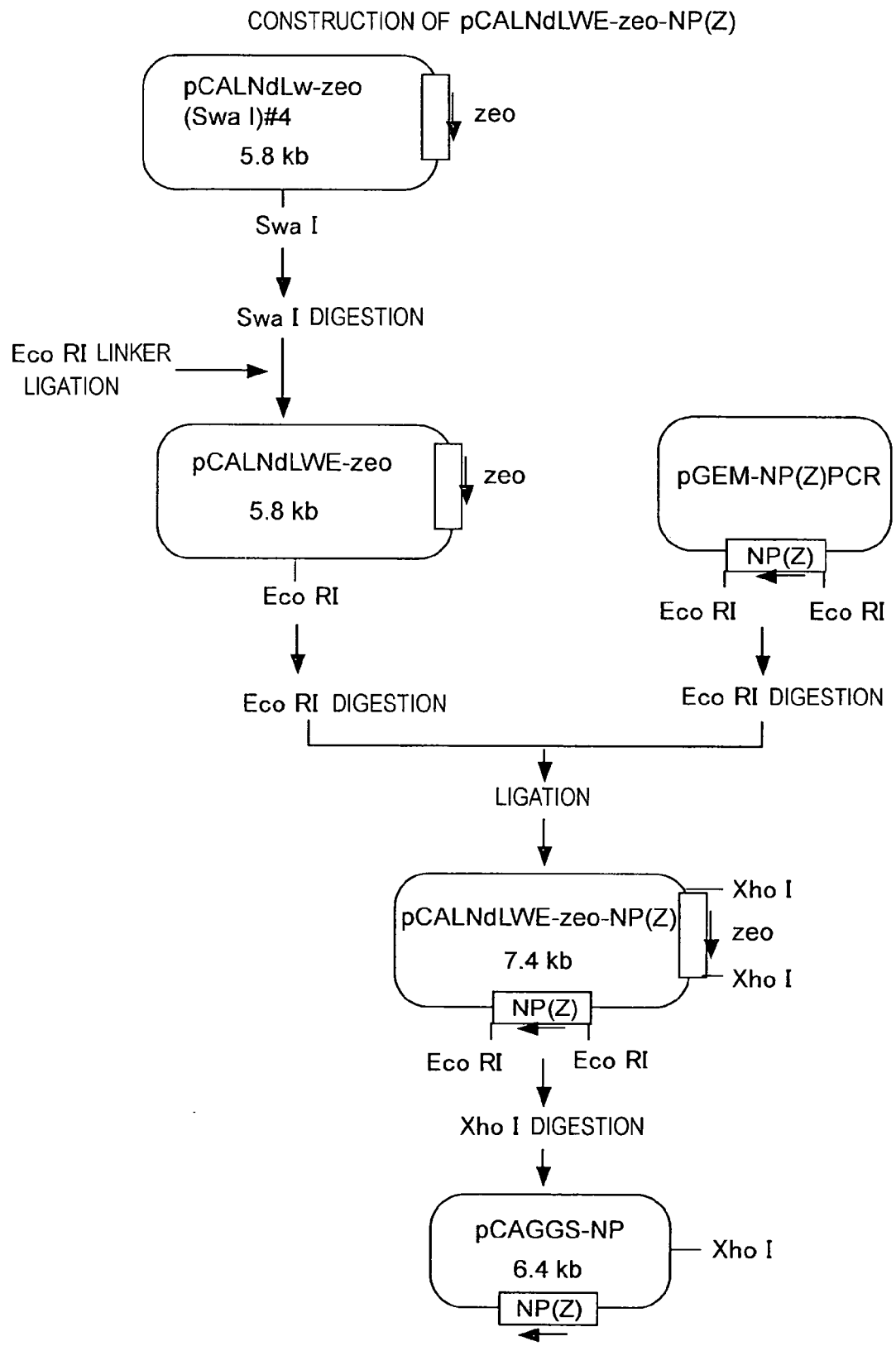
FIG. 2 shows the procedure for constructing pCALNdLWE-zeo-NP(Z).

Construction of pCAGGS-NP (FIG. 2)

pCALNdLw was digested with SpeI and EcoT22I, and separated by agarose gel electrophoresis. The 2651-bp and 3674-bp fragments were excised, and purified with the Qiaquick gel Extraction kit. Then, the 2651-bp fragment was digested with XhoI. After separation by agarose gel electrophoresis, a 1760-bp band was purified. The Zeocin resistance gene was amplified by PCR using pcDNA3.1/Zeo(+) as template and the following primers: 5'-TCTCGAGTCGCTCG-GTACGATGGCCAAGTTGACCAGTGCCGT-TCCGGTGCTCAC-3' (SEQ ID NO: 22) and 5'-AATGCATGATCAGTAAATTACAATGAA-CATCGAACCCCAGAGTCCCGCTCAGTCCT GCTC-CTCGGCCACGAAGTGCACGCAGTTG-3' (SEQ ID NO: 23). The amplified DNA was digested with XhoI and EcoT22I, and separated by agarose gel electrophoresis. A band of 438 bp was excised and purified using the Qiaquick Gel Extraction kit. The three fragments, namely the fragment comprising the Zeocin resistance gene and the 3674-bp and 1761-bp fragments described above, were ligated to each other to yield pCALNdLw-Zeo. This pCALNdLw-Zeo was digested with SwaI and an EcoRI linker (STRATAGENE) was inserted to yield pCALNdLWE-Zeo. A Sendai virus cDNA introduced with a multi-cloning site (JP-A 2002-272465) (hereinafter referred to as pSeV(TDK)) was digested with NotI and XhoI, and separated by agarose gel electrophoresis. A band of 1669 bp was excised and purified using the Qiaquick Gel Extraction kit. The fragment comprising the NP gene was inserted into pGEM11Zf(+) (Promega), which had been digested with NotI and XhoI, to yield pGEM-NP (Z)PCR14-3. PCR amplification was performed using this plasmid as template and the following primers: 5'-CCG-GAATTCAACAAATGGCCGGGTTGTTGAG-CACCTTCGA-3' (SEQ ID NO: 24) and 5'-CCGGAATTC-CTAGATTCCTCCTATCCCAGCTACTGCTGCTCG-3' (SEQ ID NO: 25). The PCR product was digested with EcoRI, and inserted into the EcoRI site of pCALNdLWE-Zeo to yield pCALNdLWE-Zeo-NP(Z). Then, pCALNdLWE-Zeo-NP(Z) was digested with XhoI, and ligated to construct a plasmid from which the XhoI fragment was deleted. The resulting plasmid was named pCAGGS-NP.

Figure 3:
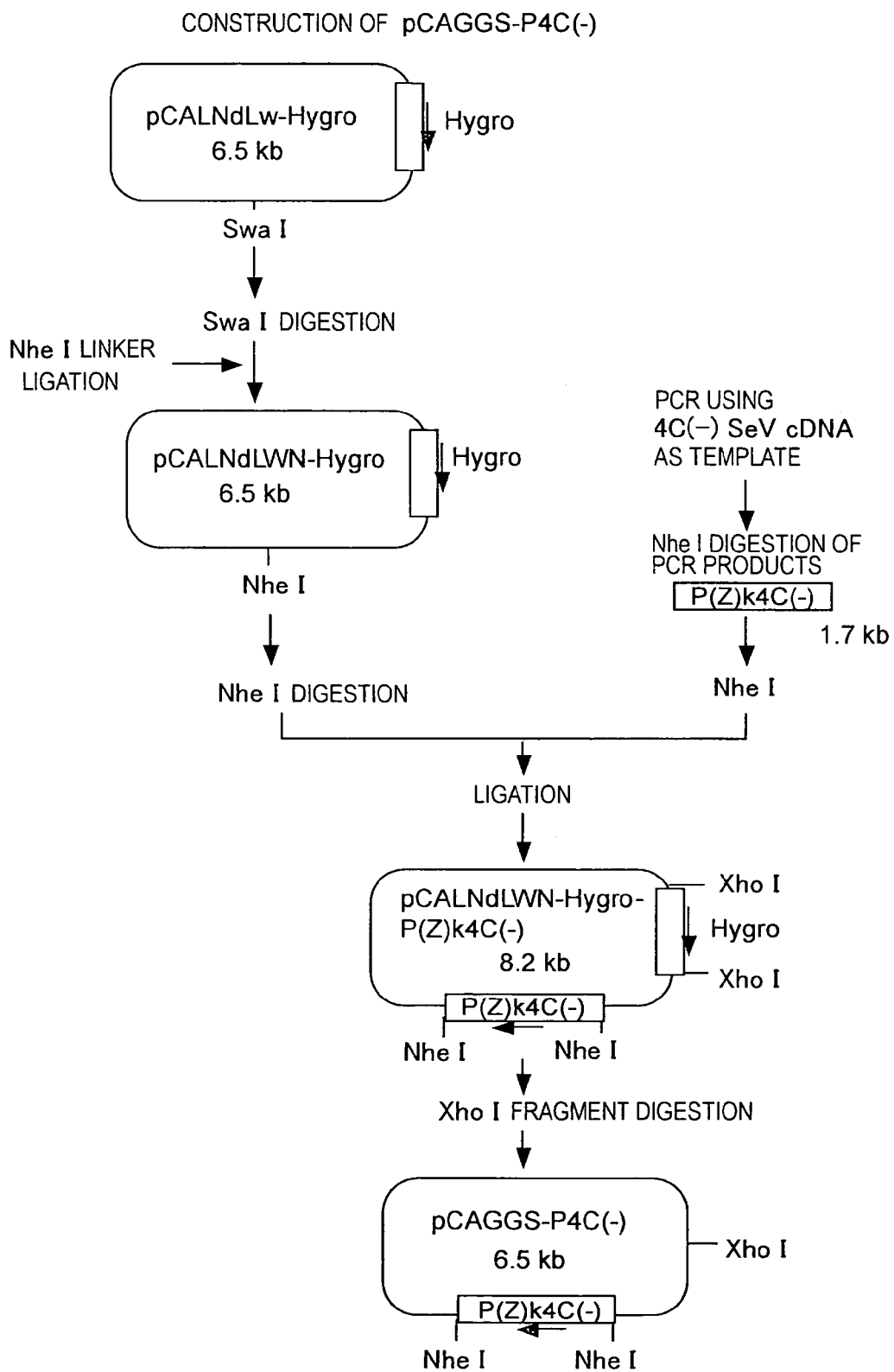
FIG. 3 shows the procedure for constructing pCAGGS-P4C(−).

Construction of pCAGGS-P4C(−) (FIG. 3)

pCALNdLw-HygroM (Inoue, M. et al. J. Virology 77, 2003, p 6419-6429) was digested with XhoI, and separated by agarose gel electrophoresis. A 1679-bp band containing the hygromycin resistance gene was excised and purified using the Qiaquick Gel Extraction kit. pCALNdLw was digested with XhoI. After agarose gel electrophoresis, a 4864-bp band was excised and purified using the Qiaquick Gel Extraction kit. These two fragments were ligated to each other to construct pCALNdLw-Hygro. This pCALNdLw-Hygro was digested with SwaI, and an NheI linker (STRATAGENE) was inserted to yield pCALNdLWN-Hygro. PCR was carried out with the KOD-PLUS DNA Polymerase (TOYOBO), using 4C(−)SeV cDNA (Kurotani, Kato, Nagai, et al Genes to Cells 3, 1998, p 111-124) as template and the following primers: 5'-CTAGCTAGCCCACCATGGATCAAGATGC-CTTCATTCTAAAAGAAGATTCT-3' (SEQ ID NO: 26) and 5'-CTAGCTAGCCTAGTTGGTCAGTGACTC-TATGTCCTCTTCTACGAGTTCCA-3' (SEQ ID NO: 27). The PCR product was purified using the Gene Clean kit, and then digested with NheI. The product was purified with the Gene Clean kit. This is inserted into the NheI site of pCALNdLWN-hygro described above to yield pCALNdLWN-hygro-P(Z)k4C(−). This plasmid was digested with XhoI, and then purified with the Qiaquick PCR Purification kit. After ligation, the plasmid from which the XhoI fragment (hygromycin resistance gene region) was deleted was selected to yield pCAGGS-P4C(−).

Figure 4:
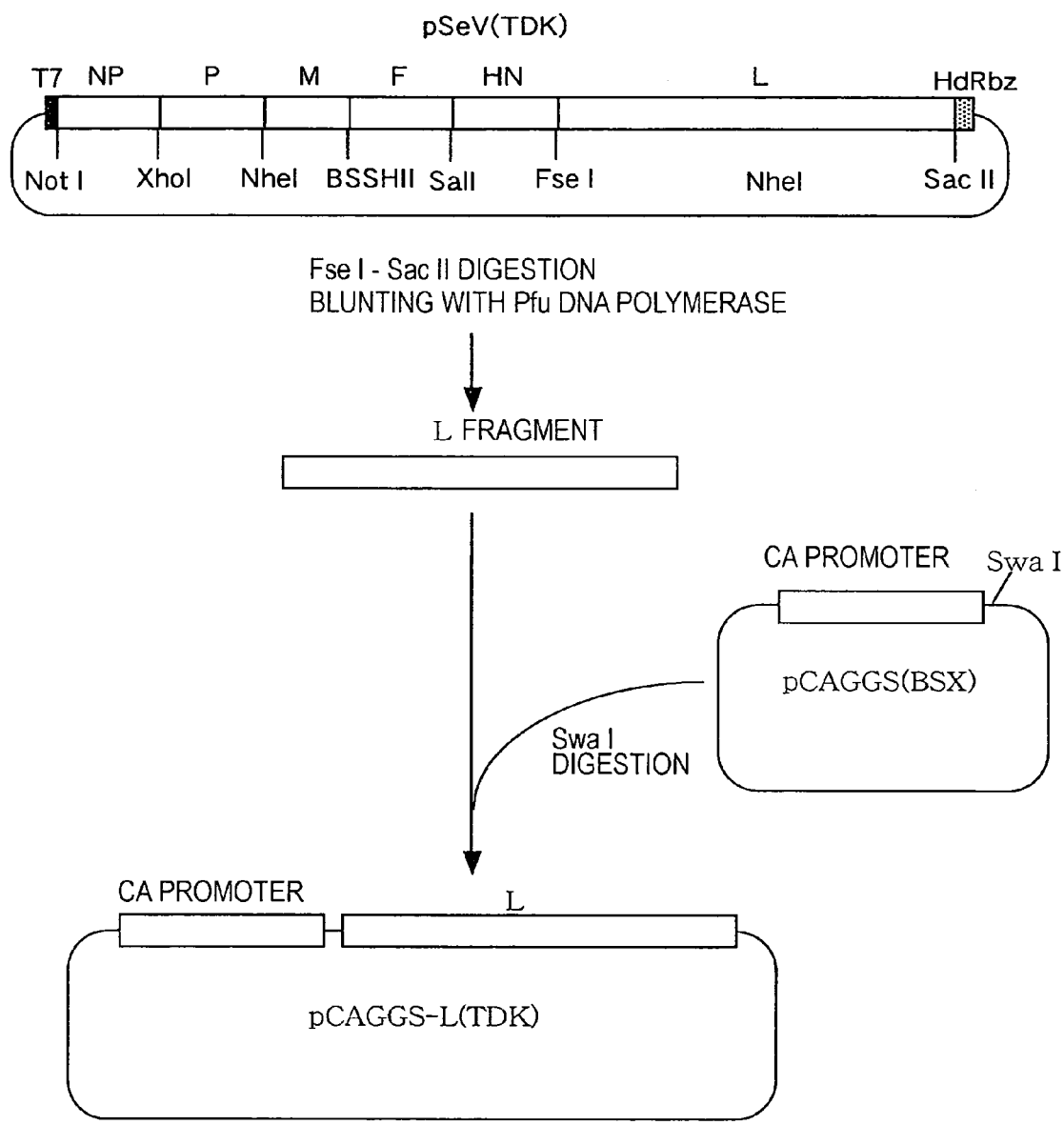
FIG. 4 shows the procedure for constructing pCAGGS-L (TDK).

Construction of pCAGGS-L(TDK) (FIG. 4)

pSeV(TDK) was digested with FseI and SacII and separated by agarose gel electrophoresis. A 6732-bp band was excised and purified using the Qiaquick Gel Extraction kit. The fragment was blunted by reacting with the Pfu DNA Polymerase and dNTP at 72° C. for 10 minutes. After purification with the Qiaquick PCR Purification kit, the fragment was inserted into the SwaI site of pCAGGS(BSX) to yield pCAGGS-L(TDK).

Figure 5:
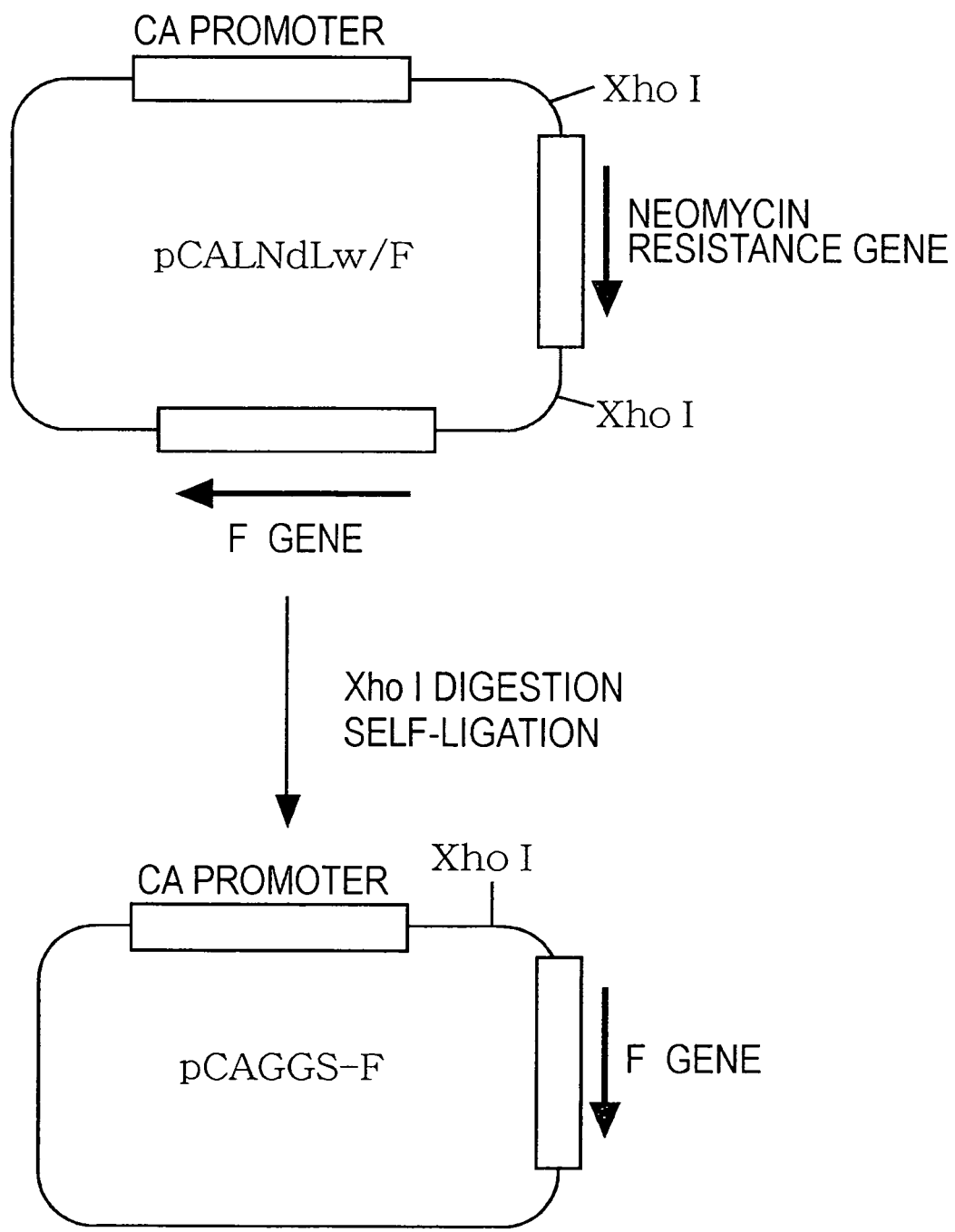
FIG. 5 shows the procedure for constructing pCAGGS-F.
Figure 6:
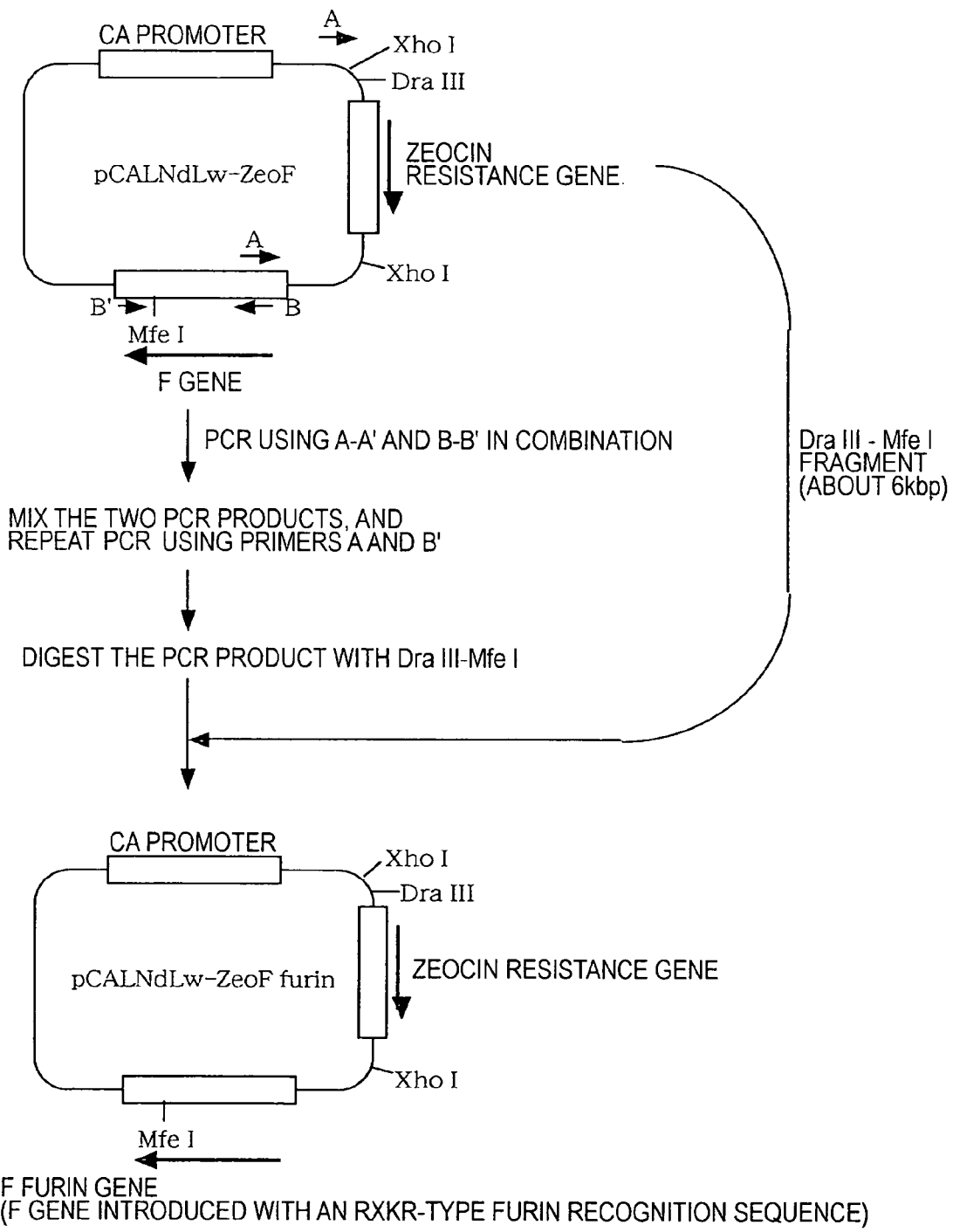
FIG. 6 shows the procedure for constructing pCAGGS-F5R.
Figure 7:
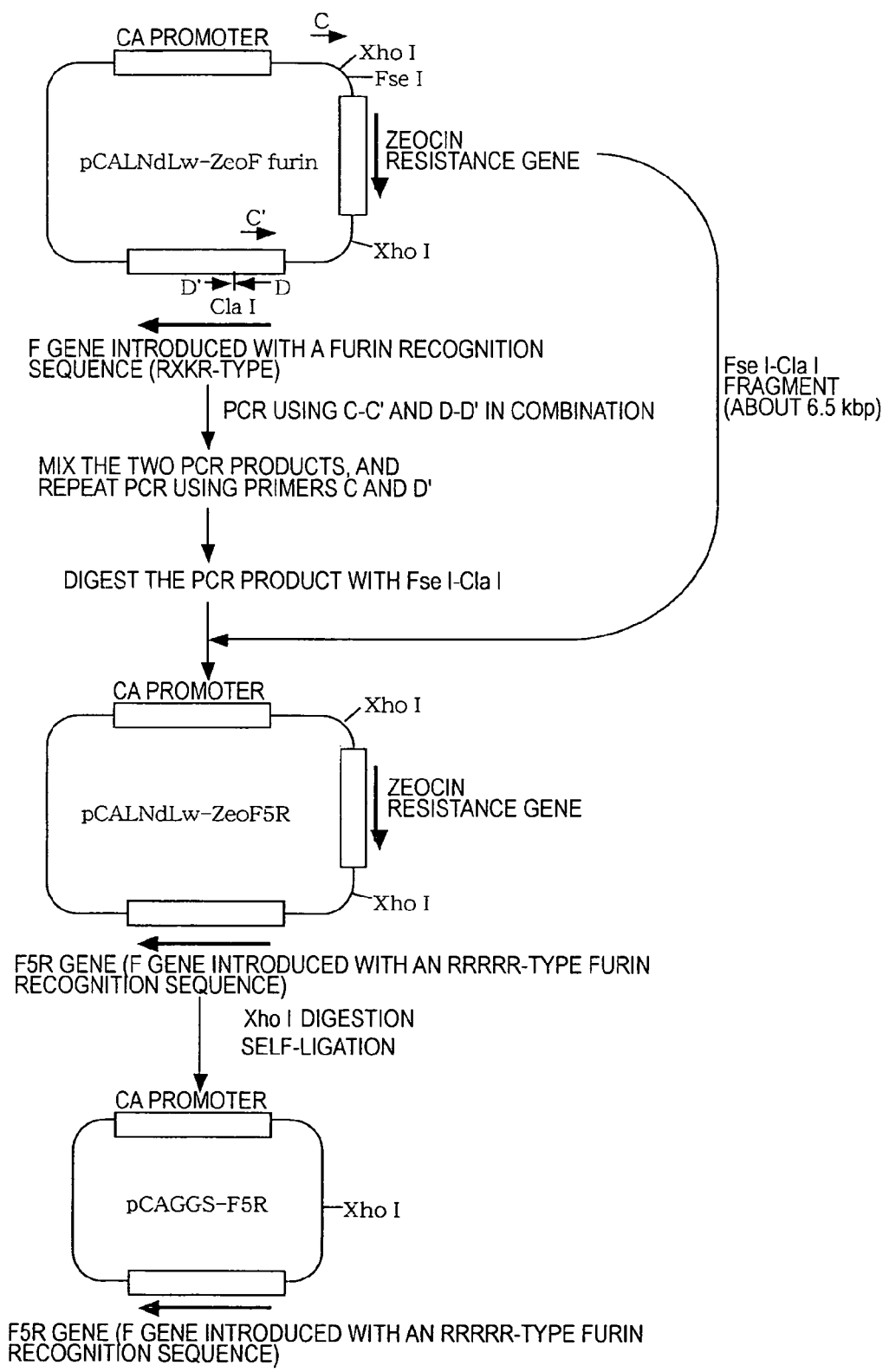
FIG. 7 shows the procedure for constructing pCAGGS-F5R (continuation from FIG. 6).

Construction of pCAGGS-F and pCAGGS-F5R (FIGS. 5 to 7)

pCALNdLw/F (Li, H.-O. et al. J. Virology 74, 2000, p 6564-6569) was digested with XhoI. After purification, the plasmid was ligated. The plasmid from which the XhoI fragment (Neomycin resistance gene region) was deleted was selected to obtain pCAGGS-F. PCR was carried out using pCALNdLw-ZeoF (Japanese Patent Application No. 2001-283451) as template and Pfu Turbo (STRATAGENE), under condition (I): combined primers 5'-CATTTTGGCAAA-GAATTGATTAATTCGAG-3' (SEQ ID NO: 28) and 5'-TCACAGCACCCAAGAATCTCTTCTGGC-GAGCACCGGCATTTTGTGTC-3' (SEQ ID NO: 29); and condition (II): combined primers 5'-GACACAAAATGCCG-GTGCTCGCCAGAAGAGATTCTTGGGTGCTGTGA-3' (SEQ ID NO: 30) and 5'-GATCGTAATCACAGTCTCTC-GAGAGTTGTACCATCTACCTAC-3' (SEQ ID NO: 31). After the PCR product was separated by agarose gel electrophoresis, the 1470-bp band yielded under condition (I) and the 1190-bp band yielded under condition (II) were excised and recovered using the GENE CLEAN KIT (referred to as PCR products (I) and (II), respectively). 1 µl each of the PCR products (I) and (II), both purified and 10-times diluted, was combined, and subjected to PCR using Pfu Turbo and combined primers 5'-CATTTTGGCAAAGAATTGATTAATTC-GAG-3' (SEQ ID NO: 28) and 5'-GATCGTAATCA-CAGTCTCTCGAGAGTTGTACCATCTACCTAC-3' (SEQ ID NO: 31). 5 µl of the PCR product was electrophoresed on an agarose gel, and stained with ethidium bromide. As a result, an expected band of 2.6 kb was detected. Thus, the remaining PCR product was purified using the Qiaquick PCR Extraction kit and digested in succession with the restriction enzymes DraIII and MfeI. After separation by agarose gel electrophoresis, a band of about 2.0 kb is excised from the gel. pCALNdLw-Zeo-F was digested in succession with DraIII and MfeI, and separated by agarose gel electrophoresis. A band of about 6 kp is excised and purified using GENECLEAN II KIT (BIO). The DraIII-MfeI fragment of pCALNdLw-Zeo-F was ligated with the above-described PCR DraIII-MfeI fragment to yield pCALNdLw-Zeo-F furin. Then, PCR was carried out using pCALNdLw-Zeo-F furin as template under condition (I): combined primers 5'-CATTTTGGCAAAGAATTGATTAATTCGAG-3' (SEQ ID NO: 28) and 5'-TCACAGCACCGAAGAATCTCCTC-CGGCGACGACCGGCATTTTGTGTCGTATC-3' (SEQ ID NO: 32); and condition (II): combined primers 5'-GATAC-GACACAAAATGCCGGTCGTCGCCGGAG-GAGATTCTTCGGTGCTGTGA-3' (SEQ ID NO: 33) and 5'-AAATCCTGGAGTGTCTTTAGCAGC-3' (SEQ ID NO: 34). After separation by electrophoresis, the ~1.4 kbp band in condition (I) and the ~200 bp band in condition (II) were excised and purified with the Qiaquick gel Extraction kit. 1 µl each of purified and 50-times diluted PCR products was combined, and subjected to PCR using Pfu Turbo and the combination of primers 5'-CATTTTGGCAAAGAATTGATTAAT-TCGAG-3' (SEQ ID NO: 28) and 5'-AAATCCTGGAGTGTCTTTAGCAGC-3' (SEQ ID NO: 34). 5 µl of the PCR product was separated by agarose gel electrophoresis and stained to confirm a ~1.6 kbp band. The remaining PCR product was purified with the Qiaquick PCR Purification kit, and then digested with ClaI and FseI. After separation by agarose gel electrophoresis, a band of about 1 kbp is excised and purified with the Qiaquick PCR Purification kit. pCALNdLw-Zeo-F furin was digested with ClaI and FseI. After separation by agarose gel electrophoresis, a band of about 8 kbp is excised and purified with the Qiaquick PCR Purification kit. The DNA was ligated with a purified ClaI-FseI-digested fragment of the PCR product described above to yield pCALNdLw-Zeo F5R. This pCALNdLw-Zeo F5R was digested with XhoI. After purification, the plasmid was ligated. The plasmid from which the XhoI fragment (including Zeocin resistance gene) was deleted was selected to obtain pCAGGS-F5R.

Figure 8:
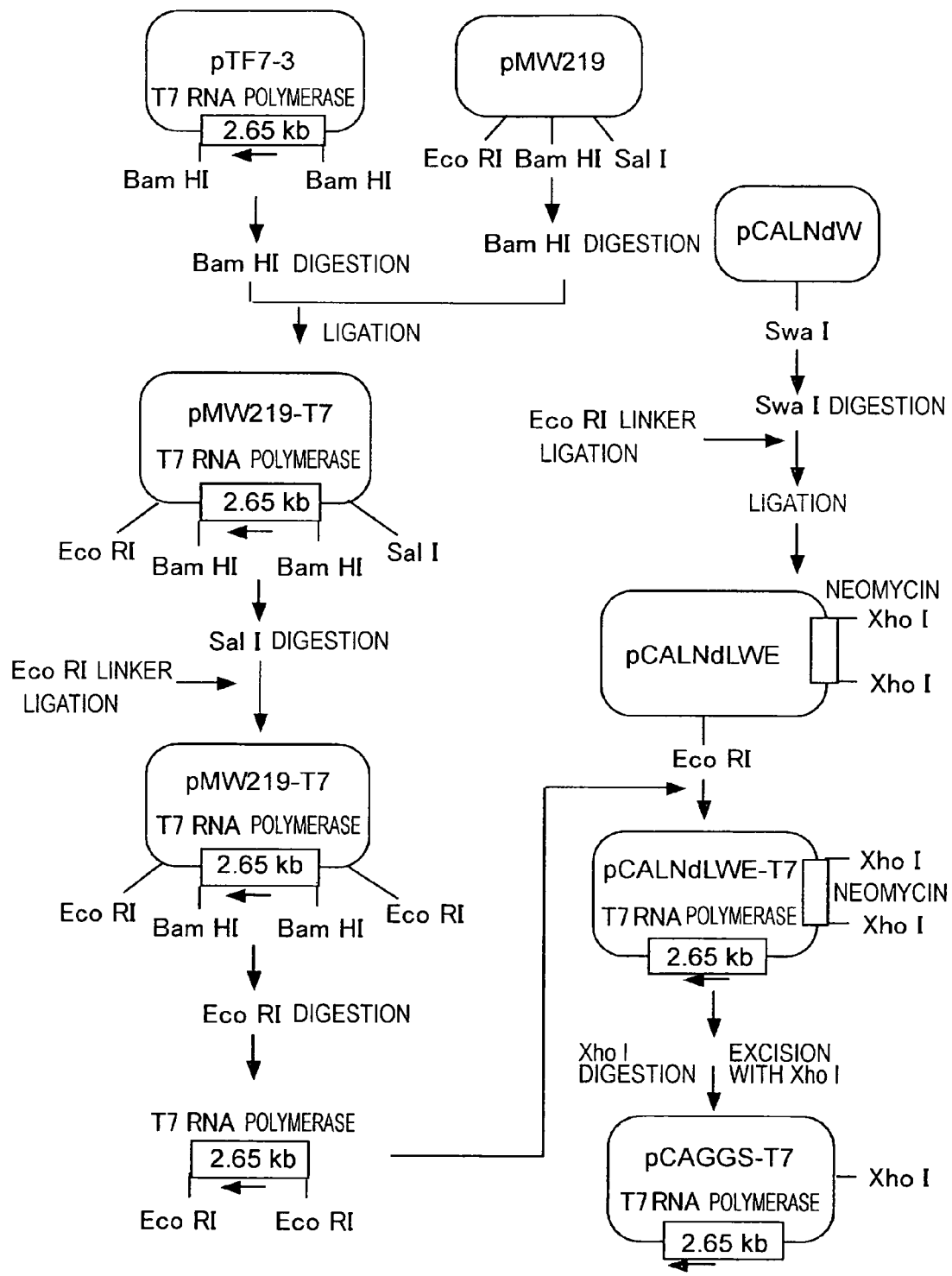
FIG. 8 shows the procedure for constructing pCAGGS-T7.

Construction of pCAGGS-T7 (FIG. 8)

pTF7-3 (ATCC No. 67202) was digested with BamHI. After separation by agarose gel electrophoresis, a fragment of 2.65 kbp comprising the T7 RNA polymerase gene was recovered and inserted into the BamHI site of pMW219 (Nippon Gene Co. Ltd.) to yield pMW219-T7. This pMW219-T7 was digested with SalI and blunted using the DNA Blunting kit (TaKaRa). An EcoRI linker (Stratagene #901026) was inserted to yield pMW219-T7-Eco RI. This pMW219-T7-Eco RI was digested with EcoRI. An EcoRI fragment comprising the T7 RNA polymerase was purified and inserted into the EcoRI site of pCALNdLWE described above to yield pCALNdLWE-T7.

Figure 9:
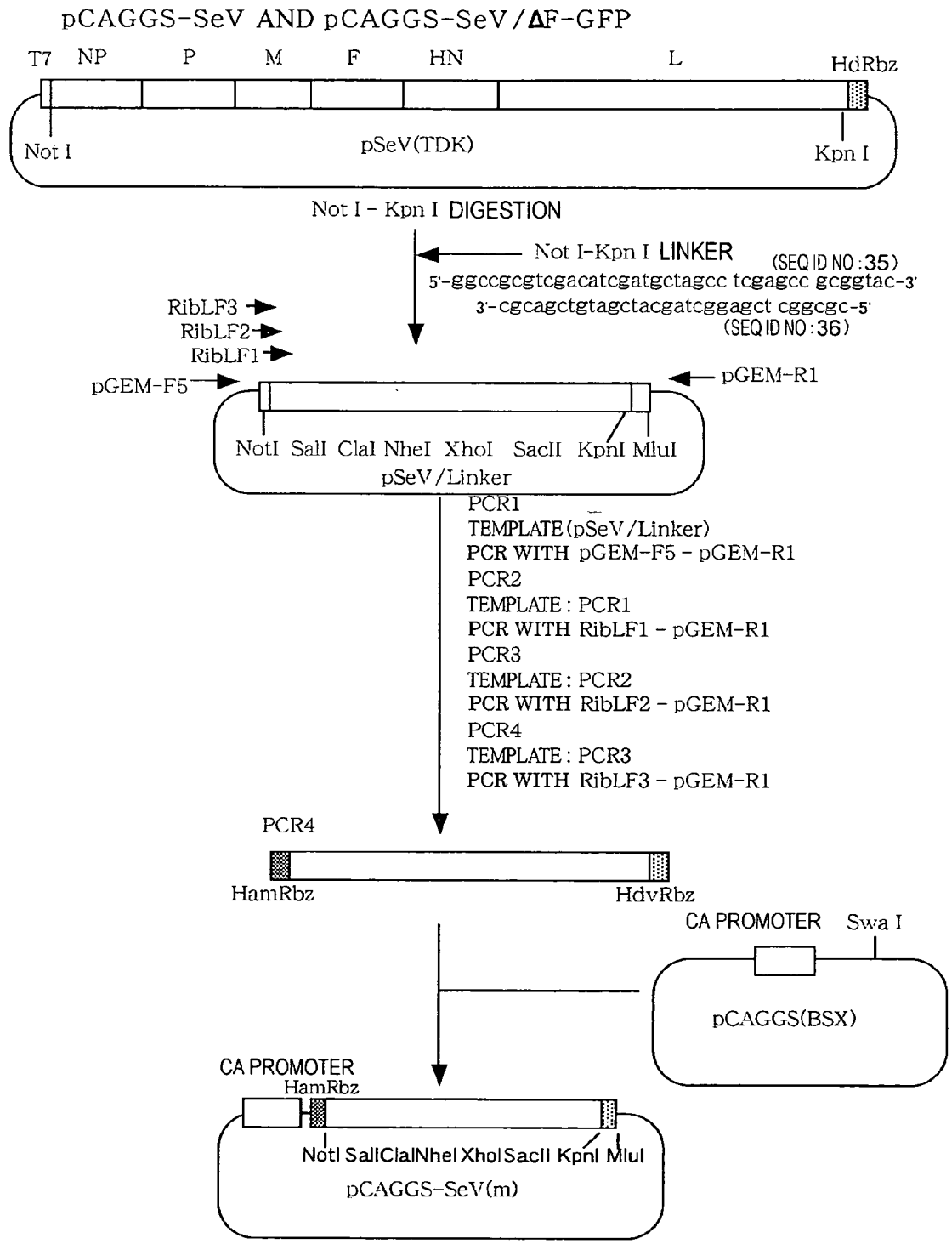
FIG. 9 shows the procedure for constructing pCAGGS-SeV and pCAGGS-SeV/ΔF-GFP.
Figure 10:
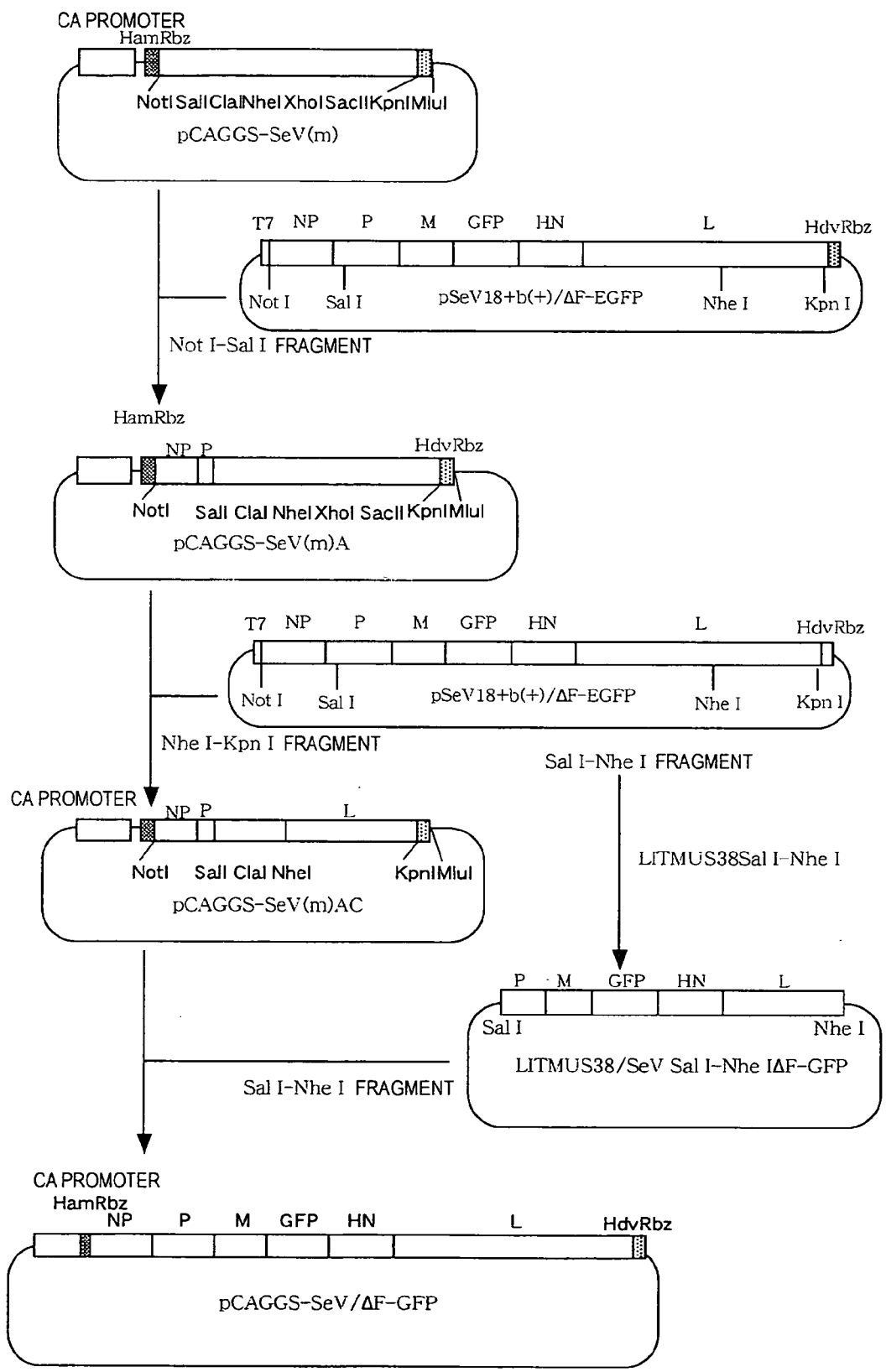
FIG. 10 shows the procedure for constructing pCAGGS-SeV and pCAGGS-SeV/ΔF-GFP (continued from FIG. 9).
Figure 11:
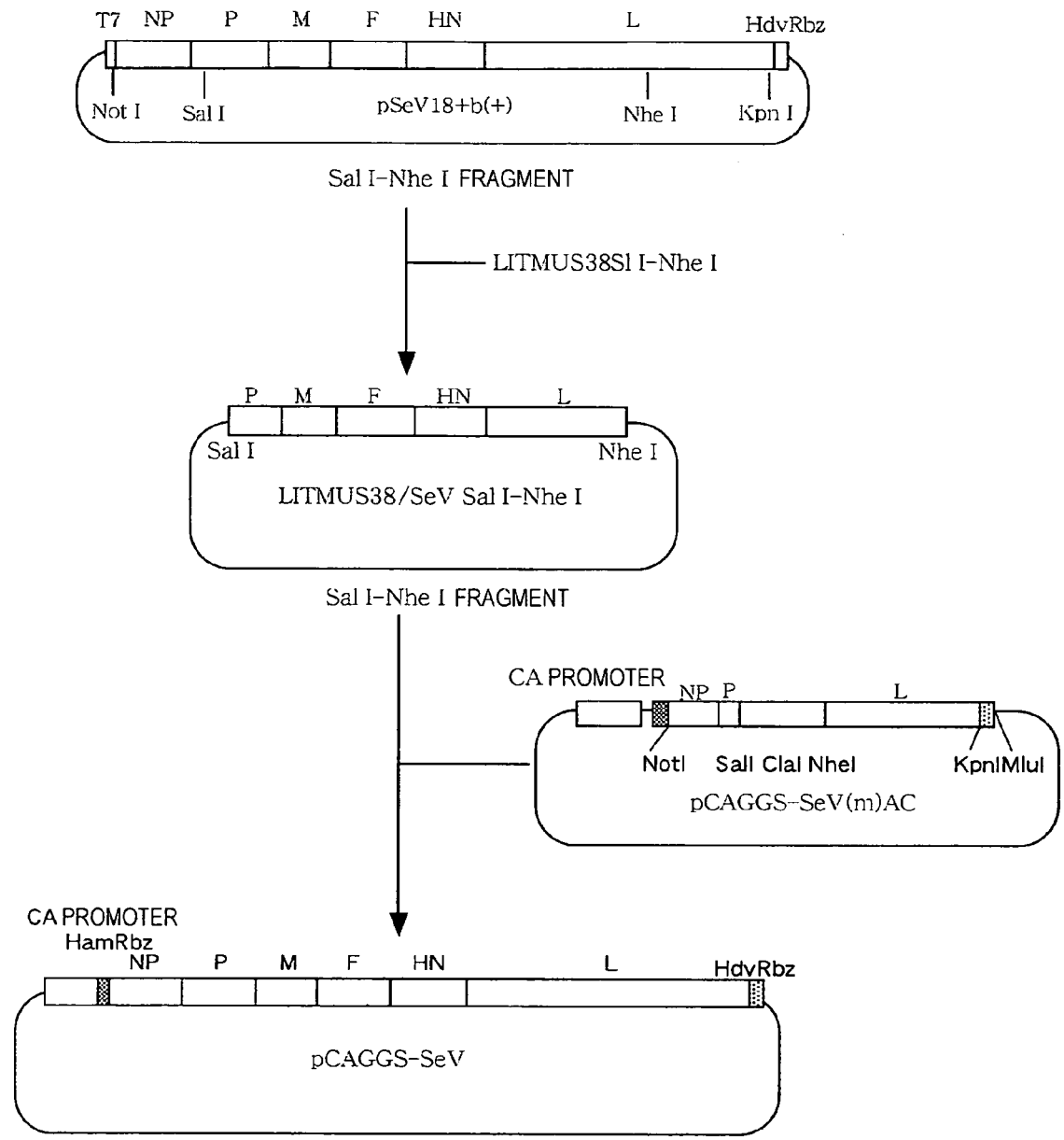
FIG. 11 shows the procedure for constructing pCAGGS-SeV (continued from FIG. 10).

Construction of pCAGGS-SeV and pCAGGS-SeV/AF-GFP (FIGS. 9 to 11)

pSeV(TDK) was digested with NotI and KpnI and separated by agarose gel electrophoresis. A band of 2995 bp was then excised and purified using the Qiaquick Gel Extraction kit. 2 µg (2 µl) each of MlinkerF: 5'-GGCCGCGTCGA-CATCGATGCTAGCCTCGAGCCGCGGTAC-3' (SEQ ID NO: 35) and MlinkerR: 5'-CGCGGCTCGAGGCTAG-CATCGATGTCGACGC-3' (SEQ ID NO: 36) was mixed with 21 µl of H₂O and annealed at 95° C. for 5 minutes, 85° C. for 15 minutes, 65° C. for 15 minutes, 37° C. for 15 minutes, 25° C. for 15 minutes, and then 4° C. The mixture and a solution of purified pSeV(TDK) NotI-KpnI were ligated to yield pSeV/Linker. PCR was carried out using the pSeV/Linker as template, KOD-Plus (TOYOBO), and the following primers: pGEM-F5: 5'-CTTAACTATGCGGCATCAGAGC-3' (SEQ ID NO: 37) and pGEM-R1: 5'-GCCGATTCAT-TAATGCAGCTGG-3' (SEQ ID NO: 38). The PCR product was purified using the Qiaquick PCR Purification kit. PCR was carried out using a solution of the purified PCR product as template, KOD-PLUS (TOYOBO), and the following primers: RibLF1: 5'-CTATAGGAAAGGAATTCCTATAGT-CACCAAACAAGAG-3' (SEQ ID NO: 39) and pGEM-R1: 5'-GCCGATTCATTAATGCAGCTGG-3' (SEQ ID NO: 38). The PCR product was purified using the Qiaquick PCR Purification kit. PCR was carried out using a solution of the purified PCR product as template, KOD-PLUS (TOYOBO), and the following primers: RibLF2: 5'-GATGAGTCCGT-GAGGACGAAACTATAGGAAAGGAATTC-3' (SEQ ID NO: 40) and pGEM-R1: 5'-GCCGATTCATTAATG-CAGCTGG-3' (SEQ ID NO: 38). The PCR product was purified using the Qiaquick PCR Purification kit. Furthermore, PCR was carried out using a solution of the purified PCR product as template, KOD-PLUS (TOYOBO), and the following primers: RibLF3: 5'-GCGGGCCCTCTCT-TGTTTGGTCTGATGAGTCCGTGAGGAC-3' (SEQ ID NO: 41) and pGEM-R1; 5'-GCCGATTCATTAATG-CAGCTGG-3' (SEQ ID NO: 38). The PCR product was purified using the Qiaquick PCR Purification kit. This purified PCR product was inserted into the SwaI site of pCAGGS (BSX) to yield pCAGGS-SeV(m). Then, pSeV18+b(+)/ΔF-EGFP (Li, H.-O. et al. J. Virology 74, 2000, p 6564-6569) was digested with NotI and SalI, and separated by agarose gel electrophoresis. A band of 1972 bp was excised, purified using the Qiaquick Gel Extraction kit, and digested with NotI and SalI. The resulting fragment was ligated with purified pCAGGS-SeV(m) to yield pCAGGS-SeV(m)A. pSeV(+)18/ΔF was digested with NheI and KpnI and separated by agarose gel electrophoresis. A band of 3325 bp was excised, purified using the Qiaquick Gel Extraction kit, and digested with NotI and SalI. The resulting fragment was ligated with pCAGGS-SeV(m) to yield pCAGGS-SeV(m)AC.

pSeV18+b(+) (Li, H.-O. et al. J. Virology 74, 2000, p 6564-6569) was digested with SalI and NheI, and purified with the Qiaquick PCR purification kit. The resulting fragment was inserted into the SalI-NheI site of LITMUS38 (NEW ENGLAND BioLabs) to yield Litmus38/SeV Sal I-Nhe I. This Litmus38/SeV Sal I-Nhe I was digested with SalI and NheI and separated by agarose gel electrophoresis. A band of 9886 bp was excised and purified using the Qiaquick Gel Extraction kit. The DNA was inserted into the SalI-NheI site of pCAGGS-SeV(m)AC to yield pCAGGS-SeV.

pSeV/AF-EGFP (Li, H.-O. et al. J. Virology 74, 2000, p 6564-6569) was digested with SalI and NheI. The resulting fragment was purified with the Qiaquick PCR purification kit, and inserted into the SalI-NheI site of LITMUS38 (NEW ENGLAND BioLabs) to yield Litmus38/Sal I-Nhe IΔF-GFP. This Litmus38/Sal I-Nhe IΔF-GFP was digested with SalI and NheI and separated by agarose gel electrophoresis. A band of 8392 bp was then excised and purified using the Qiaquick Gel Extraction kit. The DNA was inserted into the SalI-NheI site of pCAGGS-SeV(m)AC to yield pCAGGS-SeV/ΔF-GFP.

Construction of pGEM-IRES-Luci

A luciferase fragment, which was obtained by digesting pMAMneo-Luci(Clontech) with BamHI, was inserted into the BamHI site of pTM1 (Nature, 348, 1, Nov., 1990, 91-92) to construct pGEM-IRES-Luci.

Example 2

Establishment of T7 RNA Polymerase-expressing BHK-21 (Hereinafter Referred to as BHK/T7)

Using a mammalian transfection kit (Stratagene) or SuperFect (Qiagen), BHK-21 cells (ATCC CCL-10) were transfected with pCALNdLWE-T7 that was constructed as described above. The cells were cultured for 2 weeks in D-MEM containing 400 µg/ml G418 at 37° C. under 5% $CO_2$, yielding drug-resistant clones grown from a single cell. The resulting drug-resistant clones were infected with recombinant adenovirus (AxCANCre) that expresses Cre DNA recombinase at an Moi of 4. After 24 hours, the cells were washed once with PBS and harvested. The expression of T7 RNA polymerase was confirmed by Western blotting analysis using a rabbit polyclonal anti-T7 RNA polymerase antibody.

Clones that were confirmed to express the T7 RNA polymerase were transfected with pGEM-IRES-Luci using SuperFect. The cells were harvested after 24 hours, and their luciferase activity was measured with MiniLumat LB9506 (EG&G BERTHOLD) using the Dual Luciferase Reporter System (Promega) kit to confirm the activity of the T7 RNA polymerase.

Example 3

Production of a Recombinant Sendai Virus by a Conventional Method

LLC-MK2 cells were plated at $5 \times 10^6$ cells/dish in 100-mm Petri dishes. After 24 hours of culture, the cells were washed once with serum-free MEM and infected at room temperature for 1 hour (moi=2) with a T7 RNA polymerase-expressing recombinant vaccinia virus (Fuerst, T. R. et al., Proc. Natl. Acad. Sci. USA 83, 8122-8126 (1986)) after the recombinant vaccinia virus was treated with 5 minutes of 3 µg/ml psoralen and long wavelength ultraviolet light (365 nm). The cells were washed twice with serum-free MEM. 12 µg/dish of the cDNA of an F-deficient Sendai virus vector carrying Lac Z (pSeV (+18:LacZ)ΔF), 4 µg/dish of pGEM/NP, 2 µg/dish of pGEM/P, 4 µg/dish of pGEM/L (Kato, A. et al., Genes Cells 1, 569-579(1996)), and 4 µg/dish of envelope plasmid pGEM/FHN are mixed, and then suspended in Opti-MEM (GIBCO). The SuperFect transfection reagent (1 µg DNA/5 µl of SuperFect; QIAGEN) was added and allowed to stand at room temperature for 15 minutes. The DNA-SuperFect mixture in 3 ml of Opti-MEM containing a final concentration of 3% FBS was added to the cells last. The cells were cultured for 3 hours. Then, the cells were washed twice with serum-free MEM, and cultured for 24 hours in MEM containing 40 µg/ml cytosine β-D-arabinofuranoside (AraC, Sigma) and 7.5 µg/ml trypsin. The culture supernatant was removed and a single 100-mm Petri dish of the F-expressing LLC-MK2/F7 cells (cells in which the F expression is induced are referred to as "LLC-MK2/F7/A"; Li, H.-O. et al., J. Virology 74. 6564-6569 (2000); WO 00/70070) were suspended in serum-free MEM (containing 40 µg/ml AraC and 7.5 µg/m trypsin), and 5 ml of this suspension was overlaid. After culturing for 48 hours, the cells and the supernatant were collected and used as P0-d3 samples. The pellet of P0-d3 was suspended in Opti-MEM ($2 \times 10^7$ cells/ml), and frozen and thawed three times. The sample was combined with the lipofection reagent DOSPER (Boehringer Mannheim) ($10^6$ cells/25 µl DOSPER), allowed to stand for 15 minutes at room temperature, and used to transfect the F-expressing LLC-MK2/F7 cell line (LLC-MK2/F7/A; $10^6$ cells/well in 24-well plate), which was then cultured in serum-free MEM (containing 40 µg/ml AraC and 7.5 µg/m trypsin). After 7 days of culture, the supernatant was collected as the P1-d7 sample. Then, cells of the F-expressing LLC-MK2/F7 cell line (LLC-MK2/F7/A) plated in 12-well plates were infected using the whole supernatant at 37° C. for one hour. The cells were then washed once with MEM, and cultured in serum-free MEM (containing 40 µg/ml AraC and 7.5 µg/ml trypsin). After 7 days of culture, the supernatant was collected as the P2-d7 sample. Then, cells of F-expressing LLC-MK2/F7 cell line (LLC-MK2/F7/A) plated in 6-well plates were infected using the whole supernatant at 37° C. for one hour. The cells were then washed once with MEM, and cultured in serun-free MEM (containing 7.5 µg/ml trypsin). After 7 days of culture, the supernatant was collected as the P3-d7 sample. Then, cells of the F-expressing LLC-MK2/F7 cell line (LLC-MK2/F7/A) plated in 10-cm plates were infected using the whole supernatant at 37° C. for one hour. The cells were then washed once with MEM, and cultured in serum-free MEM (containing 40 µg/ml AraC and 7.5 µg/ml trypsin). After 7 days of culture, the supernatant was collected as the P4-d7 sample.

Example 4

Method (1) for Recovering Sendai Virus Vectors Using a CA Promoter

Method for Recovering a Sendai Virus Vector that Uses a Sendai Virus Genome Having a Hammerhead Ribozyme Attached to pCAGGS (Hereinafter Referred to as the HamRbz Method)

4-1 [Recovery of a Transmissible SeV Vector]

Figure 12:
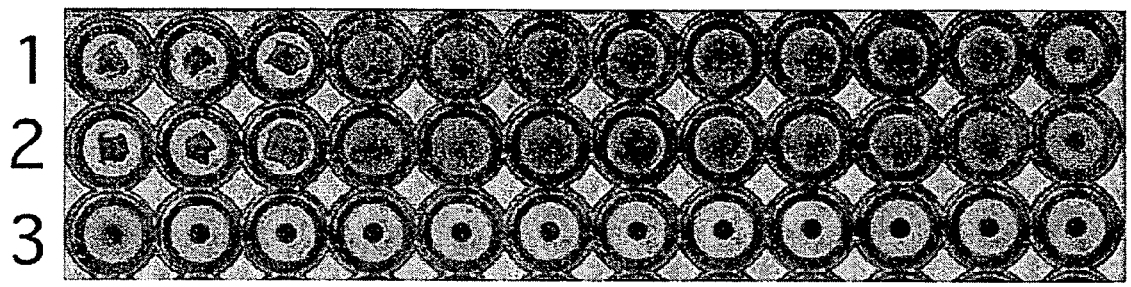
FIG. 12 is a photograph showing the result of an HA assay for a transmissible SeV vector harvested by the HamRbz method.

The day before transfection, 293T cells were plated onto 6-well plates at $1 \times 10^6$ cells/well in 2 ml of 10% FBS-containing D-MEM. The transfection was carried out by the procedure described below. 30 µl of Opti-MEM was combined with 15 µl of TransIT-LT1 (Mirus), and incubated at room temperature for 10 to 15 minutes. During the incubation, a DNA solution was prepared. 0.5 µg of pCAGGS-NP, 0.5 µg of pCAGGS-P4C(−), 2 µg of pCAGGS-L(TDK), and 2 µg of pCAGGS-SeV were dissolved in 20 µl of Opti-MEM. After 10 to 15 minutes, the DNA solution was combined with the TransIT-LT1 solution and allowed to stand at room temperature for 15 minutes. During this period, the cell culture medium was removed, and fresh 10% FBS-containing D-MEM was gently added at 1 ml/well. After 15 minutes, 500 µl of Opti-MEM (GIBCO) was added to the DNA-TransIT-LT1 mixture. The whole mixture was added to cells and cultured. After culturing for four days at 37° C. under 5% $CO_2$, the medium was discarded. The LLC-MK2/F7/A cells were suspended at $1 \times 10^6$ cells/ml in (serum-free) MEM containing 7.5 µg/ml trypsin (hereinafter referred to as "Try-MEM") and the suspension was overlaid at1 ml/well. The cells were cultured at 37° C. under 5% $CO_2$ for four days. Four days after overlaying the LLC-MK2/F7/A cells, the supernatant was collected and analyzed by an HA assay. The supernatant was found to be negative in HA. Thus, 100 µl of the collected supernatant was inoculated into each of the three hen eggs that had been incubated for 10 days. The eggs were incubated in an incubator at 35° C. for 3 days. Then, the chorioallantoic fluids were collected and analyzed by an HA assay. The result showed that the HA activity was detected in the chorioallantoic fluids collected from two of the three hen eggs. Thus, it was demonstrated that the wild-type Sendai virus vector could be recovered by the present method (FIG. 12).

4-2 [Recovery of an F-deficient SeV Vector]

The day before transfection, 293T cells were plated onto 6-well plates at $1 \times 10^6$ cells/well in 2 ml of 10% FBS-containing D-MEM. The transfection was carried out by the procedure described below. 30 µl of Opti-MEM was combined with 15 µl of TransIT-LT1 (Mirus), and incubated at room temperature for 10 to 15 minutes. A DNA solution was prepared during the incubation. 0.3 µg of pCAGGS-NP, 0.5 µg of pCAGGS-P4C(−), 2 µg of pCAGGS-L(TDK), 0.5 µg of pCAGGS-F5R, and 0.5 to 5 µg of pCAGGS-SeV/ΔF-GFP were dissolved in 20 µl of Opti-MEM. After 10 to 15 minutes, the DNA solution was combined with the TransIT-LT1 solution and allowed to stand at room temperature for 15 minutes. During this period, the cell culture medium was removed, and fresh 10% FBS-containing D-MEM was gently added at 1 ml/well. After 15 minutes, 500 µl of Opti-MEM (GIBCO) was added to the DNA-TransIT-LT1 mixture. The whole mixture was added to cells following by culturing. After culturing at 37° C. under 5% $CO_2$ for 72 hours, the medium was discarded. The LLC-MK2/F7/A cells were suspended at $1 \times 10^6$ cells/ml in (serum-free) MEM containing 7.5 µg/ml trypsin (hereinafter referred to as "Try-MEM") and the suspension was overlaid at 1 ml/well. The cells were cultured at 37° C. under 5% $CO_2$. After 24 hours, 1 ml of the culture medium was collected and 1 ml of fresh Try-MEM was added. The cells were cultured at 37° C. under 5% $CO_2$. After 48 hours, 1 ml of the culture medium was collected and 1 ml of fresh Try-MEM was added. The cells were cultured at 37° C. under 5% $CO_2$. After 72 hours, 1 ml of the culture medium was collected. 133 µl of 7.5% BSA (final concentration: 1% BSA) was added to the collected culture media, and stored at −80° C. prior to CIU measurement.

4-3 [CIU Determination by Counting GFP-expressing Cells (GFP-CIU)]

Figure 13:
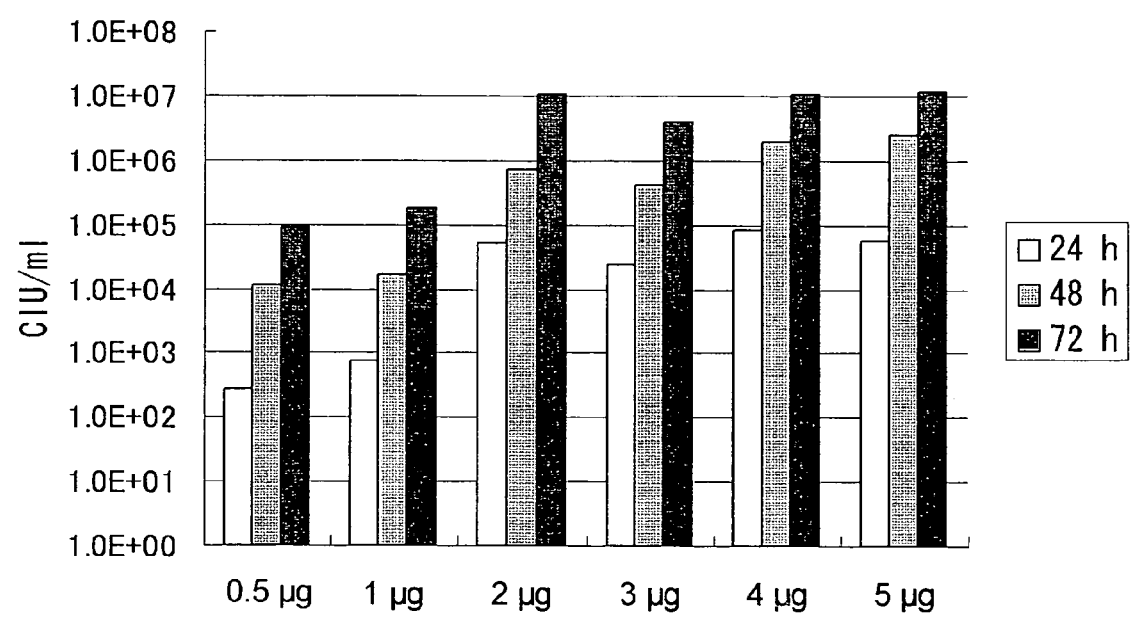
FIG. 13 shows the result of examining the recovery efficiency of SeV/ΔF-GFP by CIU assay, using varied amounts of genome DNA in the HamRbz method. The efficiency remained almost unchanged when 2 µg or more of the genome DNA was used.

2 to 3 days before a CIU assay, LLC-MK2 cells were plated onto 12-well plates. When plated 2 days before the assay, the cells were plated at a cell density of $1.5 \times 10^5$ cells/well in 10% FBS-containg MEM (1 ml/well). When plated 3 days before the assay, the cells were plated at a cell density of $8.0 \times 10^4$ cells/well in 10% FBS-containing MEM (1 m/well). On the day of CIU assay, the cells were washed once with serum-free MEM. Ten-fold serial dilutions of the culture medium collected 24, 48, and 72 hours after overlaying the cells were prepared using MEM. After one hour of infection at 37° C., the cells were washed once with MEM and 1 ml of MEM was added thereto. After 2 days of culture at 37° C., the cells were observed under a fluorescence microscope to count GFP-positive cells in appropriated diluted wells. As a result, $1 \times 10^5$ to $1 \times 10^7$ GFP-CIU/ml of the viral vector was found to be recovered 72 hours after overlaying the cells (FIG. 13).

4-4 [Improvement of Productivity by Supplying F Introduced with a Furin Recognition Sequence (Hereinafter Referred to as "F5R"), as Compared with Wild-type F (Hereinafter Referred to as "F")]

The reconstitution efficiency of supplying the F protein using pCAGGS was compared between the wild-type F gene and furin recognition sequence-introduced F5R. 293T cells were plated onto 6-well plates at $1 \times 10^6$ cells/well in 2 ml of 10% FBS-containing D-MEM the day before transfection. The transfection was carried out by the procedure described below. 15 µl of TransIT-LT1 (Mirus) was combined with 30 µl of Opti-MEM, and incubated at room temperature for 10 to 15 minutes. A DNA solution was prepared during the incubation. Fixed amounts of pCAGGS-NP (0.3 µg), pCAGGS-P4C(−)

Figure 14:
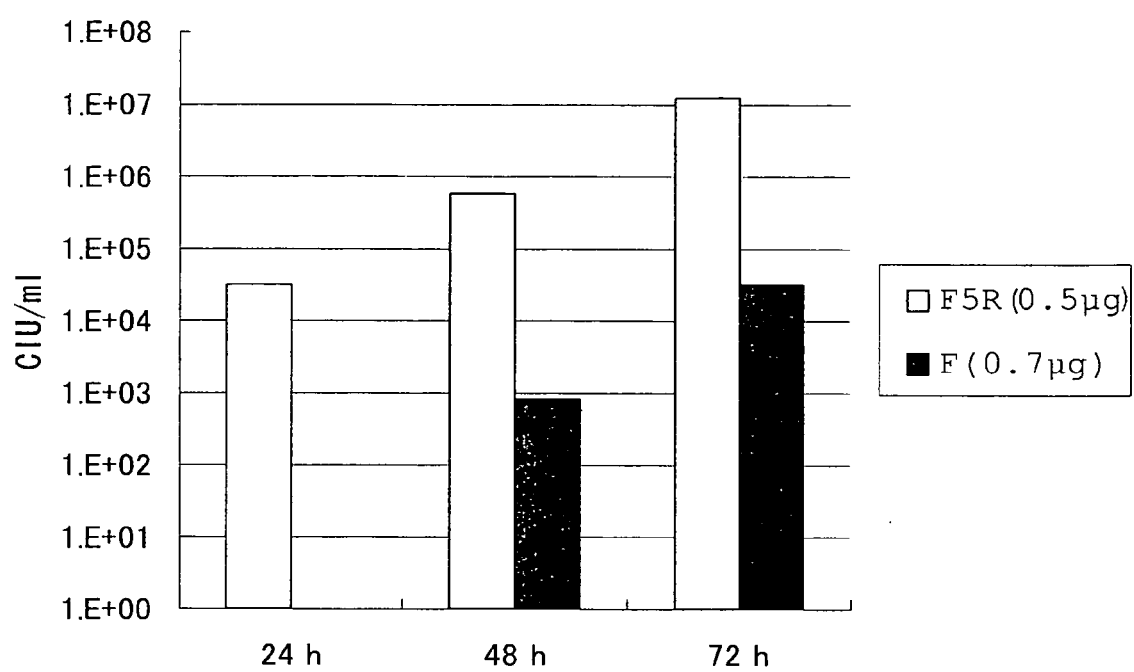
FIG. 14 shows the result of examining the recovery efficiency of SeV/ΔF-GFP when the recovery was carried out by the HamRbz method using pCAGGS-F and pCAGGS-F5R. The recovery efficiency was considerably improved by using pCAGGS-F5R.

(0.5 µg), pCAGGS-L (2 µg), and pCAGGS-SeV/∆F-GFP (2 µg), and various amounts of pCAGGS-F or pCAGGS-F5R (0.1, 0.3, 0.5, 0.7, and 0.9 µg) were dissolved in 20 µl of Opti-MEM. After 10 to 15 minutes, a DNA solution was combined with the TransIT-LT1 solution and allowed to stand at room temperature for 15 minutes. During this period, the cell culture medium was removed, and fresh 10% FBS-containing D-MEM was gently added at 1 ml/well. After 15 minutes, 500 µl of Opti-MEM (GIBCO) was added to the DNA-TransIT-LT1 mixture. The whole mixture was added to cells and cultured. After culturing at 37° C. under 5% $CO_2$ for 72 hours, the culture medium was discarded, and the LLC-MK2/F7/A cells were suspended at $1 \times 10^6$ cells/ml in (serum-free) MEM containing 7.5 µg/ml trypsin (hereinafter referred to as "Try-MEM") and the suspension was overlaid at 1 ml/well. The cells were cultured at 37° C. under 5% $CO_2$. After 24 hours, 1 ml of the culture medium was collected, and 1 ml of fresh Try-MEM was added. The cells were cultured at 37° C. under 5% $CO_2$. After 48 hours, 1 ml of the culture medium was collected and 1 ml of fresh Try-MEM was added. The cells were cultured at 37° C. under 5% $CO_2$. After 72 hours, 1 ml of the culture medium was collected. 133 µl of 7.5% BSA (final concentration: 1% BSA) was added to the collected culture medium, and stored at −80° C. prior to CIU measurement. CIU assays were carried out after all samples were collected. As a result, when pCAGGS-F was used, the reconstitution efficiency was found to be the highest at 0.7 µg. The samples collected 24, 48, and 72 hours following the cell overlay contained 0, $7.9 \times 10^2$, and $3.3 \times 10^4$ CIU/ml of viral vectors, respectively. Meanwhile, when pCAGGS-F5R was used, the reconstitution efficiency was found to be the highest at 0.5 µg. The samples collected 24, 48, and 72 hours following the cell overlay contained $3.2 \times 10^4$, $5.7 \times 10^5$, and $1.2 \times 10^7$ CIU/ml of viral vectors, respectively. A comparison of the two in conditions of the highest reconstitution efficiency, pCAGGS-F5R gave a much higher reconstitution efficiency than pCAGGS-F, and yielded 373 times more viral vectors at 72 hours after the cell overlay (FIG. 14).

Example 5

Method (2) for Recovering Sendai Virus Vectors Using a CA Promoter

Figure 15:
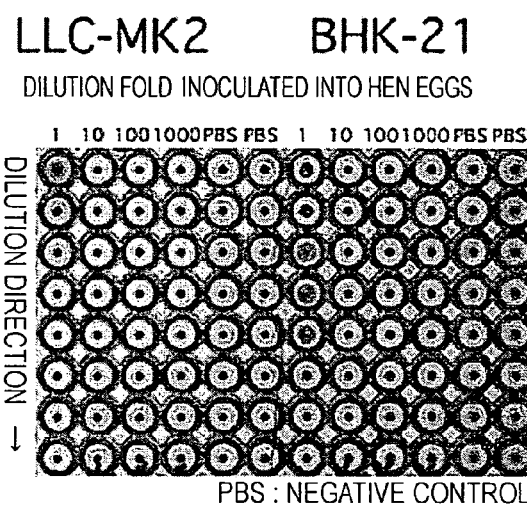
FIG. 15 is a set of photographs showing the result of an HA assay for transmissible SeV (SeV(TDK)18+GFP) recovered by the pCAGGS-T7 method. HA activity was detected only when undiluted BHK-21, BHK/T7, and 293T was inoculated into hen eggs.
Figure 15:
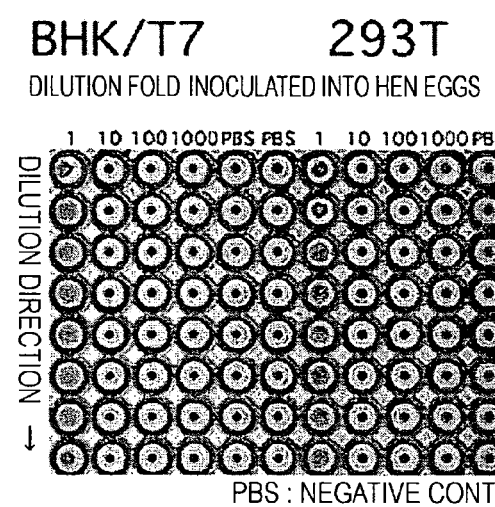
Figure 16:
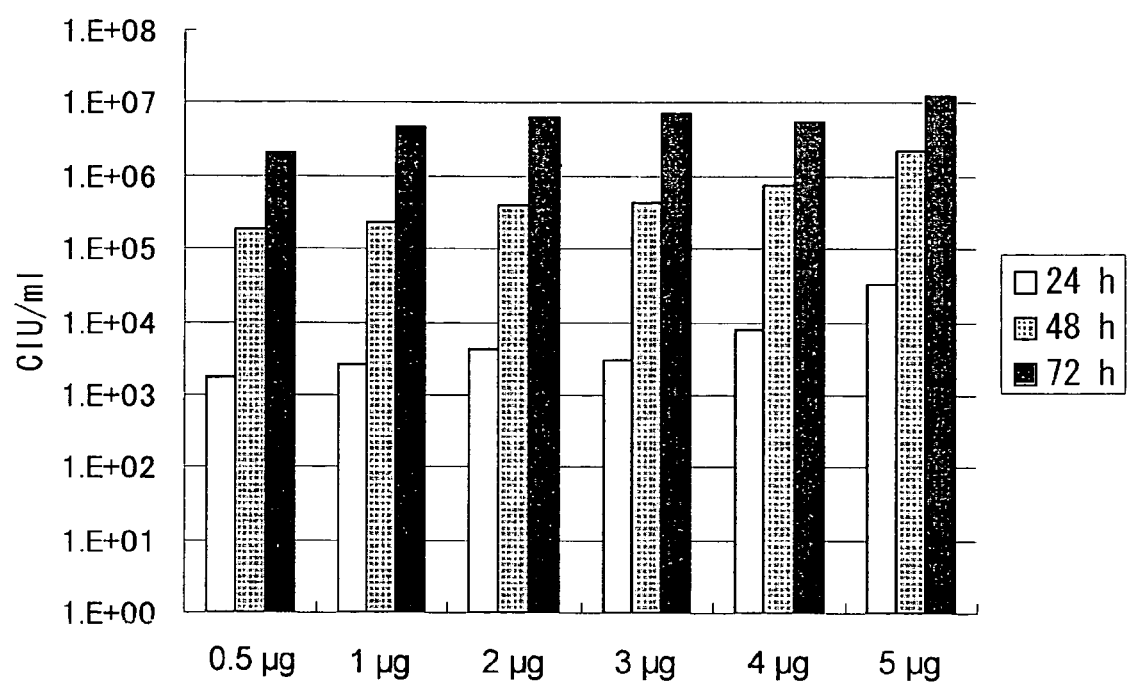
FIG. 16 shows the result of examining the recovery efficiency of SeV/ΔF-GFP by CIU assay using varied amounts of genome DNA in the pCAGGS-T7 method. The recovery efficiency remained almost unchanged when 0.5 to 5.0 µg of genome DNA was used, although it was the highest when 5 µg of the genome DNA was used.
Figure 17:
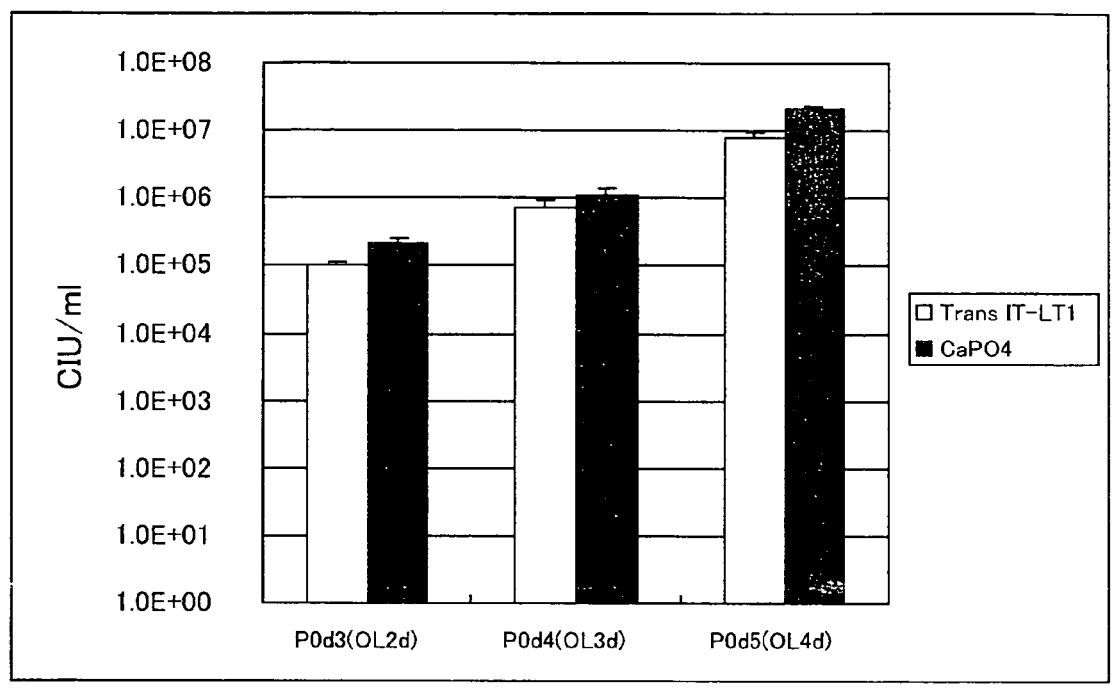
FIG. 17 shows the result of examining the recovery efficiency of SeV18+GFP/ΔF by CIU assay, by changing the transfer reagent used in the pCAGGS-T7 method. The recovery efficiency obtained using calcium phosphate was found to be equal to or higher than that obtained using TransIT-LT-1.

Method for Recovering Sendai Virus Vectors Using pCAGGS-T7 (Hereinafter Referred to as the pCAGGS-T7 Method)
5-1 [Recovery of Transmissible SeV Vectors]
The day before transfection, each cell line was plated onto 6-well plates (293T cell: $1 \times 10^6$ cells/well/2 ml 10% FBS-containing D-MEM; LLC-MK2 cell: $5.0 \times 10^5$ cells/well in 2 ml of 10% FBS-containing D-MEM; BHK-21 cell: $2.5 \times 10^5$ cells/well in 2 ml of 10% FBS-containing D-MEM; BHK/T7 cell: $2.5 \times 10^5$ cells/well in 2 ml of 10% FBS-containing D-MEM). The transfection was carried out by the procedure described below. 30 µl of Opti-MEM was combined with 15 µl of TransIT-LT1 (Mirus) and incubated at room temperature for 10 to 15 minutes. A DNA solution was prepared during the incubation. 0.5 µg of pCAGGS-T7, 0.5 µg of pCAGGS-NP, 0.5 µg of pCAGGS-P4C(−), 2 µg of pCAGGS-L(TDK), and 5 µg of pSeV(TDK)18+GFP were dissolved in 20 µl of Opti-MEM. After 10 to 15 minutes, the DNA solution was combined with the TransIT-LT1 solution and allowed to stand at room temperature for 15 minutes. During this period, the cell culture medium was removed, and fresh 10% FBS-containing D-MEM was gently added at 1 ml/well. After 15 minutes, 500 µl of Opti-MEM (GIBCO) was added to the DNA-TransIT-LT1 mixture. After the whole mixture was added to cells, they were cultured at 37° C. under 5% $CO_2$ for 3 days. Then, GFP-positive cells were counted, and the results were: 293T: 246 cells; LLC-MK2: 16 cells; BHK-21: 288 cells; and BHK/T7: 405 cells. Then, the culture medium was discarded, and 1 ml of PBS(−) was added to the cells. The cells were scraped using a cell scraper and collected in Eppendorf tubes. After freeze-thawing once, 100 µl of undiluted cell suspensions and cell suspensions diluted 10, 100, and 1000 times with PBS(−) were inoculated into 10-day hen eggs. The eggs were incubated in an incubator at 35° C. for 3 days. Then, the chorio-allantoic fluids were collected and analyzed by an HA assay. As a result, viral propagation was detected in the hen eggs inoculated with undiluted suspensions of 293T cells, BHK-21 cells, and BHK/T7 cells (FIG. 15).
5-2 [Recovery of F-deficient SeV Vectors]
293T cells were plated onto 6-well plates at $1 \times 10^6$ cells/well in 2 ml of 10% FBS-containing D-MEM the day before transfection. The transfection was carried out by the procedure described below. 30 µl of Opti-MEM was combined with 15 µl of TransIT-LT1 (Mirus), and incubated at room temperature for 10 to 15 minutes. A DNA solution was prepared during the incubation. 0.5 µg of pCAGGS-T7, 0.5 µg of pCAGGS-NP, 0.5 µg of pCAGGS-P4C(−), 2 µg of pCAGGS-L(TDK), 0.5 µg of pCAGGS-F5R, and 0.5 to 5 µg of pSeV/∆F-GFP (WO 00/70070) were dissolved in 20 µl of Opti-MEM. After 10 to 15 minutes, the DNA solution was combined with the TransIT-LT1 solution and allowed to stand at room temperature for 15 minutes. During this period, the cell culture medium was removed, and fresh 10% FBS-containing D-MEM was gently added at 1 ml/well. After 15 minutes, 500 µl of Opti-MEM (GIBCO) was added to the DNA-TransIT-LT1 mixture. The whole mixture was added to the cells and cultured. After culturing at 37° C. under 5% $CO_2$ for 72 hours, the culture medium was discarded, and the LLC-MK2/F7/A cells were suspended at $1 \times 10^6$ cells/ml in Try-MEM and the suspension was overlaid at 1 ml/well. The cells were cultured at 37° C. under 5% $CO_2$. After 24 hours, 1 ml of the culture medium was collected, and 1 ml of fresh Try-MEM was added. The cells were cultured at 37° C. under 5% $CO_2$. After 48 hours, 1 ml of the culture medium was collected, and 1 ml of fresh Try-MEM was added. The cells were cultured at 37° C. under 5% $CO_2$. After 72 hours, 1 ml of the culture medium was collected. 133 µl of 7.5% BSA (final concentration: 1% BSA) was added to the collected culture medium, and stored at −80° C. prior to CIU measurement.
5-3 [CIU Determination by Counting GFP-expressing Cells (GFP-CIU)]
2 to 3 days before a CIU assay, the LLC-MK2 cells were plated onto 12-well plates. When plated 2 days before the assay, the cells were plated at $1.5 \times 10^5$ cells/well in 1 ml/well of 10% FBS-containing MEM. When plated 3 days before the assay, the cells were plated at $8.0 \times 10^4$ cells/well in 1 ml/well of 10% FBS-containing MEM. On the day of CIU assay, the cells were washed once with serum-free MEM. Ten-fold serial dilutions of the culture media collected 24, 48, and 72 hours after the cell overlay were prepared using MEM. After one hour of infection at 37° C., the cells were washed once with MEM and 1 ml of MEM was added thereto. After 2 days of culture at 37° C., the cells were observed under a fluorescence microscope to count GFP-positive cells in adequately diluted wells. As a result, $1 \times 10^6$ to $1 \times 10^7$ GFP-CIU/ml of the viral vector was found to be recovered 72 hours after the cell overlay (FIG. 16).
In the pCAGGS-T7 method, SeV18+GFP/∆F was also successfully recovered by the calcium phosphate method when 293T cells are used for introduction of the plasmid. The efficiency was comparable to or higher than that of TransIT-LT1 (FIG. 17).

Example 6

Evaluation of Cell Types Used for the pCAGGS-T7 Method

Figure 18:
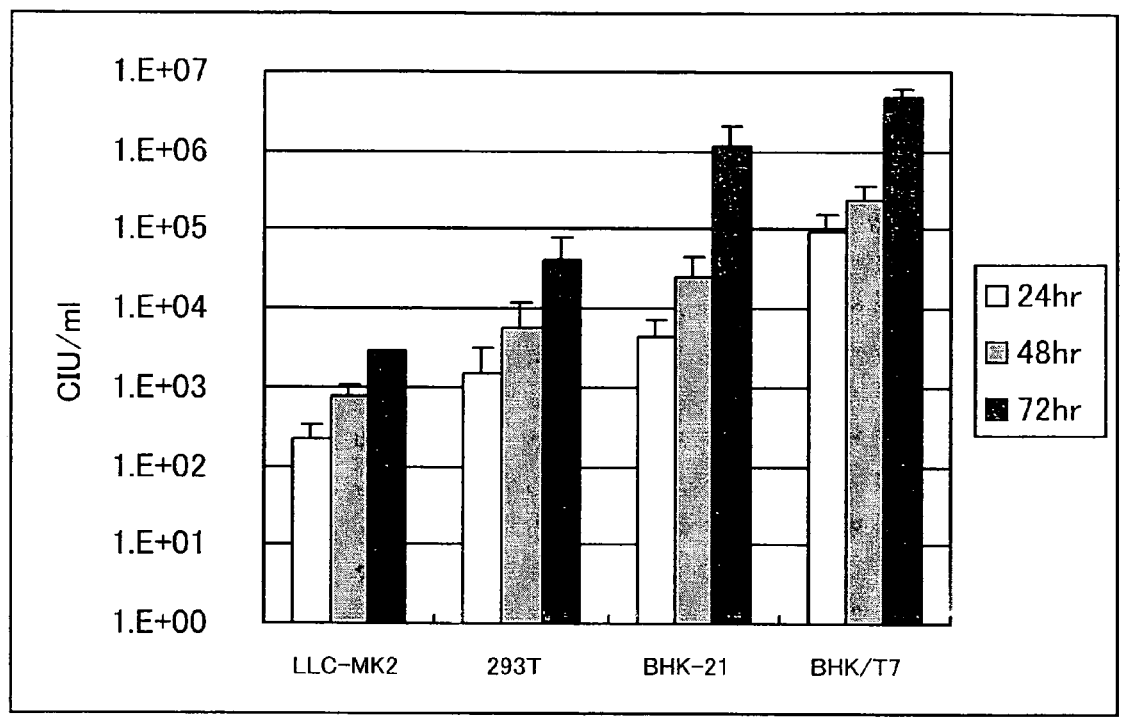
FIG. 18 shows the result of examining the recovery efficiency of SeV/ΔF-GFP by CIU assay by changing the cell type used in the pCAGGS-T7 method. Viruses were recovered from all the cell types tested. The recovery efficiency was in the order of: BHK/T7>BHK-21>293T>LLC-MK2. (Note that pCAGGS-T7 was not added when BHK/T7 was used.)

To assess whether the pCAGGS-T7 method can recover Sendai virus vectors by using cell lines other than 293T, it was tested whether the vector could be harvested using the LLC-MK2, BHK-21, BHK/T7, or 293T cell line. The day before transfection, each cell line was plated onto 6-well plates (LLC-MK: $5 \times 10^5$ cells/well; BHK-21: $2.5 \times 10^5$ cells/well; BHK/T7: $2.5 \times 10^5$ cells/well; 293T: $1.0 \times 10^6$ cells/well). The transfection was carried out by the procedure described below. 30 μl of Opti-MEM was combined with 15 μl of TransIT-LT1 (Mirus), and incubated at room temperature for 10 to 15 minutes. A DNA solution was prepared during the incubation. 0.5 μg of pCAGGS-T7, 0.5 μg of pCAGGS-NP, 0.5 μg of pCAGGS-P4C(−), 2 μg of pCAGGS-L(TDK), 0.5 μg of pCAGGS-F5R, and 2 μg of pSeV/ΔF-GFP were dissolved in 20 μl of Opti-MEM (however, pCAGGS-T7 was not added when BHK/T7 cells were used). After 10 to 15 minutes, the DNA solution was combined with the TransIT-LT1 solution and allowed to stand at room temperature for 15 minutes. During this incubation, the cell culture medium was removed, and fresh 10% FBS-containing D-MEM was gently added at 1 ml/well. After 15 minutes, 500 μl of Opti-MEM (GIBCO) was added to the DNA-TransIT-LT1 mixture. The whole mixture was added to cells and cultured. After culturing at 37° C. under 5% $CO_2$ for 72 hours, the culture medium was discarded, and the LLC-MK2/F7/A cells were suspended at $1 \times 10^6$ cells/ml in Try-MEM and the suspension was overlaid at 1 ml/well. The cells were cultured at 37° C. under 5% $CO_2$. After 24 hours, 1 ml of the culture medium was collected, and 1 ml of fresh Try-MEM added to the cells. The cells were cultured at 37° C. under 5% $CO_2$. After 48 hours, 1 ml of the culture medium was collected, and 1 ml of fresh Try-MEM was added to the cells. The cells were cultured at 37° C. under 5% $CO_2$. After 72 hours, 1 ml of the culture medium was collected. 133 μl of 7.5% BSA (final concentration: 1% BSA) was added to the collected culture medium, and stored at −80° C. prior to CIU measurement. It was found that the vector could be recovered with all the cell types tested (n=3). The vector recovery rate was in the order of high to low: BHK/T7 cell>BHK-21 cell>293T cell>LLC-MK2 cell (FIG. 18). Since BHK/T7 was not transfected with pCAGGS-T7, it was demonstrated that F-deficient SeV/ΔF-GFP could also be recovered using a CA promoter in T7-expressing cell lines.

Example 7

Comparison of the HamRbz Method and pCAGGS-T7 Method

The day before transfection, 293T cells were plated onto 6-well plates at $1 \times 10^6$ cells/well in 2 ml of 10% FBS-containing D-MEM. The transfection was carried out by the procedure described below. 30 μl of Opti-MEM was combined with 15 μl of TransIT-LT1 (Mirus), and incubated at room temperature for 10 to 15 minutes. A DNA solution was prepared during the incubation. 0.3 μg of pCAGGS-NP, 0.5 μg of pCAGGS-P4C(−), 2 μg of pCAGGS-L(TDK), 0.5 μg of pCAGGS-F5R, and 5 μg of pCAGGS-SeV/ΔF-GFP were dissolved in 20 μl of Opti-MEM. After 10 to 15 minutes, the DNA solution was combined with the TransIT-LT1 solution and allowed to stand at room temperature for 15 minutes. During this period, the cell culture medium was removed, and fresh 10% FBS-containing D-MEM was gently added at 1 ml/well. After 15 minutes, 500 μl of Opti-MEM (GIBCO) was added to the DNA-TransIT-LT1 mixture. The whole mixture was added to cells and cultured. After culturing at 37° C. under 5% $CO_2$ for 72 hours, the culture medium was discarded, and the LLC-MK2/F7/A cells were suspended at $1 \times 10^6$ cells/ml in (serum-free) MEM containing 7.5 μg/ml trypsin (hereinafter referred to as "Try-MEM") and the suspension was overlaid at 1 ml/well. The cells were cultured at 37° C. under 5% $CO_2$. After 24 hours, 1 ml of the culture medium was collected, and 1 ml of fresh Try-MEM was added. The cells were cultured at 37° C. under 5% $CO_2$. After 48 hours, 1 ml of the culture medium was collected, and 1 ml of fresh Try-MEM was added. The cells were cultured at 37° C. under 5% $CO_2$. After 72 hours, 1 ml of the culture medium was collected. 133 μl of 7.5% BSA (final concentration: 1% BSA) was added to the collected culture medium and stored at −80° C. prior to CIU measurement.

Figure 19:
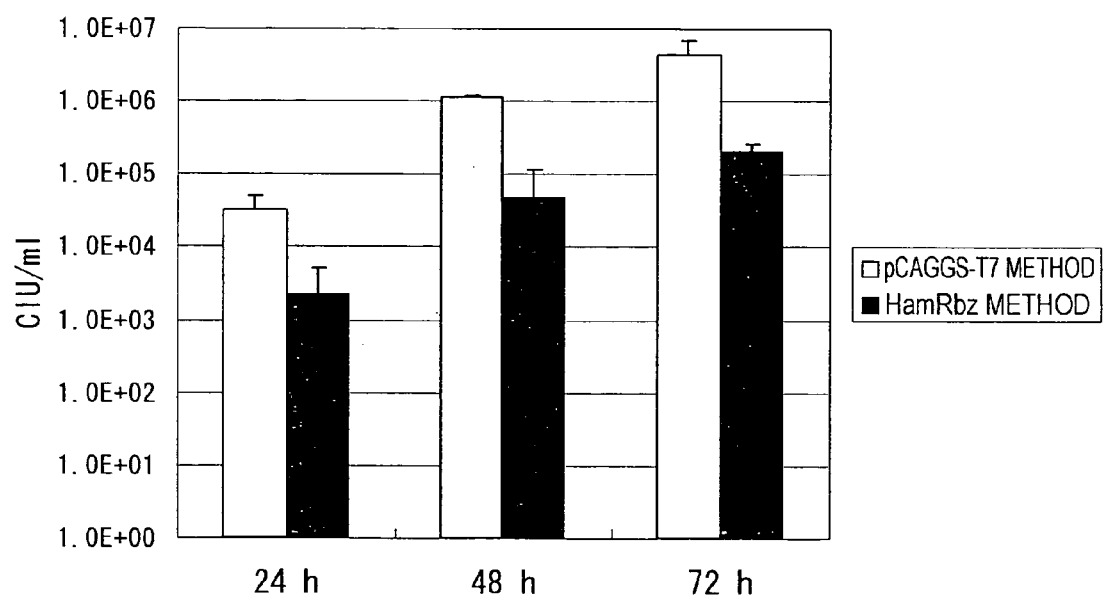
FIG. 19 shows the result of comparing the recovery efficiency of SeV/ΔF-GFP between the HamRbz method and the pCAGGS-T7 method by CIU assay. The pCAGGS-T7 method showed higher reconstitution efficiency than the HamRbz method.

For pCAGGS-T7 method, 293T cells were plated onto 6-well plates at $1 \times 10^6$ cells/well in 2 ml of 10% FBS-containing D-MEM the day before transfection. The transfection was carried out by the procedure described below. 30 μl of Opti-MEM was combined with 15 μl of TransIT-LT1 (Mirus), and incubated at room temperature for 10 to 15 minutes. A DNA solution was prepared during the incubation. 0.5 μg of pCAGGS-T7, 0.5 μg of pCAGGS-NP, 0.5 μg of pCAGGS-P4C(−), 2 μg of pCAGGS-L(TDK), 0.5 μg of pCAGGS-FSR, and 5 μg of pSeV/ΔF-GFP were dissolved in 20 μl of Opti-MEM. After 10 to 15 minutes, the DNA solution was combined with the TransIT-LT1 solution and allowed to stand at room temperature for 15 minutes. During this period, the cell culture medium was removed, and 1 ml/well of fresh 10% FBS-containing D-MEM was gently added. After 15 minutes, 500 μl of Opti-MEM (GIBCO) was added to the DNA-TransIT-LT1 mixture. The whole mixture was added to cells and cultured. After culturing at 37° C. under 5% $CO_2$ for 72 hours, the culture medium was discarded, and the LLC-MK2/F7/A cells were suspended at $1 \times 10^6$ cells/ml in Try-MEM and the suspension was overlaid at 1 ml/well. The cells were cultured at 37° C. under 5% $CO_2$. After 24 hours, 1 ml of the culture medium was collected, and 1 ml of fresh Try-MEM was added. The cells were cultured at 37° C. under 5% $CO_2$. After 48 hours, 1 ml of the culture medium was collected, and 1 ml of fresh Try-MEM was added. The cells were cultured at 37° C. under 5% $CO_2$. After 72 hours, 1 ml of the culture medium was collected. 133 μl of 7.5% BSA (final concentration: 1% BSA) was added to the collected culture medium, and stored at −80° C. prior to CIU measurement. The results of CIU measurement showed that the reconstitution efficiency was higher with the pCAGGS-T7 method than with the HamRbz method (FIG. 19).

Example 8

Figure 20:
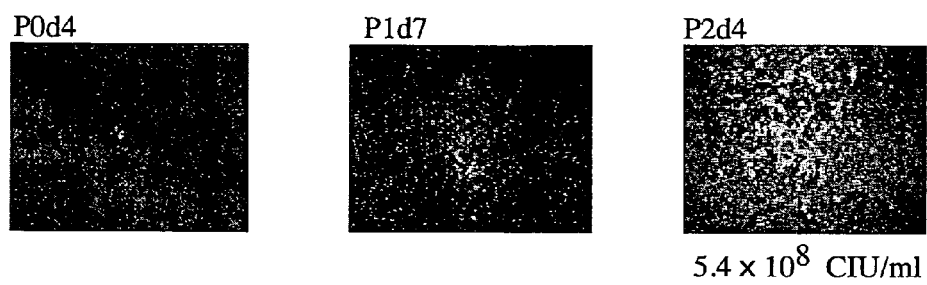
FIG. 20 shows the reconstitution of SeV/ΔM-GFP by the pCAGGS-T7 method.

Construction of an M Gene-deficient Vector and a Vector Deficient in M and F Genes An M gene-deficient Sendai virus vector (SeV/ΔM), and a Sendai virus vector deficient in M and F genes (SeV/ΔMΔF-GFP) were reconstituted using the pCAGGS-T7 method. Reconstitution of an SeV/ΔM Vector 293T cells were plated onto 6-well plates at $1 \times 10^6$ cells/well in 2 ml of 10% FBS-containing D-MEM the day before transfection. The transfection was carried out by the procedure described below. 30 μl of Opti-MEM was combined with 15 μl of TransIT-LT1 (Mirus), and incubated at room temperature for 10 to 15 minutes. A DNA solution was prepared during the incubation. 0.5 μg of pCAGGS-NP, 0.5 μg of pCAGGS-P4C(−), 2 μg of pCAGGS-L(TDK), 1.0 μg of pCAGGS-M, 0.5 μg of pCAGGS-T7, and 5 μg of pSeV/ΔM-GFP were dissolved in 20 μl of Opti-MEM. After 10 to 15 minutes, the DNA solution was combined with the TransIT-LT1 solution, and allowed to stand at room temperature for 15 minutes. During this period, the cell culture medium was removed, and 1 ml of fresh 10% FBS-containing D-MEM was gently added. After 15 minutes, 500 μl of Opti-MEM (GIBCO) was added to the DNA-TransIT-LT1 mixture. The whole mixture was added to the cells and cultured. After culturing at 37° C. under 5% $CO_2$ for 72 hours, the culture medium was discarded, and LLC-MK2 cells expressing both the Sendai virus M and F genes (hereinafter referred to as LLC-M/F) were suspended at $1 \times 10^6$ cells/ml in (serum-free) MEM containing 7.5 μg/ml trypsin (herein after referred to as "Try-MEM") and the suspension was overlaid at 1 ml/well. The cells were incubated at 37° C. under 5% $CO_2$. After the cell overlay, the culture medium was exchanged with fresh Try-MEM every day for three days. Thereafter, the medium was changed every 2 to 3 days. On day 9 after the transfection, the culture medium was added to freshly prepared LLC-MK2-M/F cells. The cells were cultured at 32° C. under 5% $CO_2$ for 9 days (the medium was changed every 2 to 3 days). The supernatant was added to freshly prepared LLC-MK2-M/Fcells, and cultured for four days in the same way. This culture supernatant was found to contain $5.4 \times 10^8$ CIU/ml of SeV/ΔM-GFP vector. The expansion of vector-infected cells in cells cultured for 4 days after the transfection (P0d4), cells cultured for 7 days after the first passage (P1d7), or cells cultured for four days after the second passage (P2d4) was observed using GFP fluorescence. The results are shown in FIG. 20.

Figure 21:
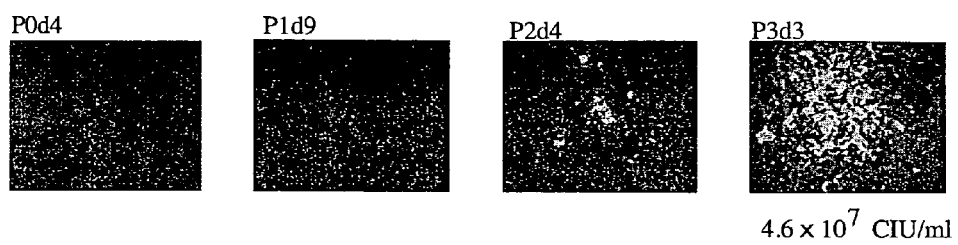
FIG. 21 shows the reconstitution of SeV/ΔMΔF-GFP by the pCAGGS-T7 method.
Figure 22:
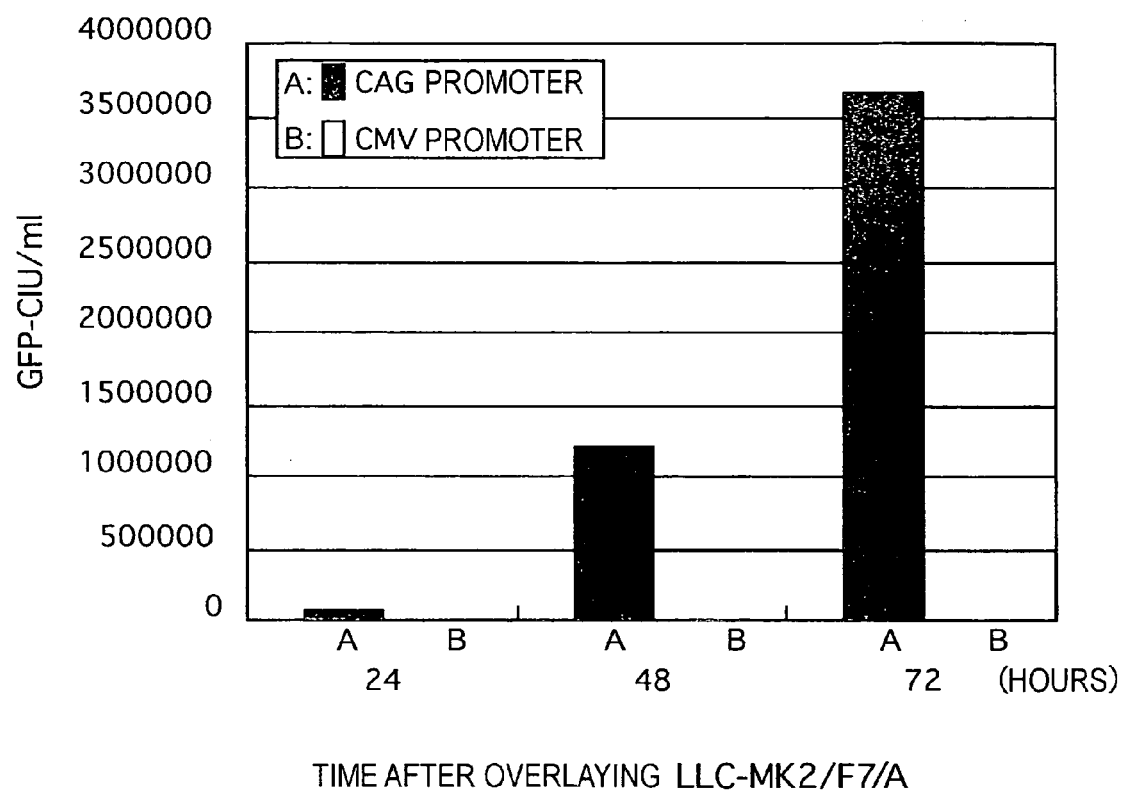
FIG. 22 shows the result of comparing vector reconstitution between using a CMV promoter and a CA promoter. The efficiency of vector reconstitution is overwhelmingly high with a CA promoter.

Reconstitution of SeV/ΔMΔF-GFP 293T cells were plated onto 6-well plates at $1 \times 10^6$ cells/well in 2 ml of 10% FBS-containing D-MEM the day before transfection. The transfection was carried out by the procedure described below. 15 μl of TransIT-LT1 (Mirus) was combined with 30 μl of Opti-MEM, and incubated at room temperature for 10 to 15 hours. A DNA solution was prepared during the incubation. 0.5 μg of pCAGGS-NP, 0.5 μg of pCAGGS-P4C(−), 2 μg of pCAGGS-L(TDK), 0.5 μg of pCAGGS-F5R, 1.0 μg of pCAGGS-M, 0.5 μg of pCAGGS-T7, and 5 μg of pSeV/ΔMΔF-GFP were dissolved in 20 μl of Opti-MEM. After 10 to 15 minutes, the DNA solution was combined with the TransIT-LT1 solution and allowed to stand at room temperature for 15 minutes. During this period, the cell culture medium was removed, and 1 ml of fresh 10% FBS-containing D-MEM was gently added. After 15 minutes, 500 μl of Opti-MEM (GIBCO) was added to the DNA-TransIT-LT1 mixture. The whole mixture was added to the cells followed by culturing. After culturing at 37° C. under 5% $CO_2$ for 72 hours, the culture medium was discarded, and LLC-M/F was suspended at $1 \times 10^6$ cells/ml in (serum-free) MEM containing 7.5 μg/ml trypsin (hereinafter referred to as "Try-MEM") and the suspension was overlaid at 1 ml/well. The cells were cultured at 37° C. under 5% $CO_2$. After the cell overlay, the culture medium was exchanged with fresh Try-MEM every day for 3 days. Thereafter, the medium was changed every 2 to 3 days. On day 9 after transfection, the culture medium was added to freshly prepared LLC-M/F cells. The cells were cultured at 32° C. under 5% $CO_2$ for 9 days (medium was changed every 2 to 3 days). The supernatant was added to freshly prepared LLC-M/F cells and cultured for four days in the same way. Furthermore, the supernatant was added to freshly prepared LLC-M/F cells and cultured for 3 days in the same way. This culture supernatant was found to contain $4.6 \times 10^7$ CIU/ml of SeV/ΔMΔF-GFP vector. The expansion of vector-infected cells in cells cultured for four days after transfection (P0d4), cells cultured for 9 days after the first passage (P1d9), cells cultured for four days after the second passage (P2d4), or cells cultured for 3 days after the third passage (P3d3) was observed using GFP fluorescence. The results are shown in FIG. 21.

Example 9

Comparison of the Reconstitution Efficiency of CA and CMV Promoters

To compare the CMV and CA promoters, NP, P, L, F5R, and T7 RNA polymerase under the control of a CMV promoter were loaded into pCI-neo (Promega) (pCI-neo-NP, pCI-neo-P4C(−), pCI-neo-L(TDK), pCI-neo-F5R, and pCI-neo-T7, respectively). The day before transfection, 293T cells were plated onto 6-well plates at $1 \times 10^6$ cells/well in 2 ml of 10% FBS-containing D-MEM. The transfection was carried out by the procedure described below. 15 μl of TransIT-LT1 (Mirus) was combined with 30 μl of Opti-MEM and incubated at room temperature for 10 to 15 minutes. A DNA solution was prepared during the incubation. When a CA promoter (pCAGGS plasmid) was used, 0.5 μg of pCAGGS-NP, 0.5 μg of pCAGGS-P4C(−), 2 μg of pCAGGS-L(TDK), 0.5 μg of pCAGGS-F5R, 0.5 μg of pCAGGS-T7, and 5 μg of pSeV/ΔF-GFP were dissolved in 20 μl of Opti-MEM. When a CMV promoter (pCI-neo) was used, 0.5 μg of pCI-neo-NP, 0.5 μg of pCI-neo-P4C(−), 5 μg of pCI-neo-L(TDK), 0.5 μg of pCI-neo-F5R, 1 μg of pCI-neo-T7, and 5 μg of pSeV/ΔF-GFP were dissolved in 20 μl of Opti-MEM. After 10 to 15 minutes, the DNA solution was combined with the TransIT-LT1 solution and allowed to stand at room temperature for 15 minutes. During this period, the cell culture medium was removed, and 1 ml of fresh 10% FBS-containing D-MEM was gently added. After 15 minutes, 500 μl of Opti-MEM (GIBCO) was added to the DNA-TransIT-LT1 mixture. The whole mixture was added to the cells and cultured. After culturing at 37° C. under 5% $CO_2$ for 72 hours, the culture medium was discarded, and the LLC-MK2/F7/A cells were suspended at $1 \times 10^6$ cells/ml in (serum-free) MEM containing 7.5 μg/ml trypsin (hereinafter referred to as "Try-MEM") and the suspension was overlaid at 1 ml/well. The cells were cultured at 37° C. under 5% $CO_2$. After 24 hours, 1 ml of the culture medium was collected, and 1 ml of fresh Try-MEM was added. The cells were cultured at 37° C. under 5% $CO_2$. After 48 hours, 1 ml of the culture medium was collected, and 1 ml of fresh Try-MEM was added. The cells were cultured at 37° C. under 5% $CO_2$. After 72 hours, 1 ml of the culture medium was collected. 133 μl of 7.5% BSA (fmal concentration: 1% BSA) was added to the collected culture medium, and stored at −80° C. prior to CIU measurement.

When the CA promoter was used, the spread of GFP was detected 72 hours after the transfection, and efficient propagation was also seen after the LLC-MK2/F7/A cells were overlaid. Meanwhile, when the CMV promoter was used, GFP fluorescence was not detected 72 hours after the transfection, but a small spread of GFP was at last observed 48 hours after overlaying the LLC-MK2/F7/A cells. The CA promoter was 1000 times or more efficient for vector reconstitution. Thus, the CA promoter is much more suitable for recovering vectors than the CMV promoter.

The recovery efficiency was examined using a combination of the genes that are under the control of the CMV promoter and those that are under the control of the CA promoter. The recovery efficiency was much higher when all helper plasmids were driven by the CA promoter than by the combination of CMV and CA.

INDUSTRIAL APPLICABILITY

The method of the present invention can highly efficiently produce minus-strand RNA viral vectors without using a vaccinia virus and provides high safety production processes and products. In particular, according to the present invention, minus-strand RNA viral vectors deficient in envelope-constituting protein genes, such as the F, HN, and/or M genes, can be produced without depending on vaccinia virus. The method of the present invention is particularly useful for producing vectors that require high safety, such as vectors for gene therapy.

The invention claimed is:

1. A method for producing a Sendai virus vector, which comprises the steps Of:
   expressing a bacteriophage RNA polymerase-encoding DNA under the direct control of a cytomegalovirus enhancer and chicken β-actin promoter-comprising promoter in a virus-producing cell selected from the group consisting of a 293T cell and a BHK-21 cell;
   transcribing with the RNA polymerase, a DNA that encodes the Sendai virus genome RNA or the complementary strand thereof, and that is operably linked with a recognition sequence of the RNA polymerase in the virus-producing cell;
   and expressing Sendai virus N (nucleocapsid), P (phospho), and L (large) proteins that form a ribonucleoprotein with the genome RNA under the direct control of the cytomegalovirus enhancer and chicken β-actin promoter-comprising promoter in the virus-producing cell, wherein said method produces at least 1000-fold more of said Sendai virus vector than a method where said cytomegalovirus enhancer and chicken β-actin promoter-comprising promoter is replaced by a cytomegalovirus (CMV) promoter.

2. The method of claim 1, wherein the RNA polymerase-encoding DNA is expressed episomally in the virus-producing cell.

3. The method of claim 1, wherein the RNA polymerase-encoding DNA is expressed from a chromosome in the virus-producing cell.

4. The method of claim 1, wherein the bacteriophage is selected from the group consisting of SP6 phage, T3 phage, and T7 phage.

5. The method of claim 1, wherein the genome RNA or the complementary strand thereof lacks one or more genes encoding an envelope-constituting protein, and wherein the method further comprises the step of expressing a DNA encoding an envelope-constituting protein in the cell.

* * * * *

SEQUENCE LISTING

```
<160> NUMBER OF SEQ ID NOS: 41

<210> SEQ ID NO 1
<211> LENGTH: 367
<212> TYPE: DNA
<213> ORGANISM: Cytomegalovirus

<400> SEQUENCE: 1
actagttatt aatagtaatc aattacgggg tcattagttc atagcccata tatggagttc    60
cgcgttacat aacttacggt aaatggcccg cctggctgac cgcccaacga ccccgccca   120 ttgacgtcaa taatgacgta tgttcccata gtaacgccaa tagggacttt ccattgacgt   180
caatgggtgg agtatttacg gtaaactgcc cacttggcag tacatcaagt gtatcatatg   240
ccaagtacgc cccctattga cgtcaatgac ggtaaatggc ccgcctggca ttatgcccag   300
tacatgacct tatgggactt tcctacttgg cagtacatct acgtattagt catcgctatt   360
accatgg                                                             367

<210> SEQ ID NO 2
<211> LENGTH: 1248
<212> TYPE: DNA
<213> ORGANISM: Gallus gallus

<400> SEQUENCE: 2
tcgaggtgag ccccacgttc tgcttcactc tccccatctc cccccctcc ccaccccaa     60 ttttgtattt atttattttt taattatttt gtgcagcgat gggggcgggg ggggggggg   120 ggcgcgcgcc aggcggggcg gggcggggcg agggcgggg cggggcgagg cggagaggtg   180
cggcggcagc caatcagagc ggcgcgctcc gaaagtttcc ttttatggcg aggcggcggc   240
ggcggcggcc ctataaaaag cgaagcgcgc ggcgggcggg gagtcgctgc gacgctgcct   300
tcgccccgtg ccccgctccg ccgccgcctc gcgccgcccc ccccggctct gactgaccgc   360
gttactccca caggtgagcg ggcgggacgg cccttctcct ccgggctgta attagcgctt   420
ggtttaatga cggcttgttt cttttctgtg gctgcgtgaa agccttgagg ggctccggga   480
gggccctttg tgcgggggga gcggctcggg gggtgcgtgc gtgtgtgtgt gcgtggggag   540
cgccgcgtgc ggctccgcgc tgcccggcgg ctgtgagcgc tgcgggcgcg gcgcggggct   600
ttgtgcgctc cgcagtgtgc gcgaggggag cgcggccggg ggcggtgccc cgcggtgcgg   660 gggggctgc gagggaaca aaggctgcgt gcggggtgtg tgcgtggggg ggtgagcagg    720
gggtgtgggc gcgtcggtcg ggctgcaacc cccctgcac ccccctcccc gagttgctga   780
gcacggcccg gcttcgggtg cggggctccg tacggggcgt ggcgcggggc tcgccgtgcc   840 gggcggggg tggcggcagg tgggggtgcc gggcggggcg gggccgcctc gggccgggga   900
gggctcgggg gaggggcgcg gcggccccg gagcgccggc ggctgtcgag gcgcggcgag   960
ccgcagccat tgccttttat ggtaatcgtg cgagagggcg cagggacttc ctttgtccca  1020
aatctgtgcg gagccgaaat ctgggaggcg ccgccgcacc ccctctagcg ggcgcggggc  1080
```

```
gaagcggtgc ggcgccggca ggaaggaaat gggcggggag ggccttcgtg cgtcgccgcg    1140
ccgccgtccc cttctccctc tccagcctcg gggctgtccg cggggggacg gctgccttcg    1200 gggggacgg ggcagggcgg ggttcggctt ctggcgtgtg accggcgg                  1248

<210> SEQ ID NO 3
<211> LENGTH: 95
<212> TYPE: DNA
<213> ORGANISM: Oryctolagus cuniculus

<400> SEQUENCE: 3
cctctgctaa ccatgttcat gccttcttct ttttcctaca gctcctgggc aacgtgctgg     60
ttattgtgct gtctcatcat tttggcaaag aattc                                95

<210> SEQ ID NO 4
<211> LENGTH: 1744
<212> TYPE: DNA
<213> ORGANISM: Artificial
<220> FEATURE:
<223> OTHER INFORMATION: an example of CA promoter

<400> SEQUENCE: 4
actagttatt aatagtaatc aattacgggg tcattagttc atagcccata tatggagttc     60
cgcgttacat aacttacggt aaatggcccg cctggctgac cgcccaacga ccccccgccca    120 ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct acgtattagt catcgctatt    360
accatggtcg aggtgagccc cacgttctgc ttcactctcc ccatctcccc ccctcccca    420 ccccaatttt gtatttattt attttttaa ttattttgtg cagcgatggg ggcggggggg    480
gggggggggc gcgcgccagg cggggcgggg cggggcgagg ggcggggcgg ggcgaggcgg    540
agaggtgcgg cggcagccaa tcagagcggc gcgctccgaa agtttccttt tatgcgaggg    600
cggcggcggc ggcggcccta taaaaagcga agcgcgcggc gggcggggag tcgctgcgac    660
gctgccttcg ccccgtgccc cgctccgccg ccgcctcgcg ccgcccgccc cggctctgac    720
tgaccgcgtt actcccacag gtgagcgggc gggacggccc ttctcctccg ggctgtaatt    780
agcgcttggt ttaatgacgg cttgtttctt ttctgtggct gcgtgaaagc cttgagggc    840 tccgggaggg cccttttgtgc gggggagcg gctcggggg tgcgtgcgtg tgtgtgtgcg    900 tgggagcgc cgcgtgcggc tccgcgctgc ccggcggctg tgagcgctgc gggcgcggcg    960
cggggctttg tgcgctccgc agtgtgcgcg aggggagcgc ggccggggc ggtgccccgc    1020 ggtgcggggg gggctgcgag gggaacaaag gctgcgtgcg ggtgtgtgc gtgggggggt    1080 gagcaggggg tgtgggcgcg tcggtcgggc tgcaaccccc cctgcacccc cctccccgag    1140
ttgctgagca cggcccggct tcgggtgcgg ggctccgtac ggggcgtggc gcggggctcg    1200
ccgtgccggg cgggggtgg cggcaggtgg gggtgccggg cggggcgggg ccgctcgggg    1260
ccggggaggg ctcggggag gggcgcggcg gccccggag cgccggcggc tgtcgaggcg    1320
cggcgagccg cagccattgc cttttatggt aatcgtgcga gagggcgcag ggacttcctt    1380
tgtcccaaat ctgtgcggag ccgaaatctg ggaggcgccg ccgcaccccc tctagcgggc    1440
gcggggcgaa gcggtgcggc gccggcagga aggaaatggg cggggagggc cttcgtgcgt    1500
cgccgcgccg ccgtcccctt ctccctctcc agcctcgggg ctgtccgcgg gggacggct    1560
```

```
gccttcgggg gggacggggc agggcggggt tcggcttctg gcgtgtgacc ggcggctcta    1620
gagcctctgc taaccatgtt catgccttct tctttttcct acagctcctg ggcaacgtgc    1680
tggttattgt gctgtctcat cattttggca aagaattcgg cttgatcgaa gcttgcccac    1740
catg                                                                 1744

<210> SEQ ID NO 5
<211> LENGTH: 24
<212> TYPE: RNA
<213> ORGANISM: Artificial
<220> FEATURE:
<223> OTHER INFORMATION: an example of a hammerhead ribozyme
<220> FEATURE:
<221> NAME/KEY: misc_feature
<222> LOCATION: (5)..(5)
<223> OTHER INFORMATION: g or a or u or c
<220> FEATURE:
<221> NAME/KEY: misc_feature
<222> LOCATION: (8)..(19)
<223> OTHER INFORMATION: g or a or u or c
<220> FEATURE:
<221> NAME/KEY: misc_feature
<222> LOCATION: (24)..(24)
<223> OTHER INFORMATION: g or a or u or c

<400> SEQUENCE: 5
cugangannn nnnnnnnnng aaan                                            24

<210> SEQ ID NO 6
<211> LENGTH: 23
<212> TYPE: DNA
<213> ORGANISM: Bacteriophage T7

<400> SEQUENCE: 6
taatacgact cactataggg aga                                             23

<210> SEQ ID NO 7
<211> LENGTH: 23
<212> TYPE: DNA
<213> ORGANISM: Bacteriophage T3

<400> SEQUENCE: 7
aattaaccct cactaaggg aga                                              23

<210> SEQ ID NO 8
<211> LENGTH: 23
<212> TYPE: DNA
<213> ORGANISM: Bacteriophage SP6
<220> FEATURE:
<221> NAME/KEY: misc_feature
<222> LOCATION: (22)..(22)
<223> OTHER INFORMATION: a or g or c or t

<400> SEQUENCE: 8
atttaggtga cactatagaa gng                                             23

<210> SEQ ID NO 9
<211> LENGTH: 34
<212> TYPE: DNA
<213> ORGANISM: Bacteriophage P1

<400> SEQUENCE: 9
ataacttcgt ataatgtatg ctatacgaag ttat                                 34

<210> SEQ ID NO 10
<211> LENGTH: 34
```

```
<212> TYPE: DNA
<213> ORGANISM: Saccharomyces cerevisiae

<400> SEQUENCE: 10
gaagttccta ttctctagaa agtataggaa cttc                              34

<210> SEQ ID NO 11
<211> LENGTH: 10
<212> TYPE: RNA
<213> ORGANISM: Artificial
<220> FEATURE:
<223> OTHER INFORMATION: an example of Sendai virus S sequence (w= a or
      c; v=a or c or g)

<400> SEQUENCE: 11 ucccwvuuwc                                                         10

<210> SEQ ID NO 12
<211> LENGTH: 10
<212> TYPE: RNA
<213> ORGANISM: Artificial
<220> FEATURE:
<223> OTHER INFORMATION: an example of Sendai virus S sequence

<400> SEQUENCE: 12
ucccaguuuc                                                         10

<210> SEQ ID NO 13
<211> LENGTH: 10
<212> TYPE: RNA
<213> ORGANISM: Artificial
<220> FEATURE:
<223> OTHER INFORMATION: an example of Sendai virus S sequence

<400> SEQUENCE: 13
ucccacuuac                                                         10

<210> SEQ ID NO 14
<211> LENGTH: 10
<212> TYPE: RNA
<213> ORGANISM: Artificial
<220> FEATURE:
<223> OTHER INFORMATION: an example of Sendai virus S sequence

<400> SEQUENCE: 14
ucccacuuuc                                                         10

<210> SEQ ID NO 15
<211> LENGTH: 10
<212> TYPE: DNA
<213> ORGANISM: Artificial
<220> FEATURE:
<223> OTHER INFORMATION: an example of Sendai virus S sequence

<400> SEQUENCE: 15
agggtcaaag                                                         10

<210> SEQ ID NO 16
<211> LENGTH: 10
<212> TYPE: DNA
<213> ORGANISM: Artificial
<220> FEATURE:
<223> OTHER INFORMATION: an example of Sendai virus S sequence

<400> SEQUENCE: 16
agggtgaatg                                                         10
```

```
<210> SEQ ID NO 17
<211> LENGTH: 10
<212> TYPE: DNA
<213> ORGANISM: Artificial
<220> FEATURE:
<223> OTHER INFORMATION: an example of Sendai virus S sequence

<400> SEQUENCE: 17
agggtgaaag                                                              10

<210> SEQ ID NO 18
<211> LENGTH: 9
<212> TYPE: RNA
<213> ORGANISM: Artificial
<220> FEATURE:
<223> OTHER INFORMATION: an example of Sendai virus E sequence

<400> SEQUENCE: 18 auucuuuuu                                                                9

<210> SEQ ID NO 19
<211> LENGTH: 9
<212> TYPE: DNA
<213> ORGANISM: Artificial
<220> FEATURE:
<223> OTHER INFORMATION: an example of Sendai virus E sequence

<400> SEQUENCE: 19 taagaaaaa                                                                9

<210> SEQ ID NO 20
<211> LENGTH: 10
<212> TYPE: DNA
<213> ORGANISM: Artificial
<220> FEATURE:
<223> OTHER INFORMATION: an example of Sendai virus S sequence

<400> SEQUENCE: 20
ctttcaccct                                                              10

<210> SEQ ID NO 21
<211> LENGTH: 15
<212> TYPE: DNA
<213> ORGANISM: Artificial
<220> FEATURE:
<223> OTHER INFORMATION: an example of Sendai virus E sequence

<400> SEQUENCE: 21
tttttcttac tacgg                                                        15

<210> SEQ ID NO 22
<211> LENGTH: 54
<212> TYPE: DNA
<213> ORGANISM: Artificial
<220> FEATURE:
<223> OTHER INFORMATION: an artificially synthesized sequence

<400> SEQUENCE: 22
tctcgagtcg ctcggtacga tggccaagtt gaccagtgcc gttccggtgc tcac             54

<210> SEQ ID NO 23
<211> LENGTH: 85
<212> TYPE: DNA
<213> ORGANISM: Artificial
<220> FEATURE:
<223> OTHER INFORMATION: an artificially synthesized sequence
```

```
<400> SEQUENCE: 23
aatgcatgat cagtaaatta caatgaacat cgaacccag agtcccgctc agtcctgctc    60
ctcggccacg aagtgcacgc agttg                                         85

<210> SEQ ID NO 24
<211> LENGTH: 40
<212> TYPE: DNA
<213> ORGANISM: Artificial
<220> FEATURE:
<223> OTHER INFORMATION: an artificially synthesized sequence

<400> SEQUENCE: 24
ccggaattca acaaatggcc gggttgttga gcaccttcga                         40

<210> SEQ ID NO 25
<211> LENGTH: 42
<212> TYPE: DNA
<213> ORGANISM: Artificial
<220> FEATURE:
<223> OTHER INFORMATION: an artificially synthesized sequence

<400> SEQUENCE: 25
ccggaattcc tagattcctc ctatcccagc tactgctgct cg                      42

<210> SEQ ID NO 26
<211> LENGTH: 50
<212> TYPE: DNA
<213> ORGANISM: Artificial
<220> FEATURE:
<223> OTHER INFORMATION: an artificially synthesized sequence

<400> SEQUENCE: 26
ctagctagcc caccatggat caagatgcct tcattctaaa agaagattct               50

<210> SEQ ID NO 27
<211> LENGTH: 50
<212> TYPE: DNA
<213> ORGANISM: Artificial
<220> FEATURE:
<223> OTHER INFORMATION: an artificially synthesized sequence

<400> SEQUENCE: 27
ctagctagcc tagttggtca gtgactctat gtcctcttct acgagttcca               50

<210> SEQ ID NO 28
<211> LENGTH: 29
<212> TYPE: DNA
<213> ORGANISM: Artificial
<220> FEATURE:
<223> OTHER INFORMATION: an artificially synthesized sequence

<400> SEQUENCE: 28
cattttggca aagaattgat taattcgag                                     29

<210> SEQ ID NO 29
<211> LENGTH: 47
<212> TYPE: DNA
<213> ORGANISM: Artificial
<220> FEATURE:
<223> OTHER INFORMATION: an artificially synthesized sequence

<400> SEQUENCE: 29
tcacagcacc caagaatctc ttctggcgag caccggcatt ttgtgtc                 47

<210> SEQ ID NO 30
```

```
<211> LENGTH: 47
<212> TYPE: DNA
<213> ORGANISM: Artificial
<220> FEATURE:
<223> OTHER INFORMATION: an artificially synthesized sequence

<400> SEQUENCE: 30
gacacaaaat gccggtgctc gccagaagag attcttgggt gctgtga                        47

<210> SEQ ID NO 31
<211> LENGTH: 42
<212> TYPE: DNA
<213> ORGANISM: Artificial
<220> FEATURE:
<223> OTHER INFORMATION: an artificially synthesized sequence

<400> SEQUENCE: 31
gatcgtaatc acagtctctc gagagttgta ccatctacct ac                             42

<210> SEQ ID NO 32
<211> LENGTH: 52
<212> TYPE: DNA
<213> ORGANISM: Artificial
<220> FEATURE:
<223> OTHER INFORMATION: an artificially synthesized sequence

<400> SEQUENCE: 32
tcacagcacc gaagaatctc ctccggcgac gaccggcatt ttgtgtcgta tc                  52

<210> SEQ ID NO 33
<211> LENGTH: 52
<212> TYPE: DNA
<213> ORGANISM: Artificial
<220> FEATURE:
<223> OTHER INFORMATION: an artificially synthesized sequence

<400> SEQUENCE: 33
gatacgacac aaaatgccgg tcgtcgccgg aggagattct tcggtgctgt ga                  52

<210> SEQ ID NO 34
<211> LENGTH: 23
<212> TYPE: DNA
<213> ORGANISM: Artificial
<220> FEATURE:
<223> OTHER INFORMATION: an artificially synthesized sequence

<400> SEQUENCE: 34
aaatcctgga gtgtctttag agc                                                  23

<210> SEQ ID NO 35
<211> LENGTH: 39
<212> TYPE: DNA
<213> ORGANISM: Artificial
<220> FEATURE:
<223> OTHER INFORMATION: an artificially synthesized sequence

<400> SEQUENCE: 35
ggccgcgtcg acatcgatgc tagcctcgag ccgcggtac                                 39

<210> SEQ ID NO 36
<211> LENGTH: 31
<212> TYPE: DNA
<213> ORGANISM: Artificial
<220> FEATURE:
<223> OTHER INFORMATION: an artificially synthesized sequence

<400> SEQUENCE: 36
```

-continued

```
cgcggctcga ggctagcatc gatgtcgacg c                                      31

<210> SEQ ID NO 37
<211> LENGTH: 22
<212> TYPE: DNA
<213> ORGANISM: Artificial
<220> FEATURE:
<223> OTHER INFORMATION: an artificially synthesized sequence

<400> SEQUENCE: 37
cttaactatg cggcatcaga gc                                                22

<210> SEQ ID NO 38
<211> LENGTH: 22
<212> TYPE: DNA
<213> ORGANISM: Artificial
<220> FEATURE:
<223> OTHER INFORMATION: an artificially synthesized sequence

<400> SEQUENCE: 38
gccgattcat taatgcagct gg                                                22

<210> SEQ ID NO 39
<211> LENGTH: 37
<212> TYPE: DNA
<213> ORGANISM: Artificial
<220> FEATURE:
<223> OTHER INFORMATION: an artificially synthesized sequence

<400> SEQUENCE: 39
ctataggaaa ggaattccta tagtcaccaa acaagag                                37

<210> SEQ ID NO 40
<211> LENGTH: 38
<212> TYPE: DNA
<213> ORGANISM: Artificial
<220> FEATURE:
<223> OTHER INFORMATION: an artificially synthesized sequence

<400> SEQUENCE: 40
gatgagtccg tgaggacgaa actataggaa aggaattc                               38

<210> SEQ ID NO 41
<211> LENGTH: 40
<212> TYPE: DNA
<213> ORGANISM: Artificial
<220> FEATURE:
<223> OTHER INFORMATION: an artificially synthesized sequence

<400> SEQUENCE: 41
gcgggccctc tcttgtttgg tctgatgagt ccgtgaggac                             40
```